(12) United States Patent
Bowen et al.

(10) Patent No.: US 10,386,371 B2
(45) Date of Patent: Aug. 20, 2019

(54) METABOLIC FLUX MEASUREMENT, IMAGING AND MICROSCOPY

(75) Inventors: Benjamin P. Bowen, Walnut Creek, CA (US); Katherine B. Louie, Walnut Creek, CA (US); Trent R. Northen, Walnut Creek, CA (US); Marc K. Hellerstein, Kensington, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 624 days.

(21) Appl. No.: 14/343,334

(22) PCT Filed: Sep. 7, 2012

(86) PCT No.: PCT/US2012/054329
§ 371 (c)(1),
(2), (4) Date: Jul. 14, 2014

(87) PCT Pub. No.: WO2013/036885
PCT Pub. Date: Mar. 14, 2013

(65) Prior Publication Data
US 2014/0329274 A1 Nov. 6, 2014

Related U.S. Application Data

(60) Provisional application No. 61/532,522, filed on Sep. 8, 2011.

(51) Int. Cl.
*G01N 33/58* (2006.01)
*G16B 20/00* (2019.01)
*G01N 33/68* (2006.01)

(52) U.S. Cl.
CPC ......... *G01N 33/58* (2013.01); *G01N 33/6848* (2013.01); *G01N 2458/15* (2013.01); *G01N 2570/00* (2013.01); *G01N 2800/7028* (2013.01); *G16B 20/00* (2019.02); *Y10T 436/24* (2015.01)

(58) Field of Classification Search
None
See application file for complete search history.

(56) References Cited

U.S. PATENT DOCUMENTS

| | | |
|---|---|---|
| 4,065,552 A | 12/1977 | Costa |
| 4,332,784 A | 6/1982 | Smith et al. |
| 4,889,126 A | 12/1989 | Doddrell et al. |
| 4,940,658 A | 7/1990 | Allen et al. |
| 5,026,909 A | 6/1991 | Zoltarev et al. |
| 5,042,488 A | 8/1991 | Ackerman |
| 5,167,948 A | 12/1992 | Wenzel |
| 5,209,919 A | 5/1993 | Turteltaub et al. |
| 5,317,098 A | 5/1994 | Shizuya et al. |
| 5,338,686 A | 8/1994 | Hellerstein |
| 5,354,662 A | 10/1994 | Stone et al. |
| 5,376,355 A | 12/1994 | Turteltaub et al. |
| 5,394,236 A | 2/1995 | Murnick |
| 5,432,058 A | 7/1995 | Lange, III et al. |
| 5,439,803 A | 8/1995 | Ross et al. |
| 5,506,147 A | 4/1996 | Kolhouse et al. |
| 5,597,548 A | 1/1997 | Sherry et al. |
| 5,628,328 A | 5/1997 | Nissen et al. |
| 5,665,377 A | 9/1997 | Gonella |
| 5,665,562 A | 9/1997 | Cook |
| 5,783,445 A | 7/1998 | Murnick |
| 5,855,921 A | 1/1999 | Somlyai |
| 5,910,403 A | 6/1999 | Hellerstein |
| 5,916,537 A | 6/1999 | Kajiwara et al. |
| 5,922,554 A | 7/1999 | Fielding et al. |
| 5,924,995 A | 7/1999 | Klein et al. |
| 5,961,470 A | 10/1999 | Wagner et al. |
| 6,010,846 A | 1/2000 | Hellerstein |
| 6,031,228 A | 2/2000 | Abramson |
| 6,071,245 A | 6/2000 | Kohno et al. |
| 6,117,656 A | 9/2000 | Seed |
| 6,284,219 B1 | 9/2001 | Ajami |
| 6,306,660 B1 | 10/2001 | Messenger et al. |
| 6,329,208 B1 | 12/2001 | Jones et al. |
| 6,355,416 B1 | 3/2002 | Abramson |
| 6,391,649 B1 | 5/2002 | Chait et al. |
| 6,461,806 B1 | 10/2002 | Hellerstein |
| 6,461,870 B2 | 10/2002 | Yatscoff et al. |
| 6,468,802 B1 | 10/2002 | Yatscoff et al. |

(Continued)

FOREIGN PATENT DOCUMENTS

| | | |
|---|---|---|
| AU | 2002365268 B2 | 9/2003 |
| CA | 2464474 A1 | 7/2003 |

(Continued)

OTHER PUBLICATIONS

Gogichaeva et al. J Am Soc Mass Spectrom 2007, 18, 279-284.*
Zenobi et al. Mass Spectrometry Reviews, 1998, 17, 337-366 (Year: 1998).*
Reindl et al. Integr. Biol., 2011, 3, 460-467 (Year: 2011).*
Hellerstein et al. The American Journal of Physiology, 276(6 Pt 1), p. E1146-1170 (Year: 1999).*
International Preliminary Report on Patentability received for PCT Patent Application No. PCT/US2014/028931, dated Sep. 24, 2015, 6 pages.
Written Opinion dated Jul. 14, 2006, by the Australian Patent Office for Singapore patent application No. 200502593-7, filed on Nov. 4, 2003, 5 pages.
Australian Search Report and Written Opinion dated Aug. 5, 2009, for SG Application No. 200717391-7, filed on May 3, 2006, 7 pages.

(Continued)

*Primary Examiner* — Michael L Borin
(74) *Attorney, Agent, or Firm* — Morrison & Foerster LLP

(57) ABSTRACT

Provided herein are methods for measuring molecular flux rates of molecules of interest in a tissue sample in spatially-organized manner and generating output (e.g., an image, a heat map, a contour map, a table or a database) representing the molecular flux rates of each spatially-defined location of the sample. Provided herein are also the output, as well as systems and computer-readable medium with computer-executable instructions for determining molecular flux rates of molecules of interest in the sample.

18 Claims, 25 Drawing Sheets

(56) References Cited

U.S. PATENT DOCUMENTS

| | | |
|---|---|---|
| 6,566,086 B1 | 5/2003 | Al Athel et al. |
| 6,599,750 B2 | 7/2003 | Yatscoff et al. |
| 6,602,715 B2 | 8/2003 | Yatscoff et al. |
| 6,610,270 B1 | 8/2003 | Ajami |
| 6,625,547 B1 | 9/2003 | Korzekwa et al. |
| 6,642,059 B2 | 11/2003 | Chait et al. |
| 6,653,076 B1 | 11/2003 | Franza, Jr. et al. |
| 6,653,090 B1 | 11/2003 | Lopaschuk |
| 6,670,194 B1 | 12/2003 | Aebersold et al. |
| 6,680,203 B2 | 1/2004 | Dasseux et al. |
| 6,764,817 B1 | 7/2004 | Schneider |
| 6,783,751 B2 | 8/2004 | Heumann |
| 6,808,875 B2 | 10/2004 | Hellerstein |
| 6,835,927 B2 | 12/2004 | Becker et al. |
| 6,849,396 B2 | 2/2005 | Schneider |
| 6,872,575 B2 | 3/2005 | Regnier |
| 6,887,712 B1 | 5/2005 | Medford et al. |
| 6,902,719 B2 | 6/2005 | Wagner |
| 6,906,320 B2 | 6/2005 | Sachs et al. |
| 7,001,587 B2 | 2/2006 | Hellerstein |
| 7,022,834 B2 | 4/2006 | Hellerstein |
| 7,048,907 B2 | 5/2006 | Groman et al. |
| 7,057,168 B2 | 6/2006 | Miller et al. |
| 7,084,396 B2 | 8/2006 | Schneider |
| 7,255,850 B2 | 8/2007 | Hellerstein |
| 7,256,047 B2 | 8/2007 | Malloy et al. |
| 7,262,020 B2 | 8/2007 | Hellerstein |
| 7,307,059 B2 | 12/2007 | Hellerstein |
| 7,357,913 B2 | 4/2008 | Hellerstein |
| 7,410,633 B2 | 8/2008 | Hellerstein |
| 7,449,171 B2 | 11/2008 | Hellerstein |
| 7,504,233 B2 | 3/2009 | Hellerstein |
| 7,873,198 B2 | 1/2011 | Shepherd et al. |
| 7,910,323 B2 | 3/2011 | Hellerstein |
| 8,005,623 B2 | 8/2011 | Hellerstein |
| 8,021,644 B2 | 9/2011 | Hellerstein |
| 8,084,016 B2 | 12/2011 | Hellerstein |
| 8,129,335 B2 | 3/2012 | Hellerstein |
| 8,401,800 B2 | 3/2013 | Hellerstein |
| 8,481,478 B2 | 7/2013 | Hellerstein |
| 8,574,543 B2 | 11/2013 | Lee et al. |
| 8,663,602 B2 | 3/2014 | Hellerstein |
| 8,741,589 B2 | 6/2014 | Hellerstein |
| 8,849,581 B2 | 9/2014 | Hellerstein |
| 8,969,287 B2 | 3/2015 | Hellerstein |
| 9,037,417 B2 | 5/2015 | Hellerstein |
| 9,043,159 B2 | 5/2015 | Hellerstein |
| 9,134,319 B2 | 9/2015 | Hellerstein et al. |
| 9,737,260 B2 | 8/2017 | Hellerstein et al. |
| 2003/0068634 A1 | 4/2003 | Hellerstein |
| 2003/0119069 A1 | 6/2003 | Schneider et al. |
| 2003/0133871 A1 | 7/2003 | Hellerstein |
| 2003/0148533 A1 | 8/2003 | Malloy et al. |
| 2003/0180710 A1 | 9/2003 | Lee et al. |
| 2003/0180800 A1 | 9/2003 | Lee et al. |
| 2003/0211036 A1 | 11/2003 | Degani et al. |
| 2003/0224420 A1 | 12/2003 | Hellerstein et al. |
| 2003/0228259 A1 | 12/2003 | Hellerstein |
| 2004/0081994 A1 | 4/2004 | Hellerstein |
| 2004/0091943 A1 | 5/2004 | Schneider |
| 2004/0115131 A1 | 6/2004 | Hellerstein |
| 2004/0121305 A1 | 6/2004 | Wiegand et al. |
| 2004/0152994 A1 | 8/2004 | Meier-Augenstein |
| 2004/0191916 A1 | 9/2004 | Gross et al. |
| 2004/0253647 A1 | 12/2004 | Mathews et al. |
| 2005/0003375 A1 | 1/2005 | Franza, Jr. et al. |
| 2005/0014181 A1 | 1/2005 | Galis et al. |
| 2005/0019251 A1 | 1/2005 | Hellerstein |
| 2005/0092910 A1 | 5/2005 | Geromanos et al. |
| 2005/0118724 A1 | 6/2005 | Bateman et al. |
| 2005/0147558 A1 | 7/2005 | Hellerstein |
| 2005/0153346 A1 | 7/2005 | Schneider |
| 2005/0175982 A1 | 8/2005 | Iwatani et al. |
| 2005/0180949 A1 | 8/2005 | Emtage et al. |
| 2005/0201937 A1 | 9/2005 | Hellerstein |
| 2005/0202406 A1* | 9/2005 | Hellerstein ........ A61K 49/0008 435/4 |
| 2005/0221278 A1 | 10/2005 | Iwatani et al. |
| 2005/0238577 A1 | 10/2005 | Hellerstein |
| 2005/0238581 A1 | 10/2005 | Kurland et al. |
| 2005/0255509 A1 | 11/2005 | Hellerstein et al. |
| 2005/0281745 A1 | 12/2005 | Lee et al. |
| 2006/0008796 A1 | 1/2006 | Hellerstein |
| 2006/0029549 A1 | 2/2006 | Hellerstein |
| 2006/0094057 A1 | 5/2006 | Hellerstein |
| 2006/0100903 A1 | 5/2006 | Lee et al. |
| 2006/0105322 A1 | 5/2006 | Iwatani et al. |
| 2006/0105339 A1 | 5/2006 | Hellerstein |
| 2006/0120961 A1 | 6/2006 | Schneider et al. |
| 2006/0194877 A1 | 8/2006 | Gardiner et al. |
| 2006/0204439 A1 | 9/2006 | Hellerstein |
| 2006/0251576 A1 | 11/2006 | Hellerstein |
| 2006/0280682 A1 | 12/2006 | Hellerstein |
| 2006/0281188 A1 | 12/2006 | Mann et al. |
| 2007/0248540 A1 | 10/2007 | Hellerstein |
| 2008/0003179 A1 | 1/2008 | Hellerstein |
| 2008/0128608 A1 | 6/2008 | Northen et al. |
| 2009/0041661 A1 | 2/2009 | Hellerstein |
| 2009/0042741 A1 | 2/2009 | Northen et al. |
| 2009/0087913 A1 | 4/2009 | Sakuma |
| 2010/0056392 A1 | 3/2010 | Greving et al. |
| 2010/0099891 A1 | 4/2010 | Okuno et al. |
| 2010/0317541 A1 | 12/2010 | Addington et al. |
| 2011/0195865 A1 | 8/2011 | Hellerstein |
| 2014/0005074 A1 | 1/2014 | Hellerstein |
| 2014/0162900 A1 | 6/2014 | Hellerstein |
| 2014/0186838 A1 | 7/2014 | Hellerstein |
| 2014/0193828 A1 | 7/2014 | Hellerstein |
| 2014/0273044 A1 | 9/2014 | Hellerstein |
| 2014/0287957 A1 | 9/2014 | Prusiner et al. |
| 2014/0295484 A1 | 10/2014 | Hellerstein |
| 2014/0295485 A1 | 10/2014 | Hellerstein |
| 2014/0329274 A1 | 11/2014 | Bowen et al. |
| 2014/0353486 A1 | 12/2014 | Leonard |
| 2015/0233938 A1 | 8/2015 | Hellerstein |

FOREIGN PATENT DOCUMENTS

| | | |
|---|---|---|
| CA | 2494715 A1 | 2/2004 |
| CA | 2530789 A1 | 4/2005 |
| CA | 2840691 A1 | 4/2005 |
| CA | 2858368 A1 | 6/2013 |
| EP | 0826377 B1 | 11/2002 |
| EP | 1437966 A1 | 7/2004 |
| EP | 1663319 A2 | 6/2006 |
| EP | 2753707 A1 | 7/2014 |
| EP | 2788772 A1 | 10/2014 |
| JP | 2001-211782 A | 8/2001 |
| JP | 2003-501374 A | 1/2003 |
| JP | 2003-502016 A | 1/2003 |
| JP | 2003-79270 A | 3/2003 |
| JP | 2005-539069 A | 12/2005 |
| JP | 2005-539199 A | 12/2005 |
| JP | 2007-93597 A | 4/2007 |
| JP | 2007-536250 A | 12/2007 |
| JP | 2008-157905 A | 7/2008 |
| JP | 2008-529979 A | 8/2008 |
| JP | 2010-540911 A | 12/2010 |
| JP | 2011-180130 A | 9/2011 |
| JP | 2014-526685 A | 10/2014 |
| SU | 968036 A1 | 10/1982 |
| WO | 1990/011371 A1 | 10/1990 |
| WO | 1993/020800 A1 | 10/1993 |
| WO | 1993/025705 A1 | 12/1993 |
| WO | 1995/013096 A1 | 5/1995 |
| WO | 1998/051820 A1 | 11/1998 |
| WO | 2000/012535 A2 | 3/2000 |
| WO | 2000/013025 A1 | 3/2000 |
| WO | 2000/055355 A2 | 9/2000 |
| WO | 2000/063683 A1 | 10/2000 |
| WO | 2001/080715 A2 | 11/2001 |
| WO | 2001/084143 A1 | 11/2001 |
| WO | 2003/034024 A2 | 4/2003 |
| WO | 2003/061479 A1 | 7/2003 |

(56) References Cited

FOREIGN PATENT DOCUMENTS

| | | | |
|---|---|---|---|
| WO | 2003/068919 A2 | 8/2003 |
| WO | 2003/087314 A2 | 10/2003 |
| WO | 2004/003493 A2 | 1/2004 |
| WO | 2004/011426 A2 | 2/2004 |
| WO | 2004/016156 A2 | 2/2004 |
| WO | 2004/021863 A2 | 3/2004 |
| WO | 2004/024941 A2 | 3/2004 |
| WO | 2004/025270 A2 | 3/2004 |
| WO | 2004/042360 A2 | 5/2004 |
| WO | 2004/016156 A3 | 6/2004 |
| WO | 2005/009597 A2 | 2/2005 |
| WO | 2005/010506 A1 | 2/2005 |
| WO | 2005/015155 A2 | 2/2005 |
| WO | 2005/033652 A2 | 4/2005 |
| WO | 2005/051434 A1 | 6/2005 |
| WO | 2005/087943 A1 | 9/2005 |
| WO | 2006/050130 A2 | 5/2006 |
| WO | 2006/081521 A2 | 8/2006 |
| WO | 2006/107814 A2 | 10/2006 |
| WO | 2010012306 A1 | 2/2010 |
| WO | 2010/136455 A1 | 12/2010 |
| WO | 2010144876 A1 | 12/2010 |
| WO | 2011/004009 A1 | 1/2011 |
| WO | 2011160045 A1 | 12/2011 |
| WO | 2013/036885 A1 | 3/2013 |
| WO | 2013/086070 A1 | 6/2013 |
| WO | 2014/201291 A1 | 12/2014 |

OTHER PUBLICATIONS

Supplementary Partial Search Report Received for European Patent Application No. 02806603.3, dated Jul. 25, 2006, 5 pages.
Supplementary Partial Search Report received for European Patent Application No. 03713429.3, dated Mar. 9, 2006, 6 pages.
Supplementary Partial Search Report received for European Patent Application No. 03749756.7, dated Aug. 17, 2005, 6 pages.
Supplementary Partial Search Report received for European Patent Application No. 03768624.3, dated Sep. 22, 2006, 4 pages.
Supplementary Search Report received for European Patent Application No. 04809469.2, dated Jul. 28, 2009, 4 pages.
Search Report received for European Patent Application No. 04812281.6, dated Oct. 6, 2010, 4 pages.
Supplementary Search Report received for European Patent Application No. 05725448.4, dated Jun. 30, 2009, 7 pages.
International Search Report received for PCT Patent Application No. PCT/US1998/009479, dated Oct. 20, 1998, 3 pages.
Supplementary Search Report received for European Patent Application No. 05733311.4, dated Sep. 19, 2008, 9 pages.
International Search Report received for for PCT Patent Application No. PCT/US2003/004183, dated Jun. 29, 2004, 4 pages.
International Search Report received for for PCT Patent Application No. PCT/US2003/010554, dated Aug. 20, 2004, 4 pages.
International Search Report received for PCT Patent Application No. PCT/US2003/020052, dated Apr. 13, 2004, 3 pages.
International Search Report received for PCT Patent Application No. PCT/US2003/023340, dated Aug. 18, 2004, 4 pages.
International Search Report received for PCT Patent Application No. PCT/US2003/027623, dated Jul. 8, 2004, 4 pages.
International Search Report received for PCT Patent Application No. PCT/US2003/029361, dated Jan. 19, 2005, 4 pages.
International Search Report received for PCT Patent Application No. PCT/US2003/29526, dated Aug. 18, 2004, 3 pages.
International Search Report received for PCT Patent Application No. PCT/US2003/035107, dated Jul. 9, 2004, 2 pages.
International Search Report received for PCT Patent Application No. PCT/US2004/21063, dated Apr. 4, 2005, 2 pages.
International Search Report received for PCT Patent Application No. PCT/US2004/039722, dated Mar. 25, 2005, 3 pages.
International Search Report and Written Opinion received for PCT Patent Application No. PCT/US2005/005660, dated Oct. 11, 2007, 11 pages.
International Search Report and Written Opinion received for PCT Patent Application No. PCT/US2005/010429, dated Aug. 8, 2006, 15 pages.
International Search Report received for PCT Patent Application No. PCT/US2005/08265, dated Aug. 1, 2005, 4 pages.
International Search Report and Written Opinion received for PCT Patent Application No. PCT/US2006/017167, dated Feb. 5, 2008, 11 pages.
"NCBI Blast: Protein Sequence (17 letters)", Available at: <http://blast.ncbi.nlm.nih.gov/Blast.cgi>, Visited on May 29, 2008, 5 pages.
"New Diagnostic Technique Could Help Treat AIDS", Agence France-Presse, Dow Jones News, Feb. 17, 1998, pp. 1-2.
Zilversmit et al., "On the Calculation of 'Turnover Time' and 'Turnover Rate' from Experiments Involving the Use of Labeling Agents", J. of General Physiology, vol. 26, No. 3, 1943, pp. 325-331.
Ackermans et al., "The Quantification of Gluconeogenesis in Healthy Men by 2H2O and [2-13C]Glycerol Yields Different Results: Rates of Gluconeogenesis in Healthy Men Measured with 2H2O are Higher than those Measured with [2-13C]Glycerol", The Journal of Clinical Endocrinology & Metabolism, vol. 86, No. 5, 2001, pp. 2220-2226.
Adami et al., "The Aetiology and Pathogenesis of Human Breast Cancer", Mutation Research, vol. 333, 1995, pp. 29-35.
Airhart et al., "Compartmentation of Free Amino Acids for Protein Synthesis in Rat Liver", The Biochemical Journal, vol. 140, 1974, pp. 539-545.
Ajie et al., "In Vivo Study of the Biosynthesis of Long-Chain Fatty Acids Using Deuterated Water", The American Journal of Physiology, vol. 269, 1995, pp. E247-E252.
Anderson et al., "Direct HIV Cytopathicity Cannot Account for CD4 Decline in AIDS in the Presence of Homeostasis: A Worst-Case Dynamic Analysis", Journal of Acquired Immune Deficiency Syndromes and Human Retrovirology, vol. 17, 1998, pp. 245-252.
Antelo et al., "Adipose Triglyceride (TG) Turnover and De Novo Lipogenesis (DNL) in Humans: Measurement by Long-Term 2H2O Labeling and Mass Isotopomer Distribution Analysis (MIDA)", Experimental Biology, FASEB# 361.10, 2002, p. A400 (Abstract only).
Asher et al., "Evaluation of Cell Death in EBV-Transformed Lymphocytes Using Agarose Gel Electrophoresis, Light Microscopy and Electron Microscopy. II. Induction of Non-Classic Apoptosis ("Para-Apoptosis") by Tritiated Thymidine", Leukemia & Lymphoma, vol. 19, 1995, pp. 107-119.
Attardi et al., "Biogenesis of Mitochondria", Annual Review of Cell Biology, vol. 4, 1988, pp. 289-333.
Bach et al., "Stem Cells: The Intestinal Stem Cell as a Paradigm", Carcinogenesis, vol. 21, No. 3, 2000, pp. 469-476.
Backhouse et al., "Effects of Haloperidol on Cell Proliferation in the Early Postnatal Rat Brain", Neuropathology and Applied Neurobiology, vol. 8, No. 2, 1982, pp. 109-116.
Bandsma et al., "Contribution of Newly Synthesized Cholesterol to Rat Plasma and Bile Determined by Mass Isotopomer Distribution Analysis: Bile-Salt Flux Promotes Secretion of Newly Synthesized Cholesterol into Bile", The Biochemical Journal, vol. 329, 1998, pp. 699-703.
Bandsma et al., "The Contribution of Newly Synthesized Cholesterol to Bile Salt Synthesis in Rats Quantified by Mass Isotopomer Distribution Analysis", Biochemica et Biophysica Acta, vol. 1483, 2000, pp. 343-351.
Bertani et al., "Measurement of Total Body Water (TBW) Through In Vivo Dilution of Tracer Compounds: Use of D2O and its Determination by FT Infrared Spectroscopy", Annali Di Chimica, vol. 92, 2002, pp. 135-138.
Bickenbach, "Identification and Behavior of Label-Retaining Cells in Oral Mucosa and Skin", Journal of Dental Research, vol. 60, 1981, pp. 1611-1620.
Bier, D. M., "The Use of Stable Isotopes in Metabolic Investigation", Balliere's Clinical Endocrinology and Metabolism, vol. 1, No. 4, Nov. 1987, pp. 817-836.
Bier, D. M., "Stable Isotopes in Biosciences, their Measurement and Models for Amino Acid Metabolism", European Journal of Pediatrics, vol. 156, 1997, pp. S2-S8.

(56) References Cited

OTHER PUBLICATIONS

Bingham, Sheila A., "The Use of 24-h Urine Samples and Energy Expenditure to Validate Dietary Assessments", The American Journal of Clinical Nutrition, vol. 59(suppl), 1994, pp. 227S-231S.

Black et al., "Labeling DNA with Stable Isotopes: Economical and Practical Considerations", BioTechniques, vol. 30, 2001, pp. 134-138, 140.

Blair et al., "Changes in Physical Fitness and All-Cause Mortality. A Prospective Study of Healthy and Unhealthy Men", JAMA, vol. 273, 1995, pp. 1093-1098.

Blau et al., "Handbook of Derivatives for Chromatography", 2nd Edition, John Wiley & Sons Ltd., England, 1993.

Bonotto et al., "Study of the Distribution and Biological Effects of 3H in the Algae Acetabularia, Chlamydomonas and Porphyra", Current Topics in Radiation Research Quarterly, vol. 12, 1978, pp. 115-132.

Boros et al., "Genistein Inhibits Nonoxidative Ribose Synthesis in MIA Pancreatic Adenocarcinoma Cells: A New Mechanism of Controlling Tumor Growth", Pancreas, vol. 22, No. 1, 2001, pp. 1-7.

Boros et al., "Metabolic Profiling of Cell Growth and Death in Cancer: Applications in Drug Discovery", Drug Discovery Today, vol. 7, No. 6, Mar. 2002, pp. 364-372.

Bravo et al., "Decreased Hepatic Uptake and Processing of High Density Lipoprotein Unesterified Cholesterol and Cholesteryl Ester with Age in the Rat", Journal of Biochemistry, vol. 116, 1994, pp. 1088-1095.

Brown et al., "Treating Patients with Documented Atherosclerosis to National Cholesterol Education Program-Recommended Low-Density-Lipoprotein Cholesterol Goals with Atorvastatin, Fluvastatin, Lovastatin and Simvastatin", Journal of the American College of Cardiology, vol. 32, 1998, pp. 665-672.

Bucy et al., "Analysis of Lymph Node Biopsies in HIV Infected Patients Before and After HAART", 5th Conference on Retroviruses and Opportunistic Infections, Session 66, vol. 519, 1998, 177 Pages (Abstract only).

Caldwell et al., "Quantification of Peptide Isotopomer Abundances and Determination of Protein (sic) Turnover Rates by Using Mass Isotopomer Distribution Analysis", 41st Annual Amer. Society Mass Spectrometry on Mass Spectrometry, 1993, p. 331a (Abstract only).

Cassella et al., "Mechanisms of Lymphocyte Killing by HIV", Current Opinion in Hematology, vol. 4, 1997, pp. 24-31.

Cesar et al., "Direct Measurement of CD4+ and CD8+ T Cell Proliferation Rates in Vivo in AIDS Patients Using a Stable Isotope-Mass Spectrometric Technique", 5th Conference on Retroviruses and Opportunistic Infections, Chicago Illinois, 1998, Abstract only.

Chinkes et al., "Comparison of Mass Isotopomer Dilution Methods Used to Compute VLDL Production In Vivo", The American Journal of Physiology, vol. 271, 1996, pp. E373-E383.

Christiansen et al., "Effect of Dietary Energy Restriction on Glucose Production and Substrate Utilization in Type 2 Diabetes", Diabetes, vol. 49, Oct. 2000, pp. 1691-1699.

Clarke, R. B., "Isolation and Characterization of Human Mammary Stem Cells", Cell Proliferation, vol. 38, 2005, pp. 375-386.

Clayton, "Replication and Transcription of Vertebrate Mitochondrial DNA", Annual Review of Cell Biology, vol. 7, 1991, pp. 453-478.

Cohen et al., "Purine and Pyrimidine Metabolism in Human T Lymphocytes. Regulation of Deoxyribonucleotide Metabolism", The Journal of Biological Chemistry, vol. 258, No. 20, 1983, pp. 12334-12340.

Cohen, J. "Failure Isn't What It Used to Be . . . But Neither is Success", Science, vol. 279, 1998, pp. 1133-1134.

Collins et al., "A Method for Measuring Mitochondrial Proliferation In Vivo Using 2H2O Incorporation Into Mitochondria DNA", FASEB Journal, vol. 14, No. 4, Mar. 15, 2000, p. A620.

Collins et al., "Measurement of Mitochondrial DNA Synthesis In Vivo Using a Stable Isotope-Mass Spectrometric Technique", Journal of Applied Physiology, vol. 94, 2003, pp. 2203-2211.

Connors et al., "HIV Infection Induces Changes in CD4+ T-Cell Phenotype and Depletions Within the CD4+ T-Cell Repertoire that are Not Immediately Restored by Antiviral or Immune-Based Therapies", Nature Medicine, vol. 3, 1997, pp. 533-540.

Conrads et al., "Stable Isotope Labeling in Proteomics", The Synthesis Cambridge Isotope Laboratories, vol. 3, No. 2, Jan. 2002, pp. 1-3.

Craig et al., "The Impact of Physical Activity on Lipids, Lipoproteins, and Blood Pressure in Preadolescent Girls", Pediatrics, vol. 98, 1996, pp. 389-395.

Crain, "Preparation and Enzymatic Hydrolysis of DNA and RNA for Mass Spectrometry", Methods in Enzymology, vol. 193, 1990, pp. 782-790.

Dalvie, D. "Recent Advances in the Applications of Radioisotopes in Drug Metabolism, Toxicology and Pharmacokinetics", Current Pharmaceutical Design, vol. 6, 2000, pp. 1009-1028.

Davis et al., "Effect of Pinitol Treatment on Insulin Action in Subjects with Insulin Resistance", Diabetes Care, vol. 23, No. 7, Jul. 2000, pp. 1000-1005.

Deeks et al., "CD4+ T Cell Kinetics and Activation in Human Immunodeficiency Virus-Infected Patients who Remain Viremic Despite Long-Term Treatment with Protease Inhibitor-Based Therapy", The Journal of Infectious Diseases, vol. 185, Feb. 1, 2002, pp. 315-323.

Deeks et al., "Viral Load and CD4+ T Cell Changes in Patients Failing Potent Protease Inhibitor Therapy", 5th Conference on Retroviruses and Opportunistic Infections, Session 53, vol. 419, 1998, p. 158 (Abstract only).

Dekker et al., "Glucose Homeostasis in Children with Falciparum Malaria: Precursor Supply Limits Gluconeogenesis and Glucose Production", J. Clin. Endocrinol. Metabol., vol. 82, 1997, pp. 2514-2521.

Di Buono et al., "Comparison of Deuterium Incorporation and Mass Isotopomer Distribution Analysis for Measurement of Human Cholesterol Biosynthesis", Journal of Lipid Research, vol. 41, 2000, pp. 1516-1523.

Dimitrov et al., "Scientific Correspondence", Nature, vol. 375, 1995, pp. 194-195.

Emken, E. A., "Metabolism of Dietary Stearic Acid Relative to Other Fatty Acids in Human Subjects", The American Journal of Clinical Nutrition, vol. 60, (Suppl), 1994, pp. 1023S-1028S.

Emken et al., "Incorporation of Deuterium-Labeled Trans- and CIS-13-Octadeconoic Acids in Human Plasma Lipids", Journal of Lipid Research, vol. 24, 1983, pp. 34-41.

Etnier et al., "Metabolism of Organically Bound Tritium in Man", Radiation Research, vol. 100, 1984, pp. 487-502.

Fagerquist et al., "Elimination of the Concentration Dependence in Mass Isotopomer Abundance Mass Spectrometry of Methyl Palmitate Using Metastable Atom Bombardment", Journal of the American Society of Mass Spectrometry, vol. 12, 2001, pp. 754-761.

Fagerquist et al., "Molecular Ion Fragmentation and its Effects on Mass Isotopomer Abundances of Fatty Acid Methyl Esters Ionized by Electron Impact", Journal of the American Society of Mass Spectrometry, vol. 10, 1999, pp. 430-439.

Gasparini et al., "Amplification of DNA from Epithelial Cells in Urine", The New England Journal of Medicine, vol. 320, No. 12, 1989, p. 809.

Gerling et al., "Prediction of Liver Fibrosis According to Serum Collagen VI Level in Children with Cystic Fibrosis", The New England Journal of Medicine, vol. 336, No. 22, 1997, pp. 1611-1612.

Gorochov et al., "Perturbation of CD4+ and CD8+ T-Cell Repertoires During Progression to AIDS and Regulation of the CD4+ Repertoire During Antiviral Therapy", Nature Medicine, vol. 4, 1998, pp. 215-221.

Goz, "The Effects of Incorporation of 5-Halogenated Deoxyuridines into the DNA of Eukaryotic Cells", Pharmacological Reviews, vol. 29, 1977, pp. 249-272.

Gratzner, "Monoclonal Antibody to 5-Bromo- and 5-Iododeoxyuridine: A New Reagent for Detection of DNA Replication", Science, vol. 218, 1982, pp. 474-475.

Guo et al., "De Novo Lipogenesis in Adipose Tissue of Lean and Obese Women: Application of Deuterated Water and Isotope Ratio Mass Spectrometry", International Journal of Obesity and Related Metabolic Disorders, vol. 24, 2000, pp. 932-937.

(56) References Cited

OTHER PUBLICATIONS

Gygi et al., "Using Mass Spectrometry for Quantitative Proteomics", Proteomics: A Trends Guide, 2000, pp. 31-36.
Hansen et al., "A Practical Method for Uniform Isotopic Labeling of Recombinant Proteins in Mammalian Cells", Biochemistry, vol. 31, 1992, pp. 12713-12718.
Heck et al., "Posttranslational Amino Acid Epimerization: Enzyme-Catalyzed Isomerization of Amino Acid Residues in Peptide Chains", Proceedings of the National Academy of Sciences of the United States of America, vol. 93, Apr. 1996, pp. 4036-4039.
Hellerstein, "Mass Isotopomer Distribution Analysis: A Technique for Measuring Biosynthesis and Turnover of Polymers", The American Journal of Physiology, vol. 263, 1992, pp. E988-E1001.
Hellerstein et al., "Altered Fluxes Responsible for Reduced Hepatic Glucose Production and Gluconeogenesis by Exogenous Glucose in Rats", The American Journal of Physiology, vol. 272, 1997, pp. E163-E172.
Hellerstein et al., "Directly Measured Kinetics of Circulating T Lymphocytes in Normal and HIV-1-Infected Humans", Nature Medicine, vol. 5, 1999, pp. 83-89.
Hellerstein et al., "Effects of Cigarette Smoking and its Cessation on Lipid Metabolism and Energy Expenditure in Heavy Smokers", J. Clin. Invest., vol. 93, 1994, pp. 265-272.
Hellerstein et al., "Glycoconjugates as Noninvasive Probes of Intrahepatic Metabolism: Pathways of Glucose Entry into Compartmentalized Hepatic UDP-glucose Pools during Glycogen Accumulation", Proceedings of the National Academy of Sciences of the United States of America, vol. 83, No. 18, 1986, pp. 7044-7048.
Hellerstein et al., "Hepatic Gluconeogenic Fluxes and Glycogen Turnover During Fasting in Humans. A Stable Isotope Study", The Journal of Clinical Investigation, vol. 100, No. 5, Sep. 1997, pp. 1305-1319.
Hellerstein et al., "Mass Isotopomer Distribution Analysis at Eight Years: Theoretical, Analytic, and Experimental Considerations", The American Journal of Physiology, vol. 276, 1999, pp. E1146-E1170.
Hellerstein et al., "Mass Isotopomer Distribution Analysis for Measuring Fluxes Through Intracellular Metabolic Pathways and Biosynthetic Rates of Polymers", IFAC Modeling and Control in Biomedical Systems, 1994, pp. 353-359.
Hellerstein et al., "Measurement of Hepatic Ra UDP-Glucose in Vivo in Rats: Relation to Glycogen Deposition and Labeling Patterns", The American Journal of Physiology, vol. 272, 1997, pp. E155-E162.
Hellerstein et al., "Measurement of Synthesis Rates of Slow-turnover Proteins from 2H2O Incorporation into Non-essential Amino Acids (NEAA) and Application of Mass Isotopomer Distribution Analysis (MIDA)", Faseb Journal Experimental Biology, Meeting, vol. 16, 2002, p. A256 (Abstract only).
Jiang et al., Rb Deletion in Mouse Mammary Progenitors Induces Luminal-B or Basal-like/EMT Tumor Subtypes Depending on p53 Status, The Journal of Clinical Investigation, vol. 120, No. 9, Sep. 2010, pp. 3296-3309.
Jones et al., "Multiple Statistical Analysis Techniques Corroborate Intratumor Heterogeneity in Imaging Mass Spectrometry Datasets of Myxofibrosarcoma", Plos One, Sep. 29, 2011, 11 pages.
Jurchen et al., "MALDI-MS Imaging of Features Smaller than the Size of the Laser Beam", Journal of American Society for Mass Spectrometry, vol. 16, Aug. 10, 2005, pp. 1654-1659.
Kasumov et al., "Measuring Protein Synthesis using Metabolic 2H Labeling, High-Resolution Mass Spectrometry, and an Algorithm", Analytical Biochemistry, vol. 412, 2011, pp. 1-9.
Kennecke et al., "Metastatic Behavior of Breast Cancer Subtypes", Journal of Clinical Oncology, vol. 28, No. 20, Jul. 2010, pp. 3271-3277.
Koeniger et al., "A Quantitation Method for Mass Spectrometry Imaging", Rapid Communications in Mass Spectrometry, vol. 25, No. 4, 2011, pp. 503-510.

Lechene et al., "High-Resolution Quantitative Imaging of Mammalian and Bacterial Cells using Stable Isotope Mass Spectrometry", Journal of Biology, vol. 5, Article 20, Oct. 2006, pp. 20.1-20.30.
Lee et al., "In Vivo Measurement of Fatty Acids and Cholesterol Synthesis using D20 and Mass Isotopomer Analysis", American Journal of Physiology-Endocrinology and Metabolism, vol. 266, No. 5, 1994, pp. E699-E708.
Lee et al., "Mass Spectrometry-Based metabolomics, Analysis of Metabolite-protein Interactions, and Imaging", BioTechniques, vol. 49, No. 2, Aug. 2010, pp. 557-565.
Lee et al., "Resolving Brain Regions Using Nanostructure Initiator Mass Spectrometry Imaging", Integrative Biology, vol. 4, No. 6, Jun. 2012, pp. 693-699.
Liedtke et al., Response to Neoadjuvant Therapy and Long-Term Survival in Patients With Triple-Negative Breast Cancer, Journal of Clinical Oncology, vol. 26, No. 8, Mar. 2008, pp. 1275-1281.
Lindwal et al., "Heavy Water Labeling of Keratin as a Non-Invasive Biomarker of Skin Turnover In Vivo in Rodents and Humans", Journal of Investigative Dermatology, vol. 126, 2006, pp. 841-848.
Liu et al., "Polarity and Proliferation are Controlled by Distinct Signaling Pathways Downstream of PI3-kinase in Breast Epithelial Tumor Cells", The Journal of Cell Biology, vol. 164, No. 4, Feb. 16, 2004, pp. 603-612.
Maheo et al., "Differential Sensitization of Cancer Cells to Doxorubicin by DHA: A Role for Lipoperoxidation", Free Radical Biology & Medicine, vol. 39, Issue. 6, Sep. 15, 2005, pp. 742-751.
Marusyk et al., "Tumor Heterogeneity: Causes and Consequences", Biochimical Biophysical Acta, vol. 1805, Issue. 1, Jan. 2010, pp. 105-117.
McCubrey et al., "Roles of the Raf/MEK/ERK Pathway in Cell Growth, Malignant Transformation and Drug Resistance", Biochimical Biophysical Acta, vol. 1773, 2007, pp. 1263-1284.
McMahon et al., "Quantitative Imaging of Cells with Multiisotope Imaging Mass Spectrometry (MIMS)—Nanoautography with Stable Isotope Tracers", National Resource for Imaging Mass Spectrometry, vol. 252, Issue 19, Jul. 30, 2006, pp. 6895-6906.
Murphy et al., "Imaging of Lipid Species by MALDI Mass Spectrometry", Journal of Lipid Research, Apr. 2009, pp. S317-S322.
Neve et al., "A Collection of Breast Cancer Cell Lines for the Study of Functionally Distinct Cancer Subtypes", Cancer Cell, vol. 10, No. 6, Dec. 2006, pp. 515-527.
Nordstrom et al., "Metabolomics: Moving to the Clinic", Journal of Neuroimmune Pharmacology, vol. 5, No. 1, 2009, pp. 4-17.
Northen et al., "A Nanostructure-Initiator Mass Spectrometry-Based Enzyme Activity Assay", PNAS, vol. 105, No. 10, Mar. 11, 2008, pp. 3678-3683.
Northen et al., "Clathrate Nanostructures for Mass Spectrometry", Nature, vol. 449, No. 7165, Oct. 25, 2007, pp. 1033-1036.
Ogretmen et al., "Biologically Active Sphingolipids in Cancer Pathogenesis and Treatment", Nature Reviews Cancer, vol. 4, No. 8, 2004, pp. 604-616.
International Written Opinion received for PCT Patent Application No. PCT/US2004/039722, dated Mar. 25, 2005, 3 pages.
Price et al., "Analysis of Proteome Dynamics in the Mouse Brain", PNAS, vol. 107, No. 32, Aug. 10, 2010, pp. 14508-14513.
Quehenberger et al., "The Human Plasma Lipidome", The New England Journal of Medicine, vol. 365, No. 19, Nov. 2011, pp. 1812-1823.
Reindl et al., Multivariate Analysis of a 3D Mass Spectral Image for Examining Tissue Heterogeneity, Integrative Biology, vol. 3, No. 4, Apr. 2011, pp. 460-467.
Reindl et al., "Rapid Screening of Fatty Acids Using NanostructureInitiator Mass Spectrometry", Analytical Chemistry, vol. 82, No. 9, 2010, pp. 3751-3755.
Reis-Filho et al., "Triple Negative Tumours: A Critical Review", Histopathology, vol. 52, 2008, pp. 108-118.
Robinson et al., "Long-Term Synthesis Rates of Skeletal Muscle DNA and Protein are Higher during Aerobic Training in Older Humans than in Sedentary Young Subjects but are Not Altered by Protein Supplementation", The FASEB Journal, vol. 25 No. 9, 2011, pp. 3240-3249.

(56) References Cited

OTHER PUBLICATIONS

Rockwood et al., "Dissociation of Individual Isotopic Peaks: Predicting Isotopic Distributions of Product Ions in MSn", American Society for Mass Spectrometry, Jan. 18, 2003, pp. 311-322.
Rockwood et al., "Rapid Calculation of Isotope Distributions", Analytical Chernistry, vol. 67, No. 15, 1995, pp. 2699-2704.
Rockwood et al., "Ultrahigh-Speed Calculation of Isotope Distributions", Analytical Chemistry, vol. 68, No. 13, 1996, pp. 2027-2030.
Roddy et al., "Imaging of Freeze-Fractured Cells with in Situ Fluorescence and Time-of-Flight Secondary Ion Mass Spectrometry", Analytical Chemistry, vol. 74, No. 16, 2002, pp. 4011-4019.
Schiller et al., "Matrix-Assisted Laser Desorption and Ionization Time-of-Flight (MALDI-TOF) Mass Spectrometry in Lipid and Phospholipid Research", Progress in Lipid Research, vol. 43, 2004, pp. 449-488.
Schwamborn et al., "R.M. Molecular Imaging by Mass Spectrometry-Looking Beyond Classical Histology", Nature Reviews Cancer, vol. 10, 2010, pp. 639-646.
Spector et al., "Membrane Lipid Composition and Cellular Function", Journal of Lipid Research, vol. 26, 1985, pp. 1015-1035.
Sperling et al., "Quantitative Analysis of Isotope Distributions in Proteomic Mass Spectrometry Using Least-Squares Fourier Transform Convolution", Analytical Chemistry, vol. 80, No. 13, Jul. 1, 2008, pp. 4906-4917.
Swinnen et al., "Increased Lipogenesis in Cancer Cells: New Players, Novel Targets", Current Opinion in Clinical Nutrition and Metabolic Care, vol. 9, 2006, pp. 358-365.
Takats et al., "Mass Spectrometry Sampling Under Ambient Conditions with Desorption Electrospray Ionization", Science, vol. 306, Oct. 2004, pp. 471-473.
Tennant et al., "Metabolic Transformation in Cancer", Carcinogenesis, vol. 30, No. 8, 2009, pp. 1269-1280.
Trere et al., "High Prevalence of Retinoblastoma Protein Loss in Triple-Negative Breast Cancers and its Association with a Good Prognosis in Patients Treated with Adjuvant Chemotherapy", Annals of Oncology, vol. 20, No. 11, Nov. 2009, pp. 1818-1823.
Viale et al., "Current Concepts on Hyperpolarized Molecules in MRI", Current Opinion in Chemical Biology, vol. 14, No. 1, 2010, pp. 90-96.
Weigelt et al., "Breast Cancer Metastasis: Markers and Models", Nature, vol. 5, Aug. 2005, pp. 591-602.
Winograd et al., "Improvements in SIMS Continueis the End in Sight?", Applied Surface Science, vol. 252, No. 19, 2006, pp. 6836-6843.
Wiseman et al., "Desorption Electrospray Ionization Mass Spectrometry: Imaging Drugs and Metabolites in Tissues", Proceedings of the National Academy of Sciences, vol. 105, No. 47, Nov. 25, 2008, pp. 18120-18125.
Yanes et al., Nanostructure Initiator Mass Spectrometry: Tissue Imaging and Direct Biofluid Analysis, Anal Chern., vol. 81, No. 8, Apr. 2009, pp. 2969-2975.
Yecies et al., "Transcriptional Control of Cellular Metabolism by mTOR Signaling", Cancer Research, vol. 71, No. 8, Apr. 15, 2011, pp. 2815-2820.
Yoshimura et al., "Real-Time Analysis of Living Animals by Electrospray Ionization Mass Spectrometry", Anal Biochemistry, vol. 417, No. 2, Oct. 2011, pp. 195-201.
Zeisel, S. H., "Choline: An Essential Nutrient for Humans", Nutrition, vol. 16, 2000, pp. 669-671.
Whittmann et al., "Application of MALDI-TOF MS to lysine-Producing Corynebacterium Glutamicum: A Novel Approach for Metabolic Flux Analysis", Eur. J. Biochem., vol. 268, 2001, pp. 2441-2455.
Winett et al., "Exercise Regimens for Men With HIV", JAMA, vol. 284, No. 2, 2000, pp. 175-176.
Wolf, George, "The Effect of Fasting and Fructose and Glucose Infusion on Gluconeogenesis and Triose Phosphate Flux in Rats in Vivo", Nutrition Reviews, vol. 53, No. 10, 1995, pp. 299-302.
Wolfe, Robert R., "Isotopic Measurement of Glucose and Lactate Kinetics", Ann. Med., vol. 22, 1990, pp. 163-170.
Wolfe et al., "Glucose Metabolism in Humans", ACS Symposium Series 258, Chapter 12, Turnund et al. ed., 1984, pp. 175-189.
Wolthers et al., "Rapid CD4+ T-Cell Turnover in HIV-1 Infection: A Paradigm Revisited", Immunology Today, vol. 19, No. 1, 1998, pp. 44-48.
Wolthers et al., "T Cell Telomere Length in HIV-1 Infection: No Evidence for Increased CD4+ T Cell Turnover", Science, vol. 274, 1996, pp. 1543-1547.
Wong et al., "From monoamines to genomic targets: a paradigm shift for drug discovery in depression", Nature Reviews Drug Discovery, vol. 3, Feb. 2004, pp. 136-151.
Wood et al., "Estimation of Pathways of Carbohydrate Metabolism", Biochemische Zeitschrift, vol. 338, 1963, pp. 809-847.
Zhang et al., "Deuterium NMR Study of the Origin of Hydrogen in Fatty Acids Produced In Vivo in Chicken.", European Journal of Lipid Science and Technology, vol. 108, 2006, pp. 125-133.
Zhang et al., "Kinetics of CD4+ T Cell Repopulation of Lymphoid Tissues after Treatment of HIV-1 Infection", Proc. Natl. Acad. Sci. USA, vol. 95, Feb. 1998, pp. 1154-1159.
Jones et al., "Interaction of Dietary Fat Saturation and Cholesterol Level on Cholesterol Synthesis Measured Using Deuterium Incorporation", Journal of Lipid Research, vol. 35, 1994, pp. 1093-1101.
Pozharisski et al., "Study of Kinetics of Epithelial Cell Populations in Normal Tissues of the Rat's Intestines and in Carcinogenesis", Exp. Path., Bd., vol. 18, 1980, pp. 387-406.
Landau et al., "Use of 2H2O for Estimating Rates of Gluconeogenesis", Journal of Clinical Investigation, vol. 95, Jan. 1995, pp. 172-178.
International Search Report received for PCT Patent Application No. PCT/US2002/033996, dated Jun. 19, 2003, 2 pages.
Extended European Search Report received for European Patent Application No. 06784805.1, dated Mar. 21, 2011, 7 pages.
Extended European Search Report received for European Patent Application No. 06759050.5, dated Mar. 31, 2011, 7 pages.
International Preliminary Report on Patentability received for PCT Patent Application No. PCT/US2004/021063 dated Jan. 3, 2006, 4 pages.
Abou-Donia et al., "Mechanisms of Joint Neurotoxicity of n-Hexane, Methyl Isobutyl Ketone and O-Ethyl 0-4-Nitrophenyl Phenylphosphonothioate in Hens", The Journal of Pharmacology and Experimental Therapeutics, vol. 257, No. 1, 1991, pp. 282-289.
Abu-Qare et al., "Quantification of Nicotine, Chlorpyrifos and Their Metabolites in Rat Plasma and Urine Using High-Performance Liquid Chromatography", Journal of Chromatography B., vol. 757, 2001, pp. 295-300.
Aydemir et al., "Effects of Defibrotide on Aorta and Brain Malondialdehyde and Antioxidants in Cholesterol-Induced Atherosclerotic Rabbits", International Journal of Clinical & Laboratory Research, vol. 30, 2000, pp. 101-107.
Bantscheff et al., "Quantitative Mass Spectrometry in Proteomics: A Critical Review", Anal. Bioanal. Chem., vol. 389, 2007, pp. 1017-1031.
Buchanan, T. A., "Pancreatic Beta-Cell Loss and Preservation in Type 2 Diabetes", Clinical Therapeutics, vol. 25, 2003, pp. B32-B46.
Chobanian et al., "Body cholesterol Metabolism in Man. II. Measurement of the Body Cholesterol Miscible Pool and Turnover Rate", Journal of Clinical Investigation, vol. 41, No. 9, 1962, pp. 1738-1744.
Duane, William C., "Measurement of Bile Acid Synthesis by Three Different Methods in Hypertriglyceridemic and Control Subjects", Journal of Lipid Research, vol. 38, 1997, pp. 183-188.
Edes et al., "Glycemic Index and Insulin Response to a Liquid Nutritional Formula Compared with a Standard Meal", Journal of the American College of Nutrition, vol. 17, No. 1, 1998, pp. 30-35.
Feldman et al., "Chlordiazepoxide-Fluoxetine Interactions on Food Intake in Free-Feeding Rats", Pharmacology Biochemistry & Behavior, vol. 8, No. 6, 1978, pp. 749-752.
Ferezou et al., "Origins of Neutral Sterols in Human Feces Studied by Stable Isotope Labeling (Deuterium and Carbon-13) Existence of an External Secretion of Cholesterol", Digestion, vol. 21, No. 5, 1981, pp. 232-243.

(56) References Cited

OTHER PUBLICATIONS

Futami et al., "An Application of the On-Line Respiratory Mass Spectrometer to the Detection of Helicobacter Pylori Infection Using 13C-Labeled Urea", Journal of the Mass Spectrometry Society of Japan, vol. 47, No. 6, 1999, pp. 386-388.
Jones et al., "Modulation of Plasma Lipid Levels and Cholesterol Kinetics by Phytosterol Versus Phytostanol Esters", Journal of Lipid Research, vol. 41, 2000, pp. 697-705.
Murphy et al., "A New, Sensitive in Vivo Diagnostic Test of Insulin Resistance: The Deuterated Oral Glucose Tolerance Test (2H-OGTT)", Diabetes, American Diabetes Association, US, vol. 53, No. Suppl. 02, Jan. 1, 2004, 2 pages.
Neher et al., "Pyruvate and Thiamine Pyrophosphate Potentiate Cyclic Nucleotide-Induced Steroidogenesis in Isolated Rat Adrenocortical Cells", J.Steroid Biochem., vol. 18, 1983, pp. 1-6.
Radziuk, J. "Insulin Sensitivity and its Measurement: Structural Commonalities among the Methods", The Journal of Endocrinology & Metabolism, vol. 85, No. 12, 2000, pp. 4426-4433.
Sakurai, Y. "The Meanings of Measuring Biological Metabolism Using a Stable Isotope Labeled Tracer: The Difference in Metabolism Between a Healthy Human and a Patient in Surgically Serious Condition", Medical Journal of Fukita Academy, vol. 20, No. 1, 1996, pp. 9-21.
Schoenheimer et al., "Deuterium as an Indicator in the Study of Intermediary Metabolism—III. The Role of the Fat Tissues", The Journal of Biological Chemistry, vol. 111, 1935, pp. 175-181.
Schoenheimer et al., "Deuterium as an Indicator in the Study of Intermediary Metabolism—IX. The Conversion of Stearic Acid into Palmitic Acid in the Organism", The Journal of Biological Chemistry, vol. 120, 1937, pp. 155-165.
Seiler et al., "The Influence of Catabolic Reactions on Polyamine Excretion", Biochem. J., vol. 225, 1985, pp. 219-226.
Shen et al., "Purification of Oligodendrocyte and Its Myelination to the Demyelinated Culture Model in Vitro", Acta Histochem. Cytochem, vol. 35, No. 2, 2002, p. 123.
Tayek et al., "Glucose Production, Recycling, and Gluconeogenesis in Normals and Diabetics: A Mass Isotopomer [U_13C] Glucose Study", Am. J. Physiol. Endocrino.l Metab., vol. 270, No. 4, Apr. 1, 1996, pp. E709-E717.
Wang et al., "Validation of a Single-Isotope-Labeled Cholesterol Tracer Approach for Measuring Human Cholesterol Absorption", Lipids, vol. 39, No. 1, 2004, pp. 87-91.
Written Opinion received for PCT Patent Application No. PCT/US2004/021063 dated Apr. 4, 2005, 3 pages.
International Preliminary Report on Patentability received for PCT Patent Application No. PCT/US2004/039722, dated May 29, 2006, 4 pages.
International Preliminary Report on Patentability received for PCT Patent Application No. PCT/US2005/005660, dated Oct. 30, 2007, 5 pages.
Comte et al., "Probing the Origin of Acetyl-CoA and Oxaloacetate Entering the Citric Acid Cycle from the 13C Labeling of Citrate Released by Perfused Rat Hearts", The Journal of Biological Chemistry, vol. 272, No. 42, Oct. 17, 1997, pp. 26117-26124.
Hinkson et al., "The Dynamic State of Protein Turnover: It's About Time", Trends in Cell Biology, vol. 21, No. 5, May 2011, pp. 293-303.
Linn et al., "Effect of Long-Term Dietary Protein Intake on Glucose Metabolism in Humans", Diabetologia, vol. 43, 2000, pp. 1257-1265.
Nordhoff et al., "Mass Spectrometry of Nucleic Acids", Mass Spectrometry Reviews, vol. 15, 1996, pp. 67-138.
Previs et al., "A Critical Evaluation of Mass Isotopomer Distribution Analysis of Gluconeogenesis in Vivo", American Journal of Physiology-Endocrinology and Metabolism, vol. 277, 1999, E154-E160.
Price et al., "Measurement of Human Plasma Proteome Dynamics with 2H2O and Liquid Chromatography Tandem Mass Spectrometry", Analytical Biochemistry, vol. 420, 2012, pp. 73-83.

Szymanski et al., "Beyond the Proteome: Non-Coding Regulatory RNAs", Genome Biology, vol. 3, No. 5, Apr. 15, 2002, pp. 1-8.
Hellerstein et al., "Model for Measuring Absolute Rates of Hepatic de Novo Lipogenesis and Reesterification of Free Fatty Acids", The American Journal of Physiology, vol. 265, 1993, pp. E814-E820.
Hellerstein et al., "Subpopulations of Long-Lived and Short-Lived T Cells in Advanced HIV-1 Infection", The Journal of Clinical Investigation, vol. 112, No. 6, 2003, pp. 956-966.
Hellerstein et al., "T Cell Turnover in HIV-1 Disease", Immunity, vol. 7, 1997, pp. 583-589.
Hellerstein, M. K., "Carbohydrate-Induced Hypertriglyceridemia: Modifying Factors and Implications for Cardiovascular Risk", Curr. Opin. Lipidology, vol. 13, 2002, pp. 33-40.
Hellerstein, M. K., "Measurement of T-Cell Kinetics: Recent Methodologic Advances", Trends Immunology Today, vol. 20, No. 10, 1999, pp. 438-441.
Hellerstein, M. K., "Methods for Measurement of Fatty Acid and Cholesterol Metabolism", Current Opinion in Lipidology,vol. 6, 1995, pp. 172-181.
Hellerstein, M. K., "New Stable Isotope-Mass Spectrometric Techniques for Measuring Fluxes through Intact Metabolic Pathways in Mammalian Systems: Introduction of Moving Pictures into Functional Genomics and Biochemical Phenotyping", Metabolic Engineering, vol. 6, 2004, pp. 85-100.
Hellerstein, M. K., "No Common Energy: de Novo Lipogenesis as the Road Less Traveled", The American Journal of Clinical Nutrition, vol. 74, 2001, pp. 707-708.
Hellerstein, M. K., "Synthesis of Fat in Response to Alterations in Diet: Insights from New Stable Isotope Methodologies", Lipids, vol. 31 (Supp), 1996, pp. S117-S125.
Hellerstein, M. K., "The Changing Face of AIDS: Translators Needed", The American Journal of Clinical Nutrition, vol. 70, 1999, pp. 787-788.
Hellerstein, Marc K., "In Vivo Measurement of Fluxes Through Metabolic Pathways: The Missing Link in Functional Genomics and Pharaceutical Research", Annu. Rev. Nutr., vol. 3, 2003, pp. 379-402.
Ho et al., "Rapid Turnover of Plasma Virions and CD4 Lymphocytes in HIV-1 Infection", Nature, vol. 373, 1995, pp. 123-126.
Hoh et al., "De Novo Lipogenesis Predicts Short-Term Body-Composition Response by Bioelectrical Impedance Analysis to Oral Nutritional Supplements in HIV-Associated Wasting", The American Journal of Physiology, vol. 68, 1998, pp. 154-163.
Hsieh et al., "Dynamics of Keratinocytes in Vivo Using 2H2O Labeling: A Sensitive Marker of Epidermal Proliferation State", J Invest Dermatol, vol. 123, 2004, pp. 530-536.
Hudgins et al., "Human Fatty Acid Synthesis is Stimulated by a Eucaloric Low Fat, High Carbohydrate Diet", J. Clin. Invest., vol. 97, No. 9, 1996, pp. 2081-2091.
Hudgins et al., "Relationship Between Carbohydrate-Induced Hypertriglyceridemia and Fatty Synthesis in Lean and Obese Subjects", J. Lipid Res., vol. 41, 2000, pp. 595-604.
Hulzebos et al., "Measurement of Parameters of Cholic Acid Kinetics in Plasma using a Microscale Stable Isotope Dilution Technique: Application to Rodents and Humans", Journal of Lipid Research, vol. 42, 2001, pp. 1923-1929.
Humphrey et al., "A New Method for the Measurement of Protein Turnover", Biochem. J., vol. 148, 1975, pp. 119-127.
Humphrey et al., "A Sensitive Method for Measuring Protein Turnover Based on the Measurement of 2-3H-labeled Amino Acids in Proteins", Biochem. J., vol. 156, 1976, pp. 561-568.
Iyengar et al., "Human Stools as a Source of Viable Colonic Epithelial Cells", The FASEB Journal, vol. 5, 1991, pp. 2856-2859.
James, J. S., "Clinical Implications of Virological Failure: Interview with Steven Deeks, M.D., San Francisco General Hospital", AIDS Treatment News, vol. 289, 1998, pp. 6-7.
Jennings et al., "The Use of Infrared Spectrophotometry for Measuring Body Water Spaces", Clinical Chemistry, vol. 45, No. 7, Jul. 1999, pp. 1077-1081.
Jones et al., "An Integrated 2H and 13C NMR Study of Gluconeogenesis and TCA Cycle Flux in Humans", American Journal of Physiology-Endocrinology and Metabolism, vol. 281, 2001, pp. E848-E856.

(56) References Cited

OTHER PUBLICATIONS

Jones et al., "Evidence for Diurnal Periodicity in Human Cholesterol Synthesis", Journal of Lipid Research, vol. 31, 1990, pp. 667-673.
Jung et al., "Metabolic Adaptations to Dietary Fat Malabsorption in Chylomicron-Deficient Mice", Biochem. J., vol. 343, 1999, pp. 473-478.
Jungas, "Fatty Acid Synthesis in Adipose Tissue Incubated in Tritiated Water", Biochemistry, vol. 7, No. 10, 1968, pp. 3708-3717.
Katz, "Futile Cycles in the Metabolism of Glucose", Curr. Top Cell Regul., vol. 10, 1976, pp. 237-289.
Kelleher et al., "Model Equations for Condensation Biosynthesis Using Stable Isotopes and Radioisotopes", Am. J. Physiol., vol. 262, 1992, pp. E118-E125.
Khairallah et al., "Assessment of Protein Turnover in Perfused Rat Liver: Evidence for Amino Acid Compartmentation from Differential Labeling of Free and tRNA-bound Valine", J Biol Chem, vol. 251, No. 5, 1976, pp. 1375-1384.
Kim et al., "A New Stable Isotope-Mass Spectrometric (MS) Method to Measure Proliferation Rates of Colon Epithelial Cells", Faseb Journal, vol. 14, No. 4, 2000, p. A718.
Lammert et al., "Effects of Isoenergetic Overfeeding of Either Carbohydrate or Fat in Young Men", British Journal of Nutrition, vol. 84, 2000, pp. 233-245.
Lee, "Cardiorespiratory Fitness, Body Composition, and All-Cause and Cardiovascular Disease Mortality in Men 1-3", Am. J. Clin. Nutr., vol. 69, 1999, pp. 373-380.
Lefebvre, "Naturally Labeled 13C-Glucose: A New Tool to Measure Oxidation Rates of Exogenous Glucose", Diabetes, vol. 28 (Suppl. 1), Jan. 1979, pp. 63-65.
Leung et al., "A Deficiency of Microsomal Triglyceride Transfer Protein Reduces Apolipoprotein B Secretion", The Journal of Biological Chemistry, vol. 275, No. 11, 2000, pp. 7515-7520.
Lewanczuk et al., "Comparison of the [13 C] Glucose Breath Test to the Hyperinsulinemic-Euglycemic Clamp When Determining Insulin Resistance", Diabetes Care, vol. 27, No. 2, 2004, pp. 441-447.
Lipkin, "Cell Proliferation Kinetics in the Gastrointestinal Tract of Man. I. Cell Renewal in Colon and Rectum", Journal of Clinical Investigations, vol. 42, No. 6, 1963, pp. 767-776.
Lipkin, "Proliferation and Differentiation of Normal and Diseased Gastrointestinal Cells", In Physiology of the Gastrointestinal Tract, L.R. Johnson ed., Raven Press, New York, 1987, pp. 255-284.
Lutton et al., "Critical analysis of the Use of 14C-acetate for Measuring In Vivo Rat Cholesterol Synthesis", Reprod. Nutr. Dev., vol. 30, 1990, pp. 71-84.
Macallan et al., "Measurement of Cell Proliferation by Labeling of DNA with Stable Isotope-Labeled Glucose: Studies in Vitro, in Animals, and in Humans", Proc. Natl. Acad. Sci., vol. 95, 1998, pp. 708-713.
Maentausta et al., "Radioimmunoassay of Conjugated Cholic Acid, Chenodeoxycholic Acid, and Deoxycholic Acid from Human Serum, with Use of 125I-Labeled Ligands", Clin. Chem., vol. 25, No. 2, 1979, pp. 264-268.
Malberg et al., "Chronic Antidepressant Treatment Increases Neurogenesis in Adult Rat Hippocampus", The Journal of Neuroscience, vol. 20, No. 24, Dec. 15, 2000, pp. 9104-9110.
Margolick et al., "Failure of T-cell Homeostasis Preceding AIDS in HIV-1 Infection", Nature Medicine, vol. 1, No. 7, 1995, pp. 674-680.
Maric et al., "Functional Ionotropic Glutamate Receptors Emerge During Terminal Cell Division and Early Neuronal Differentiation of Rat Neuroepithelial Cells", Journal of Neuroscience Research, vol. 61, No. 6, 2000, pp. 652-662.
Marin et al., "Dynamic Profiling of the Glucose Metabolic Network in Fasted Rat Hepatocytes using [1,2-13C2] Glucose", Biochemical Journal, vol. 381, 2004, pp. 287-294.
Martin et al., "Discovery of a Human Liver Glycogen Phosphorylase Inhibitor That Lowers Blood Glucose in Vivo", Proc. Natl. Acad. Sci. USA, vol. 95, No. 4, 1998, pp. 1776-1781.

Mathur-De Vre et al., "Molecular Aspects of Tritiated Water and Natural Water in Radiation Biology", Prog. Biophys. Molec. Biol., vol. 43, 1984, pp. 161-193.
McCloskey, James A., "ElectronIonization Mass Spectra of Trimethylsilyl Derivatives of Nucleosides", Meth. Enz., vol. 193, 1990, pp. 825-841.
McCune et al., "Factors Influencing T-Cell Turnover in HIV-1-Seropositive Patients", J. Clin. Invest., vol. 105, 2000, pp. R1-R8.
McCune, J. M., "Thymic Function in HIV-1 Disease", Seminars in Immunology, vol. 9, 1997, pp. 397-404.
McFarland et al., "Inhibition of DNA Synthesis in Neonatal Rat Brain Regions Caused by Acute Nicotine Administration", Developmental Brain Research, vol. 58, No. 2, Feb. 22, 1991, pp. 223-229.
Ahmad et al., "Systematic Analysis of Protein Pools, Isoforms, and Modifications Affecting Turnover and Subcellular Localization", Molecular & Cellular Proteomics, vol. 11, No. 3, Mar. 2012, pp. 1-15.
Kito et al., "Mass Spectrometry-Based Approaches toward Absolute Quantitative Proteomics", Current Genomics, vol. 9, No. 4, Jun. 2008, pp. 263-274.
Macneil et al., "Analysis of Creatine, Creatinine, Creatine-$d_3$ and Creatinine-$d_3$ in Urine, Plasma, and Red Blood Cells by HPLC and GC—MS to follow the Fate of Ingested Creatine-$d_3$", Journal of Chromatography B, vol. 827, Issue 2, 2005, pp. 210-215.
Previs, Stephen F., "Application of Mass Isotopomer Distribution Analysis to Measurement of Gluconeogenesis and Glycerol Metabolism", Case Western University, May 1997, 360 pages.
International Preliminary Report on Patentability received for PCT Patent Application No. PCT/US2014/042186, dated Dec. 23, 2015, 8 pages.
Office Action received for European Patent Application No. 12830717.0, dated Feb. 24, 2016, 4 pages.
McLean et al., "In Vivo Estimates of Division and Death Rates of Human T Lymphocytes", Proc. Natl. Acad. Sci USA, vol. 92, 1995, pp. 3707-3711.
Meier et al., "Rates of Protein Synthesis and Turnover in Fetal Life", Am J Physiol., vol. 240, No. 3, 1981, pp. E320-E324.
Mellors et al., "Prognosis in HIV-1 Infection Predicted by the Quantity of Virus in Plasma", Science, vol. 272, 1996, pp. 1167-1170.
Mellors et al., "Quantitation of HIV-1 RNA in Plasma Predicts Outcome after Seroconversion", Ann. Intern. Med., vol. 122, 1995, pp. 573-579.
Messmer et al., "In Vivo Measurements Document the Dynamic Cellular Kinetics of Chronic Lymphocytic Leukemia B Cells", J. Clin. Invest., vol. 115, Feb. 10, 2005, pp. 755-764.
Mewissen et al., "Comparative Incorporation of Tritium from Tritiated Water Versus Tritiated Thymidine, Uridine or Leucine", Curr. Top Rad. Res. Quart., vol. 12, 1977, pp. 225-254.
Michie et al., "Lifespan of Human Lymphocyte Subsets Defined by CD45 Isoforms,", Nature, vol. 360, 1992, pp. 264-265.
Mikkola et al., "Serum Cholesterol Efflux Potential is an Independent Predictor of Coronary Artery Atherosclerosis", Atherosclerosis, vol. 170, 2003, pp. 31-38.
Mindham et al., "Application of Simultaneous Spleen and Liver Perfusion to the Study of Reverse Cholesterol Transport", Biochemical Journal, vol. 302, 1994, pp. 207-213.
Misell et al., "A new in Vivo Stable Isotope Method for Measuring Mammary Epithelial Cell Proliferation", Faseb Journal Experimental Biology, vol. 14, No. 4, 2000, p. 550.
Mohri et al., "Increased Turnover of T Lymphocytes in HIV-1 Infection and its Reduction by Antiretroviral Therapy", J. Exp. Med., vol. 194, No. 9, 2001, pp. 1277-1287.
Morris et al., "Evidence that a Slowly Cycling Subpopulation of Adult Murine Epidermal Cells Retains Carcinogen", Cancer Research, vol. 46, 1997, pp. 3061-3066.
Morris et al., "Evidence that Cutaneous Carcinogen-Initiated Epithelial Cells from Mice are Quiescent Rather than Actively Cycling", Cancer Research, vol. 57, 1997, pp. 3436-3443.

(56) References Cited

OTHER PUBLICATIONS

Morsches et al., "Tierexperimentelle Untersuchungen Uber Die Beziehungen Zwischen Der Hydroxyprolinausscheidung Im Urin Und Den Hydroxyprolinfraktionen Im Serum", Der Hautarzt, vol. 27, 1976, pp. 234-242.

Mosier, D. E., "CD4.sup.+ Cell Turnover", Nature, vol. 375, 1995, pp. 193-194.

Murali-Krishna et al., "Counting Antigen-Specific CD8 T Cells: A Reevaluation of Bystander Activation during Viral Infection", Immunity, vol. 8, 1998, pp. 177-187.

Nagasaka et al., "Endogenous Glucose Production and Glucose Effectiveness in Type 2 Diabetic Subjects Derived From Stable-Labeled Minimal Modal Approach", Diabetes, vol. 48, May 1999, pp. 1054-1056.

Naik et al., "Pharmacological Activation of Liver X Receptors Promotes Reverse Cholesterol Transport In Vivo", Circulation, vol. 113, 2006, pp. 90-97.

Nanjee et al., "Intravenous apoA-1/lecithin Discs Increase Pre-Beta-HDL Concentration in Tissue Fluid and Stimulate Reverse Cholesterol Transport in Humans", Journal of Lipid Research, vol. 42, 2001, pp. 1586-1593.

Neese et al., "Advances in the Stable Isotope-Mass Spectrometric Measurement of DNA Synthesis and Cell Proliferation", Analytical Biochemistry, vol. 298, No. 2, 2001, pp. 189-195.

Neese et al., "Gluconeogenesis and Intrahepatic Triose Phosphate Flux in Response to Fasting or Substrate Loads", Journal of Biological Chemistry, vol. 270, No. 24, 1995, pp. 14452-14463.

Neese et al., "Measurement of Endogenous Synthesis of Plasma Cholesterol in Rats and Humans Using MIDA", Am. J. Physiol., vol. 264, 1993, pp. E139-E147.

Neese et al., "Measurement in Vivo of Proliferation Rates of Slow Turnover Cells by 2H2O Labeling of the Deoxyribose Moiety of DNA", Proceedings of the National Academy of Sciences, vol. 99, No. 24, Nov. 26, 2002, pp. 15345-15350.

Ong et al., "Stable Isotope Labeling by Amino Acids in Cell Culture, SILAC, as a Simple and Accurate Approach to Expression Proteomics", Molecular and Cellular Proteomics, vol. 1, 2002, pp. 376-386.

Oshima et al., "COX Selectivity and Animal Models for Colon Cancer", Current Pharmaceutical Design, vol. 8, 2002, pp. 1021-1034.

Ouguerram et al., "A New Labeling Approach Using Stable Isotopes to Study In Vivo Plasma Cholesterol Metabolism in Humans", Metabolism, vol. 51, No. 1, Jan. 2002, pp. 5-11.

Oyaizu et al., "Role of Apoptosis in HIV Disease Pathogenesis", J. of Clinical Immunology, vol. 15, No. 5, 1995, pp. 217-231.

Paku, S. "Origin and Structural Evolution of the Early Proliferating Oval Cells in Rat Liver", American Journal of Pathology, vol. 158, No. 4, Apr. 2001, pp. 1313-1323.

Palmer et al., "Telomere Length, Telomerase Activity, and Replicative Potential in HIV Infection: Analysis of CD4+ and CD8+ T Cells from HIV-discordant Monozygotic Twins", J. Experimental Medicine, vol. 185, No. 7, 1997, pp. 1381-1386.

Panteleo, Giuseppe, "Unraveling the Strands of HIV's Web", Nature Medicine, vol. 5, No. 1, 1999, pp. 27-28.

Papageorgopoulos et al., "Measuring Protein Synthesis by Mass Isotopomer Distribution Analysis (MIDA)", Analytical Biochemistry, vol. 267, 1999, pp. 1-16.

Papageorgopoulos et al., "Toward the Measurement of Protein Synthesis by Mass Isotopomer Distribution Analysis (MIDA):Resolution of Isotopomers in a [d.sub.3]-Leucine Enriched Synthetic Oligopeptide Using Electrospray/Quadrupole Mass Spectrometry (ESI/MS)",Federation of American Societies for Experimental Biology, vol. 1022, 1993, p. A177.

Park et al., "Measurement of Small Intestinal Cell Turnover with [6,6, 2H2] Glucose", Berkeley Scientific, Abstract, vol. 1, No. 2, 1997, pp. 41-43.

Parks et al., "Carbohydrate-induced Hypertriacylglycerolemia: Historical Perspective and Review of Biological Mechanisms", Am. J. Nutr., vol. 71, 2000, pp. 412-433.

Parks et al., "Dependence of Plasma a-Tocopherol Flux on Very Low-Density Triglyceride Clearance in Humans", Free Radical Biology & Medicine, vol. 29, No. 11, 2000, pp. 1151-1159.

Parks et al., "Effects of a Low-Fat, High-Carbohydrate Diet on VLDL-Triglyceride Assembly, Production, and Clearance", J. Clin. Invest. vol. 104, No. 8, 1999, pp. 1087-1096.

Paša-Tolic et al., "High Throughput Proteome-Wide Precision Measurements of Protein expression Using Mass Spectrometry", J. Am. Chem. Soc., vol. 121, 1999, pp. 7949-7950.

Patsalos et al., "Pattern of Myelin Breakdown During Sciatic Nerve Wallerian Degeneration: Reversal of the Order of Assembly", The Journal of Cell Biology, vol. 87, 1980, pp. 1-5.

Patterson et al., "Concentration Dependence of Methyl-Palmitate Isotope Ratios by Electron Impact Ionization Gas Chromatography/Mass Spectrometry", Biol. Mass Spectrom., vol. 22, 1993, pp. 481-486.

Patterson et al., "Measurement of Very Low Stable Isotope Enrichments by Gas Chromatography/Mass Spectrometry: Application to Measurement of Muscle Protein Synthesis", Metabolism, vol. 46, No. 8, Aug. 1997, pp. 943-948.

Patton et al., "Measurements of Fatty Acid Synthesis by Incorporation of Deuterium from Deuterated Water", Biochemistry, vol. 18, No. 14, 1979, pp. 3186-3188.

Perelson et al., "Decay Characteristics of HIV-1-Infected Compartments During Combination Therapy", Nature 387, 1997, pp. 188-191.

Perelson et al., "HIV-1 Dynamics in Vivo: Virion Clearance Rate, Infected Cell Life-Span, and Viral Generation Time", Science, vol. 271, 1996, pp. 1582-1586.

Perochon et al., "Radiolabeling of the Lipids of Chinese Hamster Ovary Cells with the Probe [3-(Trifluoromethyl)-3-(m-[125]iodophenyl)diazirine", Analytical Biochemistry, vol. 254, 1997, pp. 109-118.

Previs et al., "Estimation of Protein Turnover In Vivo Using D2O", Diabetes Abstract Book, 61st Scientific Sessions, vol. 50, Supplement 2, A301, 2001, 1248-p.

Propper et al., "Use of Positron Emission Tomography in Pharmacokinetic Studies to Investigate Therapeutic Advantage in a Phase I Study of 120-Hour Intravenous Infusion XR5000", Journal of Clinical Oncology, vol. 21, No. 2, Jan. 2003, pp. 203-210.

Ramakers et al., "Chronic Suppression of Bioelectric Activity and Cell Survival in Primary Cultures of Rat Cerebral Cortex Biochemical Observations", European Journal of Neuroscience, vol. 3, No. 2, 1991, pp. 154-161.

Ravichandran et al., "In Vivo Labeling Studies on the Biosynthesis and Degradation of Collagen in Experimental Myocardial Infarction", Biochemistry Journal, vol. 24, No. 3, 1991, pp. 405-414.

Reichard, P., "From Deoxynucleotides to DNA Synthesis", Federation Proceedings, vol. 37, No. 1, 1978, pp. 9-14.

Reichard, P., "Interactions Between Deoxyribonucleotide and DNA Synthesis", Ann. Rev. Biochem. vol. 57, 1988, pp. 349-374.

Greving et al., "Nanostructure-Initiator Mass Spectrometry Metabolite Analysis and Imaging", Analytical Chemistry, vol. 83, No. 1, Jan. 1, 2011, pp. 2-7.

Reindl et al., "Multivariate analysis of a 3D mass spectral image for examining tissue heterogeneity", Integrative Biology, vol. 3, Apr. 3, 2011, pp. 460-467.

Office Action received for Japanese Patent Application No. 2014-529925, dated Jul. 5, 2016, 9 pages (6 pages of English Translation and 3 pages of Official Copy).

Final Office Action received for U.S. Appl. No. 11/416,842 dated Jun. 16, 2015, 16 pages.

Extended European Search Report received for European Application No. 12855131.4, dated Mar. 18, 2015, 8 pages.

Notice of Allowance received for U.S. Appl. No. 14/210,415, dated May 15, 2015, 6 pages.

International Search Report received for PCT Patent Application No. PCT/US2014/028931, dated Jul. 21, 2014, 5 pages.

Hughes, et al., "Developments in Quantitative Mass Spectrometry for the Analysis of Proteome Dynamics", Trends in Biotechnology, vol. 30, No. 12, Dec. 2012, pp. 668-676.

(56) References Cited

OTHER PUBLICATIONS

Lu, et al., "SILAM for Quantitative Proteomics of Liver Akt1/PKBα after Burn Injury", International Journal of Molecular Medicine, vol. 29, No. 3, Mar. 2012, pp. 461-471.

Lukaski, Henry C., "Methods for the assessment of human body composition: traditional and new", The American Journal of Clinical Nutrition, vol. 46, No. 4, Jan. 1, 1987, pp. 537-556.

Quintao et al., "An Evaluation of Four Methods for Measuring Cholesterol Absorption by the Intestine in Man", Journal of Lipid Research, vol. 12, 1971, pp. 221-232.

Robinson, et al., "D20 to Determine Muscle Protein Synthesis Rates in Response to Post-Exercise Nutrition in Adults", Faseb Journal. Fed. of American Soc. For Experimental Biology, vol. 24,, Apr. 2010, 1 page.

Notice of Allowance received for Canadian Patent Application No. 2,475,924, dated Sep. 17, 2015, 1 page.

Extended European Search Report (includes Supplementary European Search Report and Search Opinion) received for European Patent Application No. 12830717.0, dated Jan. 30, 2015, 8 pages.

International Written Opinion received for PCT Patent Application No. PCT/US2012/068068, dated Feb. 8, 2013, 5 pages.

Turner et al., "Dissociation between Adipose Tissue Fluxes and Lipogenic Gene Expression in ob/ob Mice", Am. J. Physiol. Endocrinol. Metab., vol. 292, 2006, pp. E1101-E1109.

Rittenberg et al., "Deuterium as an Indicator in the Study of Intermediary Metabolism—VIII. Hydrogenation of Fatty Acids in the Animal Organism", Journal of Biological Chemistry, vol. 117, Feb. 1937, pp. 485-490.

Rittenberg et al., "Deuterium as an Indicator in the Study of Intermediary Metabolism—X. The Metabolism of Butyric and Caproic Acids", Journal of Biological Chemistry, vol. 120, Sep. 1937, pp. 503-510.

Rittler et al., "Effect of Tumor Removal on Mucosal Protein Synthesis in Patients with Colorectal Cancer", American Journal of Physiology—Endocrinology and Metabolism, vol. 284, 2003, pp. E1018-E1021.

Roberts, S. B., "Use of the Doubly Labeled Water Method for Measurement of Energy Expenditure, Total Body Water, Water Intake, and Metabolizable Energy Intake in Humans and Small Animals", Can. J. Physiol. Pharmacol., vol. 67, No. 10, 1989, pp. 1190-1198.

Robin et al., "Mitochondria DNA Molecules and Virtual Number of Mitochondria per Cell in Mammalian Cells", Journal of Cellular Physiology, vol. 136, 1988, pp. 507-513.

Robosky, L. C., "In Vivo Toxicity Screening Programs Using Metabonomics", Combinatorial Chemistry & High Throughput Screening., vol. 5, 2002, pp. 651-662.

Rocha et al., "Accumulation of Bromodeoxyuridine-Labelled Cells in Central and Peripheral Lymphoid Organs: Minimal Estimates of Production and Turnover Rates of Mature Lymphocytes", Eur. J. Immunol., vol. 20, 1990, pp. 1697-1708.

Roda et al., "Results with Six 'Kit' Radioimmunoassays for Primary Bile Acids in Human Serum Intercompared", Clin. Chem., vol. 26, No. 12, 1980, pp. 1677-1682.

Roederer, M., "T-Cell Dynamics of Immunodeficiency", Nature Medicine, vol. 1, No. 7, Jul. 1995, pp. 621-622.

Rooyackers et al., "Tracer Kinetics Are of Limited Value to Measure In Vivo Protein Synthesis and Degradation Rates in Muscle of Anesthetized Rats", Metabolism, vol. 45, No. 10, Oct. 1996, pp. 1279-1283.

Rosin et al., "The Use of Exfoliative Cell Samples to Map Clonal Genetic Alterations in the Oral Epithelium of High-Risk Patients", Cancer Research, vol. 57, Dec. 1, 1997, pp. 5258-5260.

Royale et al., "Techniques for Investigating Substrate Metabolism in Patients", Annals of the Royal College of Surgeons of England, vol. 63, 1981, pp. 415-419.

Santarelli et al., "Requirement of Hippocampal Neurogenesis for the Behavioral Effects of Antidepressants", Science, vol. 301, No. 5634, Aug. 8, 2003, pp. 805-809.

Sawada et al., "Comparison of Autoradiography, Liquid Scintillation Counting and Immunoenzymatic Staining of 5-bromo-2'-deoxyuridine for Measurement of Unscheduled DNA Synthesis and Replicative DNA Synthesis in Rat Liver", Mutation Research, vol. 344, 1995, pp. 109-116.

Scalise, K., "Tracking T-Cells in AIDS Patients: A Safe Reliable Method of Measuring Human Cell Generation Rates", Berkeleyan, Feb. 11-17, 1998, 3 pages.

Scheibner et al., "Bile Acid Synthesis from Newly Synthesized Vs. Preformed Cholesterol Precursor Pools in the Rat", Hepatology, vol. 17, 1993, pp. 1095-1102.

Scheibner et al., "Complex Feedback Regulation of Bile Acid Synthesis in the Hamster: The Role of Newly Synthsized Cholesterol", Hepatology, vol. 30, 1999, pp. 230-237.

Schneiter et al., "Kinetics of Dexamethasone Induced Alterations of Glucose Metabolism in Healthy Humans", American Journal of Physiology, 1998, pp. E806-E813.

Schoenheimer et al., "Deuterium as an Indicator in the Study of Intermediary Metabolism—V. The Desaturation of Fatty Acids in Organism", Journal of Biological Chemistry, vol. 113, Mar. 1936, pp. 505-510.

Schwarz et al., "Short-Term Alterations in Carbohydrate Energy Intake in Humans", J. Clin. Invest., vol. 96, 1995, pp. 2735-2743.

Australian Patent Office Search Report dated Aug. 26, 2005, for Singapore patent application No. SG 200500571-5, filed Jul. 25, 2003, 5 pages.

Shevchenko et al., "Rapid 'de Novo' Peptide Sequencing by a Combination of Nanoelectrospray, Isotopic Labeling and a Quadrupole/Time-of-flight Mass Spectrometer", Rapid Commun. Mass Spectrom., vol. 11, 1997, pp. 1015-1024.

Shigenaga et al., "Assays of Oxidative DNA Damage Biomarkers 8-Oxo-2'-deoxyguanosine and 8-Oxoguanine in Nuclear DNA and Biological Fluids by High-Performance Liquid Chromatography with Electrochemical Detection", Methods in Enzymology, vol. 234, 1994, pp. 16-33.

Siler et al., "De Novo Lipogenesis, Lipid Kinetics, and Whole-Body Lipid Balances in Humans after Acute Alcohol Consumption1-3", American Journal of Clinical Nutrition, vol. 70, 1999, pp. 928-936.

Siler et al., "The Inhibition of Gluconeogenesis Following Alcohol in Humans", Am. J. Physiol., vol. 275, 1998, pp. E897-E907.

Siler et al., "VLDL-Triglyceride Production After Alcohol Ingestion, Studied Using [2-13C1] Glycerol", J. Lipid Res., vol. 39, 1998, pp. 2319-2328.

Smith et al., "The Phosphogluconate Odixative Pathway", in Principles of Biochemistry, 7th edition, McGraw-Hill Book Company, 1983, pp. 417-423.

Sosa-Peinado et al., "Overexpression and Biosynthetic Deuterium Enrichment of TEM-1 Beta-Lactamase for Structural Characterization by Magnetic Resonance Methods", Protein Expression and Purification, vol. 19, No. 2, Jul. 2000, pp. 235-245.

Sprent et al., "CD4+ Cell Turnover", Nature, vol. 375, 1995, 194 pages.

Stingl et al., "Purification and Unique Properties of Mammary Epithelial Stem Cells", Nature, vol. 439, Feb. 2006, pp. 993-997.

Stingl et al., "Characterization of Bipotent Mammary Epithelial Progenitor Cells in Normal Adult Human Breast Tissue", Breast Can Res and Treatment, vol. 67, 2001, pp. 93-109.

Sunter et al., "Cell Population Kinetics in the Epithelium of the Colon of the Male Rat", Virchows Archiv. B Cell Path., vol. 26, 1978, pp. 275-287.

Teixeira et al., "Poor CD4 T Cell Restoration After Supression of HIV-1 Replication May Reflect Lower Thymic Function", AIDS, vol. 15, No. 14, 2001, pp. 1749-1756.

Tint et al., "Transformation of 5α-cholest-7-en-3β-ol to Cholesterol and Cholestanol in Cerebrotendinous Xanthomatosis", Journal of Lipid Research, vol. 15, 1974, pp. 256-262.

Traber et al., "Isolation of Intestinal Epithelial Cells for the Study of Differential Gene Expression Along the Crypt-Villus Axis", Am. J. Physiol., vol. 260, 1991, pp. G895-G903.

Trappe et al., "Effect of Ibuprofen and Acetaminophen on Postexercise Muscle Protein Synthesis", Am J Physiology Endocronol Metab, vol. 282, 2002, pp. E551-E556.

(56) References Cited

OTHER PUBLICATIONS

Turner, S. M., "Stable Isotopes, Mass Spectrometry, and Molecular Fluxes: Applications to Toxicology", Journal of Pharmacological and Toxicological Methods, vol. 53, 2006, pp. 75-85.
Turner et al., "Emerging Applications of Kinetic Biomarkers in Preclinical and Clinical Drug Development", Current Opinion in Drug Discovery & Development, vol. 8, No. 1, 2005, pp. 115-126.
Turner et al., "Measurement of Triglyceride (TG) Synthesis in Vivo 2H2O Incorporation into TG-Glycerol and Application of Mass Isotopomer Distribution Analysis (MIDA)", Experimental Biology, 2002 16 [Meeting Abstract 361.9], A400.
Van Hinsbergh et al., "Palmitate Oxidation by Rat Skeletal Muscle Mitochondria", Archives of Biochemistry and Biophysics, vol. 190, No. 2, 1978, pp. 762-771.
Van Loan et al., "Monitoring Changes in Fat-Free Mass in HIV-Positive Men with Hypotestosteronemia and AIDS Wasting Syndrome Treated with Gonadal Hormone Replacement Therapy", AIDS, vol. 13, 1999, pp. 241-248.
Veenstra et al., "Proteome Analysis Using Selective Incorporation of Isotopically Labeled Amino Acids", J. Am. Soc. Mass. Spectrom., vol. 11, 2000, pp. 78-82.
Veerkamp et al., "14CO2 Production is no Adequate Measure of [14C]Fatty Acid Oxidation", Biochemical Medicine and Metabolic Biology, vol. 35, 1986, pp. 248-259.
Véniant et al., "Defining the Atherogenicity of Large and Small Lipoproteins Containing Apolipoproteins B100", J. Clin. Invest., vol. 106, No. 12, 2000, pp. 1501-1510.
Wadke et al., "Fatty Acid Synthesis by Liver Perfused with Deuterated and Tritiated Water", Biochemistry, vol. 12, No. 14, 1973, pp. 2619-2624.
Wain-Hobson, S., "Virological Mayhem", Nature, vol. 373, 1995, 102 pages.
Waldeman et al., "A Comparison Between Bromodeoxyuridine and 3 H Thymidine Labeling in Human Breast Tumors", Modern Path., vol. 4, No. 6, 1991, pp. 718-722.
Wang et al., "Effects of Nicotinic Acid on Fatty Acid Kinetics, Fuel Selection, and Pathways of Glucose Production in Women", Am. J. Physiol. Endocrinol. Metab., vol. 279, 2000, pp. E50-E59.
Waterlow, J. C., "Protein Turnover in the Whole Animal", Invest. Cell Pathol. vol. 3, 1980, pp. 107-119.
Wei et al., "Viral Dynamics in Human Immunodeficiency Virus Type 1 Infection", Nature, vol. 373, 1995, pp. 117-122.
Eriksson et al., "Stimulation of Fecal Steroid Excretion After Infusion of Recombinant Proapolipoprotein A-1: Potential Reverse Cholesterol Transport in Humans", Circulation, vol. 100, 1999, pp. 594-598.
International Preliminary Report on Patentability received for PCT Patent Application No. PCT/US2012/054329, dated Mar. 20, 2014, 11 pages.
International Search Report and Written Opinion received for PCT Patent Application No. PCT/US2012/054329, dated Dec. 7, 2012, 13 pages.
International Preliminary Report on Patentability received for PCT Patent Application No. PCT/US2012/068068, dated Jun. 19, 2014, 7 pages.
International Search Report received for PCT Patent Application No. PCT/US2012/068068, dated Feb. 8, 2013, 3 pages.
International Search Report & Written Opinion received for PCT Patent Application No. PCT/US2014/042186, dated Oct. 1, 2014, 10 pages.
Carling et al., "Simultaneous Determination of Guanidinoacetate, Creatine and Creatinine in Urine and Plasma by Un-Derivatized Liquid Chromatography-Tandem Mass Spectrometry", Annals of Clinical Biochemistry, vol. 45, 2008, pp. 575-584.
Clark et al., "Total Body Skeletal Muscle Mass: Estimation by Creatine (methyl-d3) Dilution in Humans.", Journal of Applied Physiology, vol. 116, No. 12, Jun. 15, 2014, pp. 1605-1613.
Heymsfield et al., "Measurement of Muscle Mass in Humans: Validity of the 24-hour Urinary Creatinine Method", American Journal of Clinical Nutrition, vol. 37, Mar. 1983, pp. 478-494.

Kreisberg et al., "Measurement of Muscle Mass in Humans by Isotopic Dilution of Creatine-14C", Journal of Applied Physiology, vol. 28, No. 3, Mar. 1970, pp. 264-267.
Mussini et al., "Determination of Creatine in Body Fluids and Muscle", Journal of Chromatography Biomedical Applications, vol. 305, 1984, pp. 450-455.
Picou et al., "The Measurement of Muscle Mass in Children Using [15N] Creatine", Pediatric Research, vol. 10, 1976, pp. 184-188.
Poortmans et al., "Estimation of Total-Body Skeletal Muscle Mass in Children and Adolescents", Medicine & Science in Sports & Exercise, vol. 37, 2005, pp. 316-322.
Reeds et al., "Muscle Mass and Composition in Malnourished Infants and Children and Changes Seen after Recovery", Pediatric Research, vol. 12, 1978, pp. 613-618.
Schutte et al., "Total Plasma Creatinine: An Accurate Measure of Total Striated Muscle Mass", The American Physiological Society, vol. 51, 1981, pp. 762-766.
Smith-Palmer, Truis, "Separation Methods Applicable to Urinary Creatine and Creatinine", Journal of Chromatography B, vol. 781, 2002, pp. 93-106.
Stimpson, et al., "Longitudinal changes in total body creatine pool size and skeletal muscle mass using the D3-creatine dilution method", Journal of Cachexia, Sarcopenia and Muscle, vol. 4, No. 3, Jun. 25, 2013, pp. 217-223.
Stimpson et al., "Longitudinal Determination of Total Body Creatine Pool Size and Skeletal Muscle Mass in Rats by D3-Creatine Dilution", The FASEB Journal, vol. 27, Apr. 1, 2013, p. lb410.
Stimpson et al., "Total-Body Creatine Pool Size and Skeletal Muscle Mass Determination by Creatine-(methyl-d3) Dilution in Rats", Journal of Applied Physiology, vol. 112, No. 11, Mar. 15, 2012, pp. 1940-1948.
Wang et al., "Total-Body Skeletal Muscle Mass: Evaluation of 24-h Urinary Creatinine Excretion by Computerized Axial Tomography", American Society for Clinical Nutrition, vol. 63, 1996, pp. 863-869.
Wang et al., "Urinary Creatinine-Skeletal Muscle Mass Method: A Prediction Equation Based on Computerized Axial Tomography1-3", Biomedical and Environmental Sciences, vol. 9, 1996, pp. 185-190.
Welle et al., "Utility of Creatinine Excretion in Body-Composition Studies of Healthy Man and Women Older than 60 y1-3", The American Journal of Clinical Nutrition, vol. 63, Feb. 1996, pp. 151-156.
Wells et al., "Body Composition by 2H Dilution in Gambian Infants: Comparison with UK Infants and Evaluation of Simple Prediction Methods", The British Journal of Nutrition, vol. 102, 2009, pp. 1776-1782.
Abramson Hanley N., "The Lipogenesis Pathway as a Cancer Target", Journal of Medicinal Chemistry, vol. 54, 2011, pp. 5615-5638.
Ackerstaff et al., "Choline Phospholipid Metabolism: A Target in Cancer Cells?", Journal of Cellular Biochemistry, vol. 90, Issue 3, Oct. 2003, pp. 525-533.
Baran et al., "Mass Spectrometry based Metabolomics and Enzymatic Assays for Functional Genomics", Current Opinion in Microbiology, vol. 12, No. 5, 2009, pp. 547-552.
Bartella et al., "Proton MR Spectroscopy with Choline Peak as Malignancy Marker Improves Positive Predictive Value for Breast Cancer Diagnosis: Preliminary Study", Radiology, vol. 239, No. 3, Jun. 2006, pp. 686-692.
Bertos et al., "Breast Cancer—One Term, Many Entities?", The Journal of Clinical Investigation, vol. 121, No. 10, 2011, pp. 3789-3796.
Bougnoux et al., "Fatty Acids and Breast Cancer: Sensitization to Treatments and Prevention of Metastatic Re-Growth", Progress Lipid Research, vol. 49, Issue 1, Jan. 2010, pp. 76-86.
Bowen et al., "Dealing with the Unknown: Metabolomics and Metabolite Atlases", Journal of American Society of Mass Spectrometry, vol. 21, 2010, pp. 1471-1476.
Busch et al., "Measurement of Protein Turnover Rates by Heavy Water Labeling of Nonessential Amino Acids", Biochimica et Biophysica Acta, vol. 1760, 2006, pp. 730-744.

(56) References Cited

OTHER PUBLICATIONS

Chen et al., "Application of Probe Electrospray to Direct Ambient Analysis of Biological Samples", Rapid Commun Mass Spectrom, vol. 22, No. 15, Aug. 2008, pp. 2366-2374.

Cichon et al., "Microenvironmental Influences that Drive Progression from Benign Breast Disease to Invasive Breast Cancer", J. Mammary Gland Biol Neoplasia, vol. 15, Dec. 2010, pp. 389-397.

Commerford et al., "The Distribution of Tritium Among the Amino Acids of Proteins Obtained from Mice Exposed to Tritiated Water", Radiation Research, vol. 94, 1983, pp. 151-155.

Cornett et al., "MALDI Imaging Mass Spectrometry: Molecular Snapshots of Biochemical Systems", Nature Methods, vol. 4, No. 10, 2007, pp. 828-833.

Deberardinis et al., "Brick by Brick: Metabolism and Tumor Cell Growth", Current Opinion in Genetics & Development, vol. 18, No. 1, Feb. 2008, pp. 54-61.

Deberardinis et al., "The Biology of Cancer: Metabolic Reprogramming Fuels Cell Growth and Proliferation", Cell Metabolism, vol. 7, Jan. 2008, pp. 11-20.

Deeb et al., "Identification of an Integrated SV40 Tit-antigen Cancer Signature in Gressive Human Breast, Prostate, and Lung Carcinomas with Poor Prognosis", Cancer Research, vol. 67 No. 17, 2007, pp. 8065-8080.

Diraison et al., "In Vivo Measurement of Plasma Cholesterol and Fatty Acid Synthesis with Deuterated Water: Determination of the Average Number of Deuterium Atoms Incorporated. Metabolism", Metabolism: Clinical and Experimental, vol. 45, Issue 7, Jul. 1996, pp. 817-821.

Dowsett et al., "Assessment of Ki67 in Breast Cancer: Recommendations From The International Ki67 in Breast Cancer Working Group", Journal of the National Cancer Institute, vol. 103, 2011, pp. 1656-1664.

Gerlinger et al., "Intratumor Heterogeneity and Branched Evolution Revealed by Multiregion Sequencing", The New England Journal of Medicine, vol. 366, No. 10, 2012, pp. 883-892.

Green et al., "The C3(1)/SV40 T-Antigen Transgenic Mouse Model of Mammary Cancer: Ductal Epithelial Cell Targeting with Multistage Progression to Carcinoma", Oncogene, vol. 19, 2000, pp. 1020-1027.

Guillermet-Guibert et al., "Targeting the Sphingolipid Metabolism to Defeat Pancreatic Cancer Cell Resistance to the Chemotherapeutic Gemcitabine Drug", Molecular Cancer Therapeutics, vol. 8, No. 4, Apr. 2009, pp. 809-821.

Hanahan et al., "Hallmarks of Cancer: the Next Generation", Cell, vol. 144, No. 5, 2011, pp. 646-674.

Hankin et al., "The Relationship between MALDI IMS Intensity and Measured Quantity of Selected Phospholipids in Rat Brain Sections", Anal Chemistry, vol. 82, No. 20, 2010, pp. 8476-8484.

Hellerstein et al., "Measurement of De Novo Hepatic Lipogenesis in Humans Using Stable Isotopes", Journal of Clinical Investigation, vol. 87, May 1991, pp. 1841-1852.

Herschkowitz et al., "The Functional Loss of the Retinoblastoma Tumour Suppressor is a Common Event in Basal-Like and Luminal B Breast Carcinomas", Breast Cancer Research, vol. 10, No. 5, Sep. 2008, 13 pages.

Hilvo et al., "Novel Theranostic Opportunities Offered by Characterization of Altered Membrane Lipid Metabolism in Breast Cancer Progression", Cancer Research, vol. 71, 2011, pp. 3236-3245.

Hsu et al., "Cancer Cell Metabolism: Warburg and Beyond", Cell, vol. 134, Sep. 5, 2008, pp. 703-707.

Igal, R. Ariel., "Stearoyl-CoA Desaturase-1: A Novel Key Player in the Mechanisms of Cell Proliferation, Programmed Cell Death and Transformation to Cancer", Carcinogenesis, vol. 31, No. 9, 2010, pp. 1509-1515.

Yarris, L. (2010). "Two Berkeley Lab Scientists Win PECASE Award," retrieved Mar. 4, 2019 from the internet, https://newscenter.lbl.gov/2010/11/08/2009-pecase/, 3 pages.

\* cited by examiner

H&E Stain Serial Section

Flux m/z: 842.5

Flux m/z 844.5

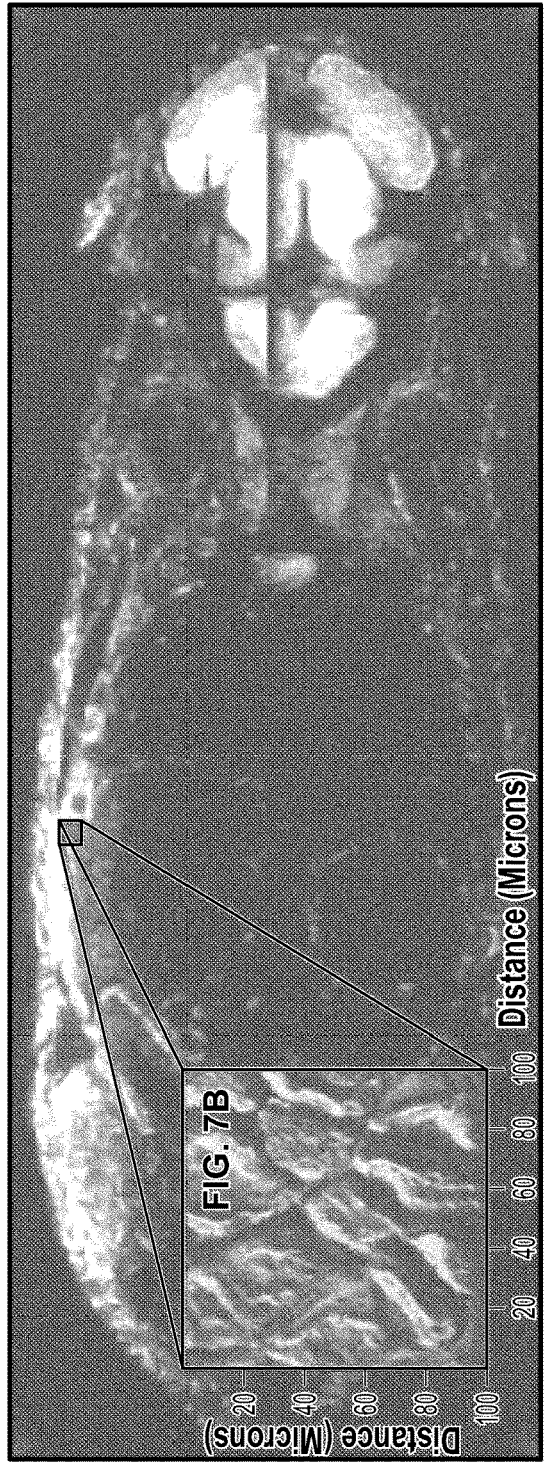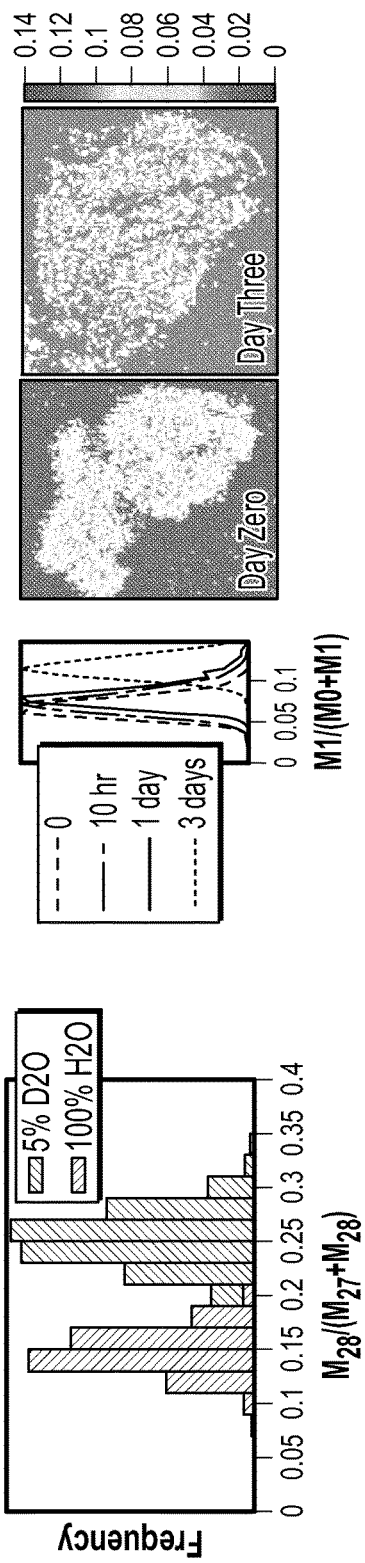
FIG. 7A
FIG. 7B
FIG. 7C
FIG. 7D

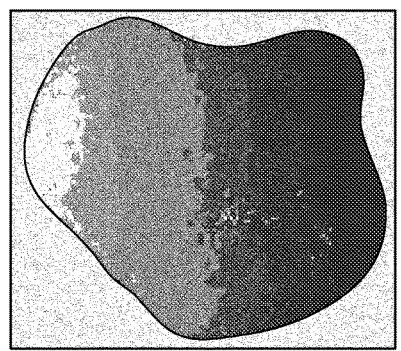 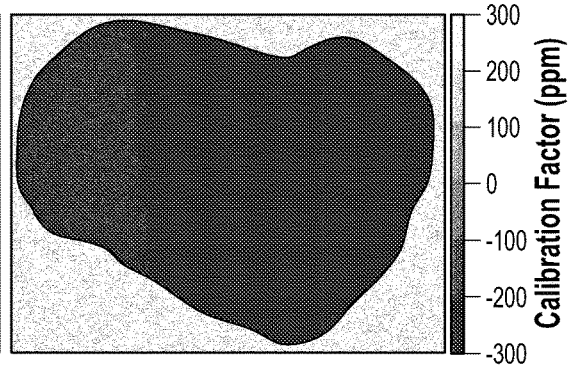
FIG. 12A             FIG. 12B
F1: Isotopic Pattern Given by a Chemical Formula and the Natural Isotopic Abundance of Elements
F2: Isotopic Pattern Given by a Chemical Formula with a Defined Number of Hydrogens which can be Enriched
Measured Spectra: Depends on the Relative Amount of the Two Patterns, F1 & F2
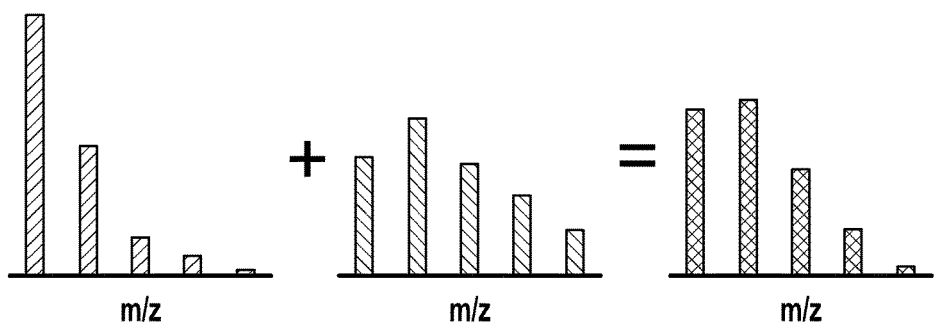
FIG. 13

METABOLIC FLUX MEASUREMENT, IMAGING AND MICROSCOPY

CROSS-REFERENCE TO RELATED APPLICATIONS

This is a U.S. National Phase patent application of PCT/US2012/054329, filed Sep. 7, 2012, which claims the benefit of U.S. Provisional Patent Application No. 61/532,522, filed Sep. 8, 2011, each of which is incorporated herein by reference in its entirety.

ACKNOWLEDGMENT OF GOVERNMENT SUPPORT

This invention was made with Government support under Grant No. CA112970 awarded by the National Institutes of Health and with Government support under Grant No. DEAC02-05CH11231, awarded by the Department of Energy. The government has certain rights in the invention.

BACKGROUND

1. Field

The present disclosure relates generally to the fields of metabolic flux determination, microscopy and functional histopathology, and more specifically to in situ spatial imaging, mapping and display of dynamic metabolic processes in histopathology specimens.

2. Related Art

Breast cancer development involves dynamic and reciprocal interactions between neoplastic cells, activated stromal cells, extracellular matrix (ECM) and soluble molecules in their vicinity. Together these environmental factors foster the malignant phenotype. Intertwined with these hallmarks of cancer development is the fact that tumor cells metabolize glucose largely via aerobic glycolysis as opposed to oxidative phosphorylation, and produce lactate in a less energy-efficient manner, i.e., the Warburg effect [1]. This distinct metabolic state is common to most solid tumors, including breast cancers, and is thought to contribute to their chemoresistance. Thus altered metabolism may limit efficacy of standard anti-cancer therapy, but this feature may also be used to identify and characterize subtypes of neoplastic tissue.

Altered metabolic flux is critical to the malignant phenotype. The dependence on aerobic glycolysis and intimate linkage between Raf/MEK/ERK, PI3K/Akt pathway[2, 3], and microenvironment suggest strong causal relationships between these signaling networks, drug resistance, metabolite transport, microenvironment, and metabolism. Hence, altered metabolism can provide a mechanism to support a proliferative phenotype through aerobic glycolysis, drive evolution, and drug resistance through dormancy and altered lipid metabolism. For example, it has recently been suggested that aerobic glycolysis provides metabolic precursors necessary for rapid growth (i.e. membrane biosynthesis)[4].

Significant progress has been made in applying molecular profiling to characterize cancer phenotype. Transcriptomic profiles have been identified that predict prognosis or response to treatment for cancers[5] including alterations in cancer metabolism[6]. In fact cancer cells exhibit a wide variety of abnormalities in metabolic fluxes [7], including numerous alterations in the synthesis and turnover of lipids [8] which are required to support the malignant phenotype through structural roles in membranes (e.g., cholesterol, phospholipids), signaling pathways (e.g., prostanoids, glycolipids) and mediation of pathways and organelle function (e.g. ER transport, mitochondrial biogenesis). However, tumors are often comprised of heterogeneous cell populations and therefore lipid turnover must be studied using imaging approaches to capture critical information on cellular sub-populations and microenvironmental effects.

Pathological techniques have always been critical in the diagnosis and treatment of cancer. Classic morphologic criteria, based on vital dyes and light microscopy, have been complemented by immunohistochemistry and gene expression profiling, leading to histological markers of growth factor receptor status or transcriptomic signatures, that, for example, predict an individual's likely treatment response [12]. However, all current histological analyses are 'blind' to the spatially ordered metabolic dynamics of the tumor. Metabolic fluxes are closer to function than static markers and may therefore correlate better with phenotypic behavior.

Metabolomic measurement provides direct information on downstream biochemical processes making this type of measurement an excellent complement to other systems or approaches focused on alterations in genetics and gene expression[13]. The two major technologies are Nuclear Magnetic Resonance (NMR or MR) and mass spectrometry (MS). These two approaches are complementary. NMR has the advantage that it allows real time non-invasive imaging using tracers and more recently using hyperpolarized molecules[14]. The sensitivity and dynamic range of mass spectrometry are many orders higher [15], making mass spectrometry a method of choice for untargeted studies that can feed into the development of NMR imaging studies. MS approaches coupled to chromatography maximize the number of metabolites detected and can quantify and identify (from MS/MS fragmentation patterns) with very high sensitivity from extremely complex mixtures[16]. However, the requisite sample homogenization and preparation results in a loss of spatial information, with averaging of metabolite concentrations, and loss of information of critical tumor subpopulations. Mass spectrometry based imaging has emerged to address this limitation[16] and the proposed work lays the groundwork for application all of the various technologies. Major approaches include: Time-of-Flight Secondary Ionization Mass Spectrometry (TOF-SIMS) [17, 18], which has the highest spatial resolution (~100 nm), but the extensive fragmentation which often complicates molecular characterization and the lack of tandem MS capabilities on commercial instruments limits identification. Matrix Assisted Laser Desorption Ionization (MALDI) [19] is a method of choice for intact protein imaging however metabolite imaging is complicated by matrix interference in the low mass range (<500 Da). The spatial resolution of MALDI corresponds to the matrix crystal size (typically ~50-75 um), but this can be reduced using special matrix deposition imaging approaches[20]. Recently, a new soft ionization and atmospheric pressure technique termed Desorption Electrospray Ionization (DESI) [21, 22] has emerged as an alternative approach to MALDI and SIMS. Unfortunately, tissue imaging by DESI shows relatively low spatial resolution (~100 um) and is currently incapable of imaging tissues at the cellular level.

BRIEF SUMMARY

The present disclosure provides methods for metabolic flux and kinetic measurement, imaging and microscopy. Provided herein are also the output generated from such methods, as well as systems and software generating such output involving the in situ spatial imaging, mapping and display of metabolic fluxes in samples.

In one aspect, provided is a method for generating an output representing in situ metabolic flux rates of a sample, wherein the sample is obtained from an individual to whom one or more isotope-labeled precursors have been administered for a period of time sufficient for one or more isotope labels to become incorporated into the individual. The method includes: a) determining one or more molecular flux rates of one or more molecules of interest in a first location of the sample by analyzing relative and absolute incorporation of the one or more isotope labels in the one or more molecules of interest in the first location of the sample, b) determining one or more molecular flux rates of the one or more molecules of interest in a second location of the sample by analyzing relative and absolute incorporation of the one or more isotope labels in the one or more molecules of interest in the second location of the sample, wherein the second location is different from the first location, wherein the first location and second location have a known spatial relationship, and wherein the relative and absolute incorporation of the one or more isotope labels in the one or more molecules of interest in the first location is independent of the relative and absolute incorporation of the one or more isotope labels in the one or more molecules of interest in the second location; and c) outputting the one or more molecular flux rates in the first location and in the second location, and information relating to the known spatial relationship between the first location and the second location.

In some embodiments, the method further includes mapping the one or more molecular flux rates to the first location and the second location of the sample before outputting the one or more molecular flux rates in the first location and in the second location. In some embodiments, at least one or more molecular flux rates in the first location is the same as at least one or more molecular flux rates in the second location. In other embodiments, at least one or more the molecular flux rates in the first location is different than one or more of the molecular flux rates in the second location.

In some embodiments, the isotope label is selected from $^{2}H$, $^{13}C$, $^{15}N$, $^{18}O$, $^{33}S$ and $^{34}S$. In one embodiment, the isotope label is $^{2}H$. In some embodiments, the isotope-labeled precursor is selected from isotope-labeled $H_2O$, isotope-labeled $CO_2$, isotope-labeled $NH_3$, isotope-labeled glucose, isotope-labeled lactate, and isotope-labeled $HCO_3$. In certain embodiments, the isotope-labeled precursor is selected from $^{2}H_2O$, $H_2{}^{18}O$, $^{13}CO_2$, $C^{18}O^{17}O$, $H^{16}CO_3$, $^{15}NH_3$, $^{2}H$-labeled amino acids, $^{13}C$-labeled amino acids, $^{15}N$-labeled amino acids, $^{18}O$-labeled amino acids, $^{34}S$-labeled amino acids, and $^{33}S$-labeled amino acids. In one embodiment, the isotope-labeled precursor is $^{2}H_2O$.

In some embodiments, the sample is obtained from an individual to whom the isotope-labeled precursor was administered orally. In certain embodiments, the individual is a human. In certain embodiments, the sample is urine, blood, or feces.

In some embodiments, the determining of the one or more molecular flux rates of the one or more molecules of interest in the first location and the second location of the sample employs mass isotopomer distribution analysis (MIDA) or spectral pattern isotope fitter (SPIF) analysis.

In some embodiments, the one or more molecular flux rates are output in the form of an image, a heat map, a contour map, a table or a database. In certain embodiments, the output is two-dimensional or three-dimensional. In some embodiments, the known spatial relationship between the first location and the second location is based on distance, cells, or cellular compartments.

Provided is also a method for generating an output representing in situ metabolic flux rates of a sample, by: a) administering one or more stable isotope-labeled precursors to a cell, tissue or organism for a period of time sufficient for one or more isotope labels to be incorporated into one or more molecules of interest in the cell, tissue or organism; b) obtaining a sample from the cell, tissue or organism; c) preparing a histopathologic slide from the sample; d) subjecting the histopathology slide to an energy-induced volatilization system, wherein the energy-induced volatilization system emits a focused beam of energy that scans across the sample to create a series of discrete packets or a continuous flow of ions in a first location and a second location of the sample, wherein the second location is different from the first location, wherein the first location and second location have a known spatial relationship, and wherein the relative and absolute incorporation of the one or more isotope labels in the one or more molecules of interest in the first location is independent of the relative and absolute incorporation of the one or more isotope labels in the one or more molecules of interest in the second location; e) directing the ions of the first location and the second location independently to a mass analyzer for mass spectrometry; f) measuring relative and absolute abundances of mass isotopomers within isotopomeric envelopes of ions from the one or more molecules of interest independently in the first location and the second location; g) comparing the relative and absolute abundances of the mass isotopomers in each isotopomeric envelope to natural abundances of the mass isotopomers to identify the molecular structure of the one or more molecules of interest; h) calculating the one or more molecular flux rates of the one or more molecules of interest, based on a change in pattern or relative abundances of mass isotopomers for each isotopomeric envelope of each molecule of interest; and i) mapping the one or more molecular flux rates to the first location and the second location of the sample.

In some embodiments, the method further includes displaying the one or more metabolic fluxes as an image, wherein the image has a first location and a second location, wherein the first location of the image has a pattern, a color, a number, or a combination thereof, representing the one or more molecular flux rates for the one or more molecules of interest in the first location of the sample; and wherein the second location of the image has a pattern, a color, a number representing the one or more molecular flux rates for the one or more molecules of interest in the second location of the sample.

In some embodiments, the one or more isotope labels are selected from the group consisting of $^{2}H$, $^{13}C$, $^{15}N$, $^{18}O$, $^{33}S$ and $^{34}S$. In one embodiment, the one or more isotope labels is one isotope label, wherein the one isotope label is $^{2}H$. In some embodiments, the one or more isotope-labeled precursors are selected from the group consisting of isotope-labeled $H_2O$, isotope-labeled $CO_2$, isotope-labeled $NH_3$, isotope-labeled glucose, isotope-labeled lactate, and isotope-labeled $HCO_3$. In other embodiments, the one or more isotope-labeled precursors are selected from the group consisting of $^{2}H_2O$, $H_2{}^{18}O$, $^{13}CO_2$, $C^{18}O^{17}O$, $H^{16}CO_3$, $^{15}NH_3$, $^{2}H$-labeled amino acids, $^{13}C$-labeled amino acids, $^{15}N$-labeled amino acids, $^{18}O$-labeled amino acids, $^{34}S$-labeled amino acids, and $^{33}S$-labeled amino acids. In one embodiment, the one or more isotope-labeled precursors is one isotope-labeled precursor, wherein the isotope-labeled precursor is $^{2}H_2O$.

In some embodiments, the focused beam of energy is a laser beam. In certain embodiments, the energy-induced volatilization system is selected from matrix-assisted laser desorption ionization (MALDI), nanoparticle initiator mass spectrometry (NIMS), secondary ion mass spectrometry (SIMS), laser desorption, desorption electrospray ionization (DESI), probe electrospray ionization (PESI), laser spray, and laser ablation electrospray ionization (LAESI). In certain embodiments, the ions of the first location and the second location are independently directed into a mass analyzer for mass spectrometry by an instrument modality, wherein the instrument modality is selected from the group consisting of time-of-flight (TOF), Orbitrap, Fourier-transform ion cyclotron (FTIR), magnetic sector, quadrupole, tandem mass spectrometers (MS/MS).

In another aspect, a method for kinetic microscopy comprising (a) administering to a living system a stable isotope, (b) obtaining a sample from the living system, (c) determining spatial measurements of the relative or absolute incorporation of the stable isotope in one or more molecules in the system by (1) detecting the isotopic incorporation in at least two locations in the sample and (2) determining the kinetics of stable isotope incorporation in the one or more molecules.

In another aspect, the method further comprising placing the sample on a mass spectrometry surface and the spatial measurements obtained by mass spectrometry methods such as MALDI-TOF, TOF-SIMS, or NIMS.

In another aspect, the method further comprising mapping and/or displaying the spatial measurements of the isotopic incorporation in the molecule as detected in sample. Such mapping or display thus providing a spatial topology or distribution of the localizations of isotopic incorporation in the sample.

In some embodiments, where the sample is a clinical sample, the mapping or display of the spatial measurements may be performed in situ in living tissues, for example with a heated scalpel or needle probe, to provide topographic and localization images of the intact tissue sample upon which an informed clinical decision, diagnosis or prognosis can be made.

In a preferred embodiment, a method comprising (a) preparing slides of said samples on a coated surface that permits or increases energy-dependant volatilization of molecules from said slide surface; (b) directing said volatilized molecules into a mass spectrometric ion source and analyzing said ions by mass spectrometry; (c) measuring the abundances of mass isotopomers within the isotopomeric envelopes of ions from molecules of interest on a pixel-by-pixel basis, and comparing to natural abundance (unlabeled) abundances of said mass isotopomers; (d) calculating the change within each pixel in the relative abundances of mass isotopomers from ion envelopes of interest, and from these data calculating by combinatorial probability and other mass isotopomer analytic methods kinetic and related biosynthetic parameters; and (e) visually displaying, on a pixel-by-pixel basis, metabolic kinetic and related biosynthetic results, by displaying selected molecules identified, a plurality of molecules identified, ratios of molecules identified, or other informative metrics based on the changes in mass isotopomer abundances for molecules of interest, in the form of heat maps, contour maps or other spatial representations of metabolic flux results.

In another aspect, a process that produces in situ spatially-localized images of metabolic fluxes and visually displays maps of metabolic fluxes along spatial coordinates, in histopathologic specimens from tissues, by use of the following steps.

In one step, administering to a living system a stable isotope-labeled precursor metabolite or metabolites that can be incorporated metabolically into molecules of interest in said living system. Such labeled precursors including, for example, $^2H_2O$ (heavy water), $[^{13}C]$acetate, $[^{13}C]$-glucose, $^{15}N$-amino acids, $^{18}O_2$, $^{13}C$-palmitate or other stable isotope-labeled molecules that are metabolic precursors for biosynthetic and metabolic pathways. The living system including, for example, cells in culture, tissues in vitro, whole animals, or human subjects.

In a next step, collecting a tissue or cell sample or a plurality of samples from culture or from said living system after a known period of time of exposure of said living system to said labeled precursor, by methods known in the art. Sample collection can include, for example, taking a surgical biopsy; surgical removal of a tissue or portion of a tissue; performing a percutaneous, endoscopic, transvascular, radiographic-guided or other non-surgical biopsy; euthanizing an experimental animal and removing tissue; collecting ex vivo experimental preparations; removing tissue at post-mortem examination; or other methods of collecting tissues.

In a third step, preparing histopathologic slides from said cell or tissue sample(s) by standard (non)-fixing methods known in the art, including cryopreservation, ethanol dehydration, OCL preservation, or other methods known in the art. In a preferred embodiment, preparing slides of said samples on a coated surface that permits or increases energy-dependant volatilization of molecules from said slide surface.

In a fourth step, subjecting said histopathology slide to a spatially-organized volatilization of molecules and ions wherein a focused energy source, such as a laser beam, or desorption system is rastered, across the tissue sample to create a series of discrete packets or a continuous flow of volatilized molecules in a spatially-organized manner. The molecules are charged (ions) or subjected to subsequent ionization. Energy-induced volatilization processes include, for example, matrix-assisted laser desorption ionization (MALDI), nanoparticle initiator mass spectrometry (NIMS), secondary ion mass spectrometry (SIMS), laser desorption, desorption electrospray ionization (DESI), probe electrospray ionization (PESI), laser spray, and laser ablation electrospray ionization (LAESI).

In a fifth step, directing said volatilized molecules into a mass analyzer, by use of instrument modalities that include, for example, time-of-flight (TOF), Orbitrap, Fourier-transform ion cyclotron (FTIR), magnetic sector, quadrupole, or other mass spectrometers. In a preferred embodiment, tandem mass spectrometers (MS/MS) are used, such as TOF-TOF or Quadrupole-TOF, wherein the second MS collects fragmentation spectra for molecular characterization of ions analyzed by the first mass spectrometer. In some embodiments, the ions that are identified for molecular structure from the MS/MS fragmentation spectra are lipid molecules, protein molecules, peptide molecules generated by in situ partial proteolysis prior to volatilization, primary metabolites, sugars, amino acids, nucleotides, or secondary metabolites.

In a sixth step, measuring the abundances of mass isotopomers within the isotopomeric envelopes of ions from molecules of interest in a spatially defined basis, and comparing to natural abundance (unlabeled) abundances of said mass isotopomers in each ion envelope. In a preferred embodiment, said ions are identified for molecular structure from the MS/MS fragmentation spectra. In some embodiments, said ions that are identified and quantified after volatilization by NIMS, TOF-SIMS, MALDI or other modality represent lipid molecules. In another preferred embodiment, said ions identified and quantified after volatilization by NIMS, TOF-SIMS, MALDI or other modality represent protein molecules or peptide molecules generated by in situ partial proteolysis prior to volatilization. In some embodiments, said ions identified and quantified after volatilization by NIMS, TOF-SIMS, MALDI or other modality represent primary metabolites (sugars, amino acids, nucleotides, etc). In some embodiments, said ions identified and quantified after volatilization by NIMS, TOF-SIMS, MALDI or other modality represent secondary metabolites.

In a seventh step, calculating the change in the pattern or relative abundances of mass isotopomers from ion envelopes of interest, and from these data calculating by combinatorial probability and other mass isotopomer analytic methods known in the art metabolic flux and related kinetic parameters, including for example synthesis rates, degradation rates, turnover rates, transport dynamics, metabolic sources, anatomic origins, subcellular interactions, oxidation, reduction, polymerization, conjugation, cleavage, addition, re-arrangement, transport, storage, secretion, or uptake; or the metabolic source or precursor pool used for biosynthesis; or other metabolic processes for each molecule or set of molecules.

In an eighth step, visually displaying, on a spatially defined basis, metabolic fluxes and related biosynthetic kinetic results, for selected molecules identified, a plurality of molecules identified, ratios of molecules identified, or other informative metrics based on the changes in mass isotopomer abundances for molecules of interest; wherein said displays are in the form of heat maps, contour maps or other spatial representations of histokinetic metabolic flux results, organized by spatial coordinates. In some embodiments, overlaying images of the same section of a tissue preparation or from adjacent serial sections of the same tissue preparation, using other histopathologic methods known in the art, such as vital dyes, in situ hybridization, or immunohistochemistry, to correlate metabolic fluxes and functional processes based on their shared spatial coordinates with specific cell types, subcellular organelles, molecular aggregates or other known morphologic features of a tissue. In some embodiments, beginning a metabolic flux microscopic interrogation of a tissue with a NIMS in situ metabolic flux analysis to identify regions or molecules of kinetic interest (e.g., "hot spots") in the tissue and then moving to TOF-SIMS from the same section or an adjacent section of the same tissue, to determine a more detailed fine structure of metabolic flux alterations in the tissue, e.g., at the cellular or subcellular level.

In another aspect, a system that generates and displays spatial images or maps of metabolic fluxes and biochemical kinetic processes for histopathologic specimens. The system comprising (a) a spatially defined mass spectrometry volatilization source, for interrogating across a tissue sample in a spatially-organized manner; (b) one or more detectors; (c) a computer for controlling the source and detectors, determining the abundances of the mass isotopomers detected on a pixel-by-pixel basis, calculating the metabolic flux of molecules that incorporate the mass isotopomers; and (d) image display for displaying an image of the metabolic flux results.

The process of displaying in situ metabolic flux results generated by the system providing imaging and mapping of metabolic fluxes by spatial coordinates in a sample. The imaging comprising, visually representing and displaying in situ metabolic flux results in the form of heat maps, contour maps or other images by spatial coordinates in a biologic tissue or cell preparation.

In one embodiment, visually overlaying images of the same section of a tissue preparation or from adjacent serial sections of the same tissue preparation, using other histopathologic methods known in the art, such as vital dyes, in situ hybridization, or immunohistochemistry, to correlate metabolic fluxes and functional processes based on their shared spatial coordinates with specific cell types, subcellular organelles, molecular aggregates or other known morphologic features of a tissue.

In another embodiment, visually representing data as functional metabolic processes, in the form of heat maps, contour maps or other images by spatial coordinates in a biologic tissue or cell preparation. The images may include, for example, the spatial topology of mitochondrial lipid synthesis in muscle cells; of the spatial distribution of prostanoid and eicosanoid turnover in inflammatory infiltrate tissues; of the pattern of lipogenesis in biopsies of cancer or precancer, and the presence of functional hot spots within a tumor; of the topology of hormonal synthesis in an endocrine tissue; for the presence of autonomous functional areas; for localization of regenerating cells and cell membranes, in a tissue, as in peripheral neuropathies; for the identification of spatially-localized timed biosynthetic events in a tissue based on calculated precursor pool enrichments; and many other means of representing the dense information generated about metabolic fluxes in space and time.

In another aspect, provided are methods embodied in software for processing metabolic flux data generated, comprising the general steps of: spectral peak finding, data loading, and chemical formula generation using algorithms for isotopic pattern generation, and/or algorithms for optimization and fitting isotopic patterns.

In a preferred embodiment, the isotopic pattern for a detected molecule is estimated as a function of the isotopic enrichment for one or more given elements. The appropriate isotopic enrichment for each element is the one that minimizes the difference between the theoretical isotopic pattern and the measured isotopic pattern. This process is repeated for multiple molecules across multiple spatial locations. In a preferred embodiment, the isotopic pattern for a detected molecule is estimated as a function of the isotopic enrichment for one or more given elements. This process is repeated for multiple molecules across multiple spatial locations.

In another embodiment, the ratio of the peak associated with a molecule containing a neutron enriched nucleus (ie: M1, M2, M3, etc) is normalized by either the monoisotopic peak (i.e., M0), the sum of all isotopologues for that molecule, or some other scaling factor that demonstrates the isotopic enrichment or depletion.

In another embodiment for cases where the individual isotopomers cannot be resolved either due to the mass analyzer resolution or for ions such as biopolymers, it is possible to detect alterations in isotopic enrichment or depletion by the shift in either the average mass of the ions of interest or a shift in the measured mass of the isotopologues belonging to the isotopic envelope of the molecule of interest.

In another embodiment, the isotopically-enriched or depleted sample is compared to one or more control isotopic patterns. Often, the control patterns are the isotopic pattern including the natural distribution of isotopes. Alternatively the control pattern is often the isotopic pattern obtained after an extended period of labeling (ie: the system has come reached a saturation point).

In some embodiments, the comparison involves overlaying images of the same section of a tissue preparation or from adjacent serial sections of the same tissue preparation, using other histopathologic methods known in the art, such as vital dyes, in situ hybridization, or immunohistochemistry, to correlate metabolic fluxes and functional processes based on their shared spatial coordinates with specific cell types, subcellular organelles, molecular aggregates or other known morphologic features of a tissue.

In another aspect, the software for processing metabolic flux data generated also visually represents data as functional metabolic processes, in the form of heat maps, contour maps or other images by spatial coordinates in a biologic tissue or cell preparation. In some embodiments, this is generated by use of univariate and multivariate statistical algorithms such as the analysis of variance, k-means clustering, principle component analysis, non-negative matrix factorization, and other approaches known to the field to grouping patterns of similar molecular distribution patterns and flux distributions patterns, and/or by use of mass difference alone or in conjunction with spatially varying patterns to resolve and identify adducts, degradation products, and multiple charge states for molecules.

Analysis of serial sections from a tissue specimen allows assembly of three-dimensional metabolic flux images of a tissue. Static histochemical images of the same tissue section or of adjacent tissue sections can be generated and overlaid on the spatial coordinates of the metabolic flux maps, to link metabolic fluxes to specific cell types, subcellular structures or other standard histologic features.

In another aspect, a mass spectrometry surface comprised of a solid mass spectrometry substrate and biological materials where said biological materials results from the in vivo incorporation of labeled precursors including, for example, $^2H_2O$ (heavy water), [$^{13}C$]acetate, [$^{13}C$]-glucose, $^{15}N$-amino acids, $^{18}O_2$, $^{13}C$-palmitate or other stable isotope-labeled molecules that are metabolic precursors for biosynthetic and metabolic pathways. In some embodiments, wherein the mass spectrometry substrate is not involved in the vaporization or ionization process, the substrate comprising materials including, for example, glass, silicon, stainless steel, and polymer or plastic materials. In other embodiments, where the mass spectrometry substrate is involved in the generation of gas phase molecules and or ions, suitable mass spectrometry substrates include, for example, nanostructure initiator mass spectrometry surfaces, porous silicon surfaces. In other embodiments, where the tissue or biological materials contain or have molecules deposited on them that participate in the generation of gas phase ions, suitable substrates include, for example, matrix materials such as alpha cinnamic acid, sinipinic acid, and others materials commonly known to the art.

In yet another aspect, provided is a method for generating a visual map of the spatial arrangement of relative or absolute isotopic enrichment for one or more molecules resulting from the administration of a heavy isotope as a metabolic precursor to a biological sample.

In yet another aspect, provided is a method for kinetic microscopy comprising: a) administering to a living system a stable isotope; b) interrogating the living system in a localized area; and c) determining spatial measurements of the relative or absolute incorporation of the stable isotope in one or more molecules in the living system by (1) detecting the isotopic incorporation in at least two locations in the localized area and (2) determining the kinetics of stable isotope incorporation in the one or more molecules. In some embodiments, the method further comprises interrogating the living system in a localized area with a probe tip for mass spectrometry and the spatial measurements are obtained by Probe ElectroSpray Ionization (PESI). In yet other embodiments, the method further comprises mapping and/or displaying the spatial measurements of the isotopic incorporation in the molecule as detected in said living system, such mapping or display thus providing a spatial topology or distribution of the localizations of isotopic incorporation in the localized area. In one embodiment, the localized area is a tumor. In other embodiments, the mapping or display of the spatial measurements provide topographic and localization images of the tumor upon which an informed clinical decision, diagnosis or prognosis can be made.

Provided herein is also an output generated according to any one of the methods described above.

In yet another aspect, provided is a depiction of a tissue specimen, the depiction includes: a first location of the tissue specimen, wherein the first location has a pattern, a color, a number, or a combination thereof, representing one or more molecular flux rates for one or more molecules of interest in the first location; and a second location of the tissue specimen, wherein the second location has a pattern, a color, a number representing one or more molecular flux rates for the one or more molecules of interest in the second location, wherein the second location is different from the first location, and wherein the first location and second location have a known spatial relationship. In some embodiments, the depiction is output in the form of an image, a heat map, a contour map, a table or a database. In other embodiments, the depiction is two-dimensional or three-dimensional. In certain embodiments, the known spatial relationship between the first location and the second location is based on distance, cells, or cellular compartments. In some embodiments, at least one or more molecular flux rates in the first location is the same as at least one or more molecular flux rates in the second location. In other embodiments, at least one or more the molecular flux rates in the first location is different than one or more of the molecular flux rates in the second location.

In yet another aspect, provided is a system for measuring in situ one or more metabolic flux rates of one or more molecules of interest in a sample and spatially mapping the one or more metabolic flux rates to a first location and a second location of the sample, the system includes: an energy-induced volatilization system, wherein the energy-induced volatilization system is configured to emit a focused beam of energy that scans across the sample to create a series of discrete packets or a continuous flow of ions in the first location and the second location of the sample; a mass analyzer, wherein the mass analyzer is configured to independently generate mass spectrometry data in the first location and the second location of the sample based on independent mass spectroscopy analysis of the ions in the first location and the second location of the sample; and a processor, wherein the processor is configured to independently calculate one or more molecular flux rates based on the mass spectrometry data and to map the one or more metabolic flux rates to the first location and the second location of the sample.

In some embodiments, the energy-induced volatilization system is selected from matrix-assisted laser desorption ionization (MALDI), nanoparticle initiator mass spectrometry (NIMS), secondary ion mass spectrometry (SIMS), laser desorption, desorption electrospray ionization (DESI), probe electrospray ionization (PESI), laser spray, and laser ablation electrospray ionization (LAESI). In other embodiments, the method further includes: an instrument modality, wherein the instrument modality is configured to independently direct the ions in each location into the mass analyzer. In certain embodiments, the instrument modality is selected from time-of-flight (TOF), Orbitrap, Fourier-transform ion cyclotron (FTIR), magnetic sector, quadrupole, tandem mass spectrometers (MS/MS). In other embodiments, the system further includes: a display system, wherein the display system is configured to display the one or more molecular flux rates of the one or more molecules of interest, wherein the one or more molecular flux rates of the one or more molecules of interest correspond to the first location and the second location of the sample.

In yet another aspect, provided is a non-transitory computer-readable medium having computer-executable instructions for determining one or more molecular flux rates of one or more molecules of interest in a sample, the instructions include: a) determining one or more molecular flux rates of one or more molecules of interest in a first location of the sample by analyzing relative and absolute incorporation of the isotope-labeled precursor in the one or more molecules of interest in the first location of the sample, b) determining one or more molecular flux rates of the one or more molecules of interest in a second location of the sample by analyzing relative and absolute incorporation of the isotope-labeled precursor in the one or more molecules of interest in the second location of the sample, wherein the second location is different from the first location, wherein the first location and second location have a known spatial relationship, and wherein the relative and absolute incorporation of the one or more isotope labels in the one or more molecules of interest in the first location is independent of the relative and absolute incorporation of the one or more isotope labels in the one or more molecules of interest in the second location; and c) outputting the one or more molecular flux rates in the first location and in the second location, and information relating to the known spatial relationship between the first location and the second location.

BRIEF DESCRIPTION OF THE FIGURES

The present application can be understood by reference to the following description taken in conjunction with the accompanying figures, in which like parts may be referred to by like numerals.

FIGS. 7A-7D depict the NIMS and TOF-SIMS flux imaging of mouse tissues in Example 2. Specifically, FIG. 7B depicts an image, with positioning shown on a whole-sectioned mouse-pup (~6 cm wide) (FIG. 7A), used to find metabolite markers that revealed spatial heterogeneity. These images were acquired using 50×50 micron pixels and a mass spectrum was recorded at each pixel to provide a whole-mouse image of ions (e.g. m/z 822, 828, 844) that were generally present in the majority of tissues, but had varying relative abundance generally correlated with tissue types. FIG. 7B depicts an ultra-high resolution (200 nm pixel size) TOF-SIMS flux imaging of a cross-section of a bundle of muscle fibers (separate mouse). FIG. 7C depicts a graph comparing isotope ratio to frequency of 5% $D_2O$ and 100% $H_2O$, showing that the ratio of m/z 28 to 27 provided a clear shift showing the labeling due to deuterium from water being incorporated into these ions. FIG. 7D depicts phosphocholine fractional labeling and ratio images detected using NIMS analysis of dissected livers from adult mice fed 5% deuterated water for three days. This demonstrates the integration of multiple imaging modalities including analysis of both intact molecules and fragments with TOF-SIMS.

FIG. 8A depicts the administration to a tumor-bearing mouse of $^2H_2O$-enriched water to incorporate deuterium into tissue by active metabolism. FIG. 8B depicts the excision, sectioning and imaging using NIMS of the deuterium-enriched tumor, and the generation of an individual mass spectrum for each pixel every 50 μm, with spectra made up of isotopologues from both $^2$H-labeled and unlabeled lipid molecules. FIG. 8C depicts serial sections of the tumor used for histopathology correlation with kMSI results. FIG. 8D depicts four intensity images showing the spatial distribution for both newly synthesized and pre-existing lipids based on the deconvolution of spectra performed to separate $^2$H-labeled and unlabeled lipids.

FIG. 12 depicts images that plot the calibration factor implemented for each pixel in the (A) control, unlabeled tumor and (B) deuterium-enriched tumor, where the calibration factor is calculated as the required shift in each measured spectrum that minimizes the distance between the measured and reference masses.

FIG. 13 depicts, for each of the 45 lipid species considered in Example 5, two patterns that are required to model the observed data: (1) the natural isotopic pattern for each compound, $F1_i$ and (2) the enriched isotopic pattern for each compound, $F2_i$ in which the linear coefficients of these 90 patterns (2 for each lipid species—$^2$H-labeled vs. unlabeled) and an offset term were solved by least-squares fitting in which the coefficients were subject to non-negativity constraints for each pixel.

In FIG. 26A, specifically shown in this figure is a kinetic image of the enrichment of palmitoyl carnitine using NIMS. At the coordinate indicated "Point 1" and the corresponding spectrum, little enrichment can be observed. In comparison, at the coordinate labeled "Point 2", significant enrichment is seen. In FIG. 26B, phosphocholine lipids was imaged as well. Thus, these figures demonstrate that the possibility of imaging the enrichment of many types of molecules.

DETAILED DESCRIPTION

The present disclosure provides a kinetic mass spectrometry imaging (kMSI) method, integrating soft desorption and ionization mass spectrometry with clinically-accepted in vivo metabolic labeling of tissue with an isotope label that can generate kinetic data, including images, of biological processes. For example, when applied to a tumor, kMSI can reveal heterogeneous spatial distributions of newly synthesized versus pre-existing lipids, with altered molecular flux patterns distinguishing region-specific intra-tumor subpopulations. This approach can characterize the diversity of molecular flux across heterogeneous tissue and enable identification of specific molecules involved in metabolism of region-specific cell subpopulations.

In one embodiment, the present disclosure provides for metabolic flux microscopy and represents an example of "functional microscopy" and "functional histopathology", in which functional dynamic processes in living systems are stained and detected. The functional dynamic processes may be imaged along spatial coordinates in tissue histopathology specimens. The concept of metabolic flux microscopy, or in situ metabolic flux histochemistry and the resulting metabolic flux histopathology images, is analogous to traditional static microscopy, such as vital dyes, in situ hybridization histochemistry, immunohistochemistry or electron microscopy. In these traditional static microscopies, dye-binding molecules, mRNA transcripts, protein antigens or electron-scattering structures, respectively, are visualized and mapped in a tissue. In metabolic flux microscopy, the dynamic metabolic fluxes of biomolecules and metabolic pathways, rather than their structure or concentration, are stained, detected, localized and imaged.

"Metabolic fluxes" or "molecular kinetics" are defined as the rates of chemical transformation or spatial movement of molecules and their flow through reactions and pathways in the metabolic network of a living system. "Flux(es)" are by definition rates (motion, in space or time), as contrasted with statics (snapshots of molecules at rest, lacking the motion and the dimension of time). Metabolic fluxes can refer to kinetics of small molecules, polymers, or macromolecules. Fluxes or rates of metabolic processes that can be imaged by metabolic flux microscopy in a tissue include synthesis, degradation, oxidation, reduction, methylation, polymerization, conjugation, addition, condensation, cleavage, re-arrangement, and other chemical reactions, as well as physical movement in space including transport, accessibility, storage, secretion, uptake, or other dynamic processes occurring in a living organism.

Figure 1:
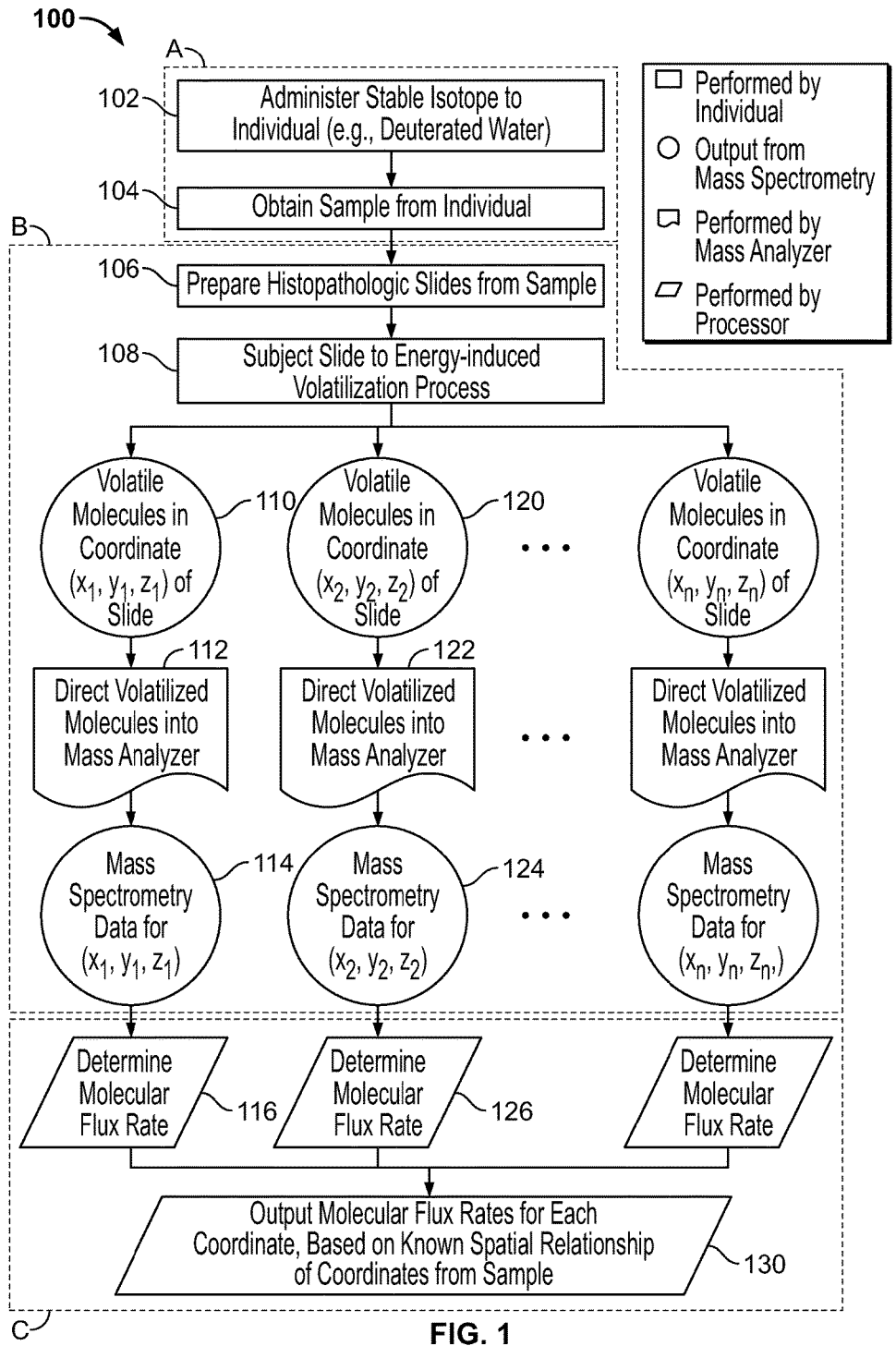
FIG. 1 depicts an exemplary process for outputting metabolic flux rates along spatial coordinates from a histopathologic sample from an individual.

Described herein are the basic concepts underlying metabolic flux microscopy and metabolic flux histopathology, including examples of images of the spatial topology of biosynthetic fluxes in tissues. With reference to FIG. 1, process 100 is an exemplary embodiment for producing in situ spatially-localized images of metabolic fluxes and visually displaying maps of metabolic fluxes along spatial coordinates in histopathologic tissue specimens.

In step 102, a stable isotope-labeled precursor is administered to an individual. The stable isotope-labeled precursor may be one or more stable isotope-labeled precursor metabolites, which can be metabolically incorporated into one or more molecules of interest in the living system. Such isotope-labeled precursors include, for example, $^2H_2O$ (heavy water), $[^{13}C]$acetate, $[^{13}C]$-glucose, $^{15}N$-amino acids, $^{18}O_2$, $^{13}C$-palmitate or other stable isotope-labeled molecules that are metabolic precursors for biosynthetic and metabolic pathways.

In step 104, a tissue or cell sample is obtained from the individual. In step 106, a histopathologic slide is prepared from the sample. In step 108, the histopathology slide is subjected to an energy-induced volatilization process, in which a focused energy source, such as a laser beam, or desorption system is rastered across the tissue sample to create a series of discrete packets or a continuous flow of volatilized molecules in a spatially-organized manner. The volatile molecules may be charged (ions), or may be further subjected to subsequent ionization. Examples of energy-induced volatilization processes include, for example, matrix-assisted laser desorption ionization (MALDI), nanoparticle initiator mass spectrometry (NIMS), secondary ion mass spectrometry (SIMS), laser desorption, desorption electrospray ionization (DESI), probe electrospray ionization (PESI), laser spray, and laser ablation electrospray ionization (LAESI). The volatilization process in process 100 is spatially-organized such that the sample on the slide is divided into independent, discrete sections corresponding to a spatial coordinate. Volatilized molecules in each coordinate are independently analyzed.

With reference again to FIG. 1, in steps 112 and 122, volatilized molecules 110 and 120, respectively, are then directed into a mass analyzer by use of instrument modalities such as time-of-flight (TOF), Orbitrap, Fourier-transform ion cyclotron (FTIR), magnetic sector, quadrupole, or other mass spectrometers. The abundances of mass isotopomers within the isotopomeric envelopes of ions from molecules of interest may be measured in a spatially defined basis, and compared to natural abundance (unlabeled) abundances of the mass isotopomers in each ion envelope. The ions may be identified and quantified using various techniques known in the art such as MS/MS, NEVIS, TOF-SIMS, and MALDI.

The mass analyzer produces mass spectrometry data 114 and 124 for each spatial coordinate. With respect to each spatial coordinate in process 100, it should be understood that "n" may be any whole integer, for example, 1, 2, 3, 4, 5, 6, 7, 8, 9, 10 or more. In steps 116 and 126, this mass spectrometry data may then be used to determine molecules flux rate associated with each spatial coordinate by calculating the change in the pattern or relative abundances of mass isotopomers from ion envelopes of interest, and from these data calculating by combinatorial probability and other mass isotopomer analytic methods known in the art metabolic flux and related kinetic parameters. Note that the sub-processes depicted in 110-116 and 120-126 are effectively independent of each other and may result in the same or different molecular flux rate values.

Figure 2:
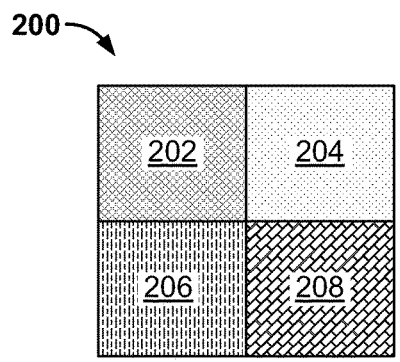
FIG. 2 depicts an exemplary output in the form of an image with four pixels, where each pixel represents the metabolic flux rate and/or other kinetic information and corresponds to the spatial coordinates the sample on the histopathologic slide analyzed.
Figure 3A:
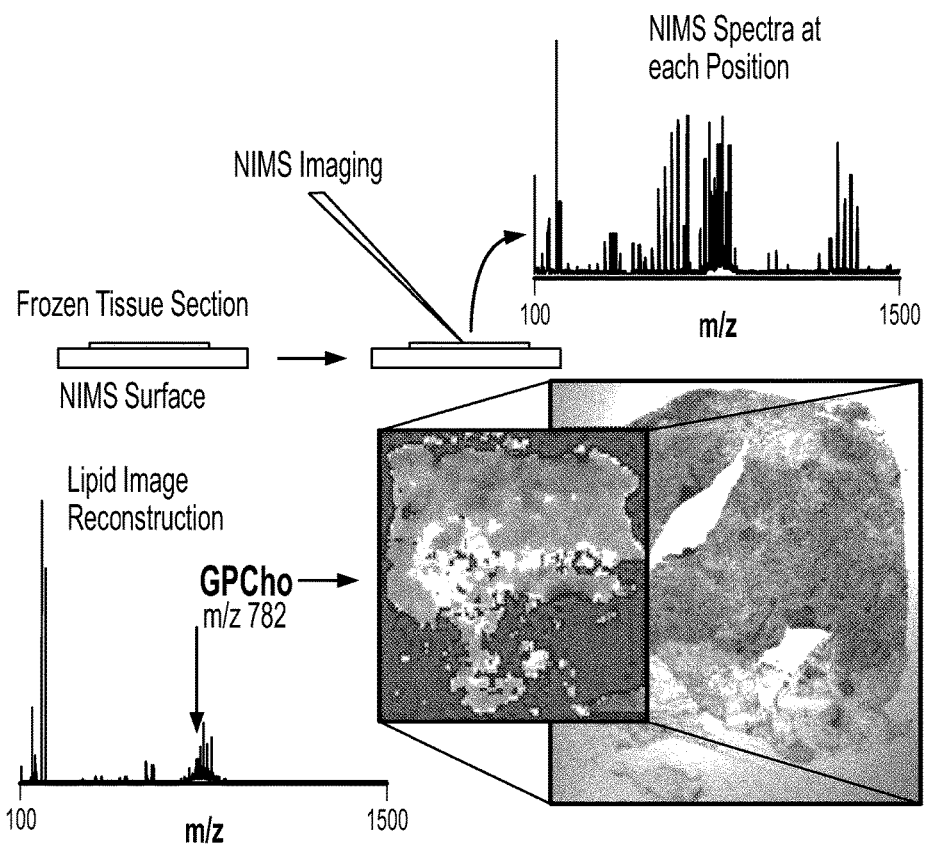
FIGS. 3A and 3B depict a first and a second workflow schematic, respectively, for NIMS analysis.
Figure 3B:
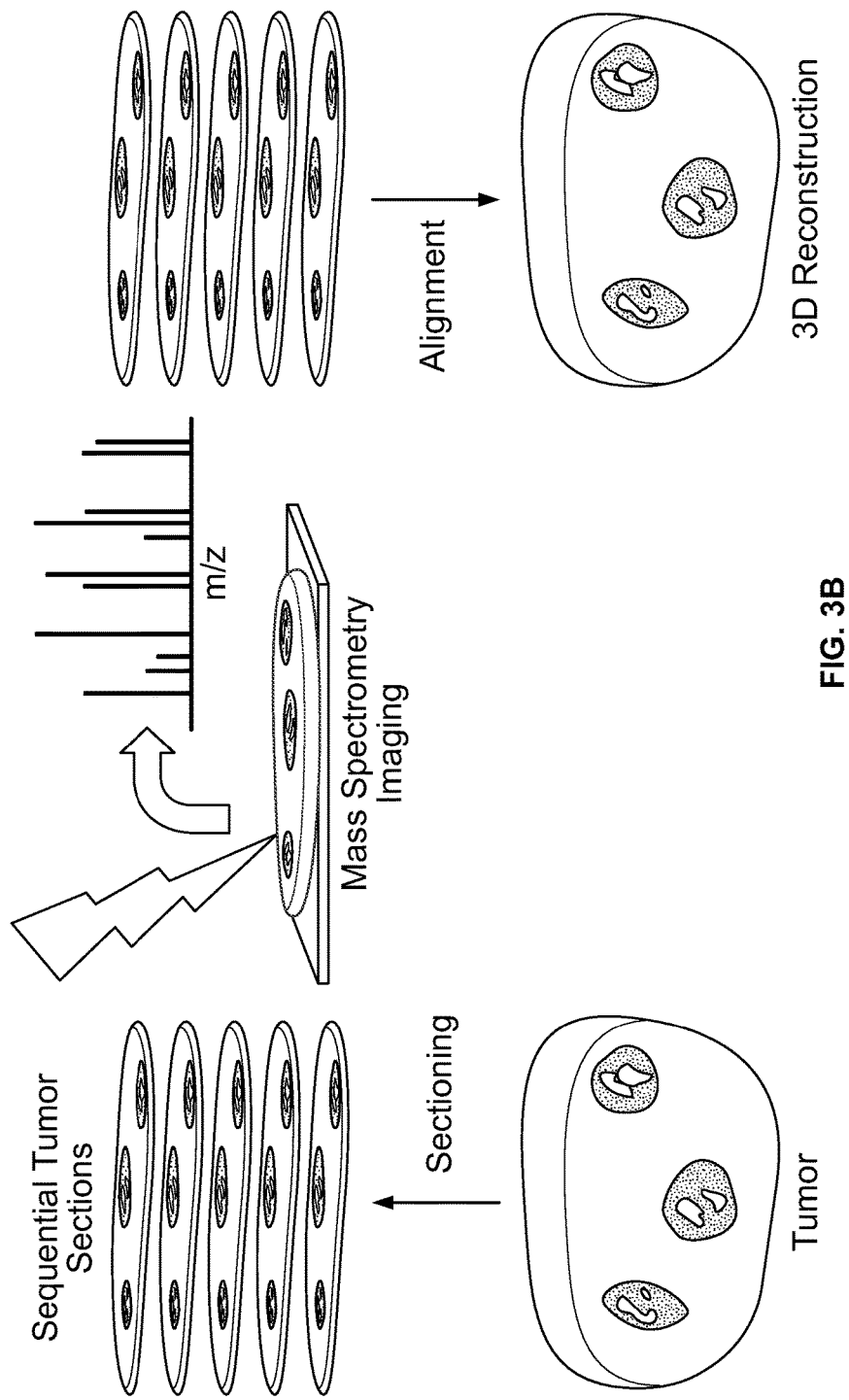

Then, in step 130, an output representing molecular flux rates for each spatial coordinate is generated. The output may be, for example, an image visually displaying, on a spatially defined basis, metabolic fluxes and related biosynthetic kinetic results, for the molecules identified. With reference to FIG. 2, an exemplary output is depicted in the form of image 200 with four pixels. While four pixels are depicted in this representative embodiment, any number of pixels may be depicted in other exemplary images. For example, an image may have 1, 2, 3, 4, 5, 6, 7, 8, 9, 10 or more pixels. Each pixel has a pattern, representing the molecular flux rate for a known spatial location of the sample. The cross-hatched pattern of pixel 202 represents a first molecular flux rate in a first location. The dotted pattern of pixel 204 represents a second molecular flux rate in a second location. The vertical line pattern of pixel 206 represents a third molecular flux rate in a third location. The bricks pattern of pixel 208 represents a fourth molecular flux rate in a fourth location. Each molecular flux rate in image 200 is different since the patterns are different. It should be understood that, in other exemplary embodiments, an image may have some pixels with the same molecular flux rate. Additionally, while image 200 displays kinetic information using patterns, it should be understood that the image displays using colors, or as a heat map, contour map or other spatial representations of histokinetic metabolic flux results organized by spatial coordinates. Pixels 202, 204, 206 and 208 each correspond to a known and different spatial location of the sample on the slide, in which each pixel also has a known spatial relationship. For example, as depicted in FIG. 2, the location of pixel 202 is different from the location of pixels 204, 206 and 208. Additionally, pixel 202 has a known spatial relationship to the other pixels: pixel 206, but to the left of pixel 204.

With reference again to FIG. 1, it should be understood that process 100 may be performed in one laboratory or multiple laboratories. For example, with reference to FIG. 1, box A (depicted in dotted lines) covers steps that may be performed in a clinical laboratory, whereas boxes B and C (depicted in dotted lines) cover steps that may be performed in the same or different analytical laboratories. Process 100 may be performed at different times. For example, a sample may be obtained according to steps in box A, and the sample may be stored for use at a later time. Similarly, mass spectrometry data may be generated according to steps in box B, while the determination of kinetic information and generation of the output may occur at a later time. In other exemplary embodiments, the process for producing images of kinetic information may start from step 106. In yet other embodiments, the process may start from the determination of molecular flux rates based on the mass spectrometry data acquired (e.g., steps 116 and 126).

Each of the steps and general techniques in process 6010 is described in further details below.

Administering Isotope-Labeled Precursor(s)

In order to determine molecular flux rates according to the methods descried herein, one or more isotope-labeled precursors are first administered to a living system. The precursor is administered for a period of time sufficient for one or more isotope labels to become incorporated into the living system. In certain embodiments, one isotope-labeled precursor is administered to the living system, in which case one isotope label is incorporated into the living system. The living system may include a cell, tissue, or organism (e.g., mouse, dogs, pigs, primates, or humans). In one embodiment, the living system is a human individual.

A. The Isotope-Labeled Precursor

The isotope-labeled precursor may be a stable isotope or radioisotope. For example, the stable isotope may include $^{2}H$, $^{13}C$, $^{15}N$, $^{18}O$, $^{3}H$, $^{14}C$, $^{35}S$, $^{32}P$, $^{125}I$, $^{131}I$, or other isotopes of elements present in organic systems. In one embodiment, the stable isotope is $^{2}H$.

In some embodiments, the precursor may be any molecule or combination of molecules having an isotope label that is incorporated into a protein. Isotope labels may be used to modify all precursor molecules disclosed herein to form isotope-labeled precursors. The entire precursor molecule may be incorporated into one or more proteins. Alternatively, a portion of the precursor molecule may be incorporated into one or more proteins. Precursor molecules may include, for example, $CO_2$, $NH_3$, glucose, lactate, $H_2O$, acetate, and fatty acids.

A protein precursor molecule may be any protein precursor molecule known in the art. These precursor molecules may be $CO_2$, $NH_3$, glucose, lactate, $H_2O$, acetate, and fatty acids. Precursor molecules of proteins may also include one or more amino acids. The precursor may be any amino acid. The precursor molecule may be a singly or multiply deuterated amino acid. For example, the precursor molecule may be selected from $^{13}C$-lysine, $^{15}N$-histidine, $^{13}C$-serine, $^{13}C$-glycine, $^{2}H$-leucine, $^{15}N$-glycine, $^{13}C$-leucine, $^{2}H_5$-histidine, and any deuterated amino acids. Labeled amino acids may be administered, for example, undiluted or diluted with non-labeled amino acids. All isotope labeled precursors may be purchased commercially, for example, from Cambridge Isotope Labs (Andover, Mass.).

Protein precursor molecules may also include any precursor for post-translational or pre-translationally modified amino acids. These precursors include, for example, precursors of methylation such as glycine, serine or $H_2O$; precursors of hydroxylation, such as $H_2O$ or $O_2$; precursors of phosphorylation, such as phosphate, $H_2O$ or $O_2$; precursors of prenylation, such as fatty acids, acetate, $H_2O$, ethanol, ketone bodies, glucose, or fructose; precursors of carboxylation, such as $CO_2$, $O_2$, $H_2O$, or glucose; precursors of acetylation, such as acetate, ethanol, glucose, fructose, lactate, alanine, $H_2O$, $CO_2$, or $O_2$; and other post-translational modifications known in the art.

The degree of labeling present in free amino acids may be determined experimentally, or may be assumed based on the number of labeling sites in an amino acid. For example, when using hydrogen isotopes as a label, the labeling present in C—H bonds of free amino acid or, more specifically, in tRNA-amino acids, during exposure to $^{2}H_2O$ in body water may be identified. The total number of C—H bonds in each non-essential amino acid is known—e.g. 4 in alanine, 2 in glycine, etc.

The precursor molecule for proteins may be water. The hydrogen atoms on C—H bonds are the hydrogen atoms on amino acids that are useful for measuring protein synthesis from $^{2}H_2O$ since the O—H and N—H bonds of proteins are labile in aqueous solution. As such, the exchange of $^{2}H$-label from $^{2}H_2O$ into O—H or N—H bonds occurs without the synthesis of proteins from free amino acids as described above. C—H bonds undergo incorporation from $H_2O$ into free amino acids during specific enzyme-catalyzed intermediary metabolic reactions. The presence of $^{2}H$-label in C—H bonds of protein-bound amino acids after $^{2}H_2O$ administration therefore means that the protein was assembled from amino adds that were in the free form during the period of $^{2}H_2O$ exposure—i.e. that the protein is newly synthesized. Analytically, the amino acid derivative used must contain all the C—H bonds, but must remove all potentially contaminating N—H and O—H bonds.

Hydrogen atoms from body water may be incorporated into free amino acids. $^{2}H$ or $^{3}H$ from labeled water can enter into free amino acids in the cell through the reactions of intermediary metabolism, but $^{2}H$ or $^{3}H$ cannot enter into amino acids that are present in peptide bonds or that are bound to transfer RNA. Free essential amino acids may incorporate a single hydrogen atom from body water into the α-carbon C—H bond, through rapidly reversible transamination reactions. Free non-essential amino acids contain a larger number of metabolically exchangeable C—H bonds, of course, and are therefore expected to exhibit higher isotopic enrichment values per molecule from $^{2}H_2O$ in newly synthesized proteins.

One of skill in the art will recognize that labeled hydrogen atoms from body water may be incorporated into other amino acids via other biochemical pathways. For example, it is known in the art that hydrogen atoms from water may be incorporated into glutamate via synthesis of the precursor α-ketoglutarate in the citric acid cycle. Glutamate, in turn, is known to be the biochemical precursor for glutamine, proline, and arginine. By way of another example, hydrogen atoms from body water may be incorporated into post-translationally modified amino acids, such as the methyl group in 3-methyl-histine, the hydroxyl group in hydroxyproline or hydroxylysine, and others. Other amino acids synthesis pathways are known to those of skill in the art.

Oxygen atoms ($H_2^{18}O$) may also be incorporated into amino acids through enzyme-catalyzed reactions. For example, oxygen exchange into the carboxylic acid moiety of amino acids may occur during enzyme catalyzed reactions. Incorporation of labeled oxygen into amino acids is known to one of skill in the art. Oxygen atoms may also be incorporated into amino acids from $^{18}O_2$ through enzyme catalyzed reactions (including hydroxyproline, hydroxylysine or other post-translationally modified amino acids).

Hydrogen and oxygen labels from labeled water may also be incorporated into amino acids through post-translational modifications. In one embodiment, the post-translational modification may already include labeled hydrogen or oxygen through biosynthetic pathways prior to post-translational modification. In another embodiment, the post-translational modification may incorporate labeled hydrogen, oxygen, carbon, or nitrogen from metabolic derivatives involved in the free exchange labeled hydrogens from body water, either before or after post-translational modification step (e.g. methylation, hydroxylation, phosphorylation, prenylation, sulfation, carboxylation, acetylation or other known post-translational modifications).

Protein precursors for that are suitable for administration into a living system include, for example, $H_2O$, $CO_2$, $NH_3$ and $HCO_3$, in addition to the standard amino acids found in proteins.

In one embodiment, isotope-labeled water may serve as a precursor in the methods described herein. Isotope-labeled water may be readily obtained commercially. "Isotope-labeled water" or "heavy water" includes water labeled with one or more specific heavy isotopes of either hydrogen or oxygen. Specific examples of isotope-labeled water include $^2H_2O$, $^3H_2O$, and $H_2^{18}O$. For example, $^2H_2O$ may be purchased from Cambridge Isotope Labs (Andover, Mass.), and $^3H_2O$ may be purchased from New England Nuclear, Inc. In general, $^2H_2O$ is non-radioactive and thus, presents fewer toxicity concerns than radioactive $^3H_2O$. $^2H_2O$ may be administered, for example, as a percent of total body water, e.g., 1% of total body water consumed (e.g., for 3 liters water consumed per day, 30 microliters $^2H_2O$ is consumed). If $^3H_2O$ is utilized, then a non-toxic amount, which is readily determined by those of skill in the art, is administered.

Relatively high body water enrichments of $^2H_2O$ (e.g., 1-10% of the total body water is labeled) may be achieved relatively inexpensively using the techniques of the invention. This water enrichment is relatively constant and stable as these levels are maintained for weeks or months in humans and in experimental animals without any evidence of toxicity. This finding in a large number of human subjects (>100 people) is contrary to previous concerns about vestibular toxicities at high doses of $^2H_2O$. As long as rapid changes in body water enrichment are prevented (e.g., by initial administration in small, divided doses), high body water enrichments of $^2H_2O$ can be maintained with no toxicities. For example, the low expense of commercially available $^2H_2O$ allows long-term maintenance of enrichments in the 1-5% range at relatively low expense (e.g., calculations reveal a lower cost for 2 months labeling at 2% $^2H_2O$ enrichment, and thus 7-8% enrichment in the alanine precursor pool, than for 12 hours labeling of $^2H$-leucine at 10% free leucine enrichment, and thus 7-8% enrichment in leucine precursor pool for that period).

Relatively high and relatively constant body water enrichments for administration of $H_2^{18}O$ may also be accomplished, since the $^{18}O$ isotope is not toxic, and does not present a significant health risk as a result.

In other embodiments, the isotope-labeled precursor used in the methods described herein is $[1-^{13}C_1]$ acetate, $[U-^{13}C_6]$ glucose, $^{15}N$-amino acids, $^{18}O_2$, $^{13}C$-palmitate or other stable isotope-labeled metabolic precursors known in the art.

B. Methods of Administering the Isotope-Labeled Precursor

The methods of administering the one or more isotope-labeled precursors may vary depending upon the absorptive properties of the isotope-labeled precursor and the specific biosynthetic pool into which each compound is targeted. Precursors may be administered to organisms, plants and animals including humans directly for in vivo analysis. In addition, precursors may be administered in vitro to living cells. Specific types of living cells include hepatocytes, adipocytes, myocytes, fibroblasts, neurons, pancreatic β-cells, intestinal epithelial cells, leukocytes, lymphocytes, erythrocytes, microbial cells and any other cell-type that can be maintained alive and functional in vitro.

Generally, an appropriate mode of administration is one that produces a steady state level of precursor within the biosynthetic pool and/or in a reservoir supplying such a pool for at least a transient period of time. Intravenous or oral routes of administration are commonly used to administer such precursors to organisms, including humans. Other routes of administration, such as subcutaneous or intramuscular administration, optionally when used in conjunction with slow release precursor compositions, are also appropriate. Compositions for injection are generally prepared in sterile pharmaceutical excipients.

Obtaining Sample

The sample used in the methods described herein may be obtained from the living system and then prepared by standard techniques for mass spectrometry based imaging.

A sample may include a tissue histology specimen from tissues such as, for example, the gut, skin, organs, breast, prostate, brain, bone, muscle, liver, and gut. The sample may also be obtained from bodily fluids including, for example, urine, blood, interstitial fluid, edema fluid, saliva, lacrimal fluid, inflammatory exudates, synovial fluid, abscess, empyema or other infected fluid, cerebrospinal fluid, sweat, pulmonary secretions (sputum), seminal fluid, feces, bile, and intestinal secretions. The sample may further include biofilms, microbiomes and other microbial organisms. The sample may be a clinical sample, upon which a clinical decision, diagnosis or prognosis can be made using the output generated according to the methods described herein.

The sample may be obtained, for example, by blood draw, urine collection, biopsy, or other methods known in the art. In some embodiments, the sample is obtained by taking a surgical biopsy; surgical removal of a tissue or portion of a tissue; performing a percutaneous, endoscopic, transvascular, radiographic-guided or other non-surgical biopsy; euthanizing an experimental animal and removing tissue; collecting ex vivo experimental preparations; removing tissue at post-mortem examination; or other methods known in the art for collecting tissue samples. The methods of obtaining a sample may also vary and be specific to the molecules of interest.

Standard techniques for preparing a sample for mass spectrometry include, for example, freezing and slicing, lyophilization, cryopreservation, ethanol dehydration, OCL preservation, and other suitable methods known in the art. In some embodiments, the samples are prepared on a slide with a coated surface that permits or increases energy-dependent volatilization of molecules from the surface of the slide.

Analysis

The sample is then analyzed using any number of mass spectrometry techniques to analyze the masses of charged molecules (ions) in the sample or generated or released by the sample. There are a wide range of methods that may be used to generate these gas phase ions. Suitable approaches include methods where molecules are transferred to the gas phase and ionized at the same time and/or methods where these two processes are decoupled.

a. Molecules of Interest

Molecules of interest includes any molecule including, for example, amino acids, carbohydrates, fatty acids, peptides, sugars, lipids, nucleic acids, polynucleotides, glycosaminoglycans, polypeptides, or proteins that are present within a metabolic pathway within a living system.

B. Ionizing Molecules of Interest

The volatile molecules generated in the methods described herein are gas phase ions. These gas phase ions from spatially-defined regions of the sample are generated using any of the wide range of methods known in the art for generating gas phase ions from a sample. This includes methods for directly characterizing histology specimens, those that apply materials to the specimens to assist mass spectrometry analysis, and those that utilize special surfaces for mass spectrometry analysis. For example, using Secondary Ion Mass Spectrometry (SIMS) a primary ion beam is used to desorb molecules either as ions or neutrals (that are subsequently ionized for example using photoionization), using Laser Desorption molecules and ions can be transferred to the gas phase, Desorption ElectroSpray Ionization is used to desorb molecules and ions using an ElectroSpray cone, etc. In other cases, the sample is treated with materials that assist in molecule desorption and ionization for example Matrix Assisted Laser Desorption (MALDI) where the histology specimen is applied to a solid surface, a matrix molecule is applied, and a laser is used for molecule desorption and ionization. In other cases, the histopathology specimen is applied to a surface that facilitates molecule desorption or desorption/ionization for example nanostructure initiator mass spectrometry or Desoption Ionization of Silicon.

In a preferred embodiment where the sample is analyzed directly, the sample is prepared on a surface and is directly interrogated using Time-of-flight Secondary Ion Mass Spectrometry (TOF-SIMS). In another preferred where the sample is treated with materials for mass spectrometry analysis the sample is applied to a metal surface, followed by matrix application, and matrix-assisted laser desorption ionization (MALDI) analysis. In another preferred embodiment that utilizes a special surface for mass spectrometry analysis, a nanostructure-initiator mass spectrometry surface is used for volatilization of target molecules when subjected to laser irradiation.

In a specific embodiment, the sample is a histopathology specimen and is analyzed directly. The histopathology specimen is prepared on a slide and then subjected to a volatilization process wherein a focused energy source such as a laser beam is rastered across the tissue slide preparation in a spatially-organized fashion, creating volatilized molecules for detection by a mass spectrometer along spatial coordinates. In one embodiment, the histopathology specimen is prepared on a silicon surface and is directly interrogated using Time-of-flight Secondary Ion Mass Spectrometry (TOF-SIMS). In another specific embodiment, the histopathology specimen is treated with materials for mass spectrometry analysis. Frozen tissue can be applied to a stainless steel surface, followed by matrix application, and matrix-assisted laser desorption ionization (MALDI) analysis.

In another specific embodiment, the sample is placed on a nanostructure-initiator mass spectrometry (NIMS) surface which utilizes a special surface for volatilization of target molecules when subjected to laser irradiation using nanostructure-initiator mass spectrometry. One of the inventors previously described and developed a new, ultra-high sensitivity mass spectrometry technique called Nanostructure-Initiator Mass Spectrometry[9] which is currently capable of mass analysis at 15 μm resolution[23]. NIMS works by absorbing metabolites on a surface where nanostructured pores contain a vacuum compatible 'initiator' liquid. Laser-irradiation of the surface vaporizes the pore-trapped initiator and triggers desorption/ionization of surface absorbed analytes. As the laser rasters across a tissue surface, NIMS creates a mass spectrum at each point, creating a spatial map of metabolites across the tissue. NIMS and related methods and compositions is described in U.S. Patent Publication Nos. 2008/0128608, 2009/0042741, and 2010/0056392, and in Lee do Y, Bowen B P, Northen T R, "Mass spectrometry-based metabolomics, analysis of metabolite-protein interactions, and imaging," *Biotechniques*. 2010 August; 49(2): 557-65. Review; Yanes O, Woo H K, Northen T R, Oppenheimer S R, Shriver L, Apon J, Estrada M N, Potchoiba M J, Steenwyk R, Manchester M, Siuzdak G., "Nanostructure initiator mass spectrometry: tissue imaging and direct biofluid analysis," *Anal Chem*. 2009 Apr. 15; 81(8):2969-75; Woo H K, Northen T R, Yanes O, Siuzdak G, "Nanostructure-initiator mass spectrometry: a protocol for preparing and applying NIMS surfaces for high-sensitivity mass analysis," *Nat Protoc*. 2008; 3(8):1341-9; Northen T R, Lee J C, Hoang L, Raymond J, Hwang D R, Yannone S M, Wong C H, Siuzdak G., "A nanostructure-initiator mass spectrometry-based enzyme activity assay," *Proc Natl Acad Sci USA*. 2008 Mar. 11; 105(10):3678-83. Epub 2008 Mar. 4; and Northen T R, Yanes O, Northen M T, Marrinucci D, Uritboonthai W, Apon J, Golledge S L, Nordström A, Siuzdak G., "Clathrate nanostructures for mass spectrometry," *Nature*. 2007 Oct. 25; 449(7165):1033-6, all of the above which are hereby incorporated by reference in their entireties for all purposes and specifically with respect to the use of NIMS protocols.

Many of these and other related methods directly generate gas phase ions for subsequent mass analysis. In another embodiment, it may be desirable to subject desorbed molecules or ions to subsequent ionization methods. For example, in gas chromatography mass spectrometry, the initial volatilization process typically generates primarily neutral molecules where are subsequently subjected to electron ionization or chemical ionization prior to mass analysis. A wide range of other ionization approaches are used to generate, enrich, or modify neutrals and ions using light, electrons, chemical methods, charged molecules, fragmentation, and other methods common to the art. Suitable methods include, for example, atmospheric chemical ionization (APCI), or photochemical ionization.

C. Producing Mass Spectrometry Data

The volatile molecules that result either from direct desorption/ionization or subsequent ionization/fragmentation processing of the sample are analyzed to separate or measure the mass-to-charge ratio for the ions and the abundance of these ions. A wide range of mass analyzers are known and available in the art that are capable of resolving the relative abundances of mass isotopomers or the pattern of mass isotopomer abundances in the ion envelopes.

"Mass isotopomer" refers to family of isotopic isomers that is grouped on the basis of nominal mass rather than isotopic composition. A mass isotopomer may include molecules of different isotopic compositions, unlike an isotopologue (e.g., $CH_3NHD$, $^{13}CH_3NH_2$, $CH_3^{15}NH_2$ are part of the same mass isotopomer but are different isotopologues). In operational terms, a mass isotopomer is a family of isotopologues that are not resolved by a mass spectrometer. For quadrupole mass spectrometers, this typically means that mass isotopomers are families of isotopologues that share a nominal mass. Thus, the isotopologues $CH_3NH_2$ and $CH_3NHD$ differ in nominal mass and are distinguished as being different mass isotopomers, but the isotopologues $CH_3NHD$, $CH_2DNH_2$, $^{13}CH_3NH_2$, and $CH_3^{15}NH_2$ are all of the same nominal mass and hence are the same mass isotopomers. Each mass isotopomer is therefore typically composed of more than one isotopologue and has more than one exact mass. The distinction between isotopologues and mass isotopomers is useful in practice because all individual isotopologues are not resolved using quadrupole mass spectrometers and may not be resolved even using mass spectrometers that produce higher mass resolution, so that calculations from mass spectrometric data must be performed on the abundances of mass isotopomers rather than isotopologues. The mass isotopomer lowest in mass is represented as $M_0$; for most organic molecules, this is the species containing all $^{12}C$, $^1H$, $^{16}O$, $^{14}N$, etc. Other mass isotopomers are distinguished by their mass differences from $M_0$ ($M_1$, $M_2$, etc.). For a given mass isotopomer, the location or position of isotopes within the molecule is not specified and may vary (i.e., "positional isotopomers" are not distinguished).

"Mass isotopomer pattern" refers to a histogram of the abundances of the mass isotopomers of a molecule. Traditionally, the pattern is presented as percent relative abundances where all of the abundances are normalized to that of the most abundant mass isotopomer; the most abundant isotopomer is said to be 100%. The preferred form for applications involving probability analysis, such as mass isotopomer distribution analysis (MIDA), however, is proportion or fractional abundance, where the fraction that each species contributes to the total abundance is used. The term "isotope pattern" may be used synonomously with the term "mass isotopomer pattern".

Instrument modalities that can be used to generate the volatile molecules include, for example, matrix-assisted laser desorption ionization (MALDI), nanoparticle initiator mass spectrometry (NIMS), desorption electrospray ionization, laser desorption, and secondary ion mass spectrometry (SIMS), time-of-flight (TOF), ion trap (Orbitrap), Fourier-transform ion cyclotron (FTIR), magnetic sector, quadrupole, or other mass analyzers and combinations of mass analyzers. In a preferred embodiment, time-of-flight and tandem mass spectrometers (MS/MS) are used, such as, quadrupole-Time-of-flight (QTOF), TOF-TOF wherein the ions analyzed for shift in mass isotopomer abundance pattern by the first mass spectrometer have fragmentation spectra collected and characterized for molecular structure by the second MS.

In another embodiment, the ions identified and quantified after volatilization by NIMS, TOF-SIMS, MALDI or other modality for interrogating lipid molecules in the tissue. In another embodiment, said ions identified and quantified after volatilization by NIMS, TOF-SIMS, MALDI or other modality represent protein molecules or peptide molecules generated by in-situ partial proteolysis in the tissue prior to volatilization.

In another embodiment, a fine needle probe tip is used directly on the sample for Probe electrospray ionization (PESI) as described in Chen L C, Nishidate K, Saito Y, Mori K, Asakawa D, Takeda S, Kubota T, Terada N, Hashimoto Y, Hori H, Hiraoka K, "Application of probe electrospray to direct ambient analysis of biological samples," Rapid Commun Mass Spectrom. 2008 August; 22(15):2366-74 and Yoshimura K, Chen L C, Yu Z, Hiraoka K, Takeda S., "Real-time analysis of living animals by electrospray ionization mass spectrometry," Anal Biochem. 2011 Oct. 15; 417(2):195-201. Epub 2011 Jun. 22, both hereby incorporated by reference for all purposes and specifically with respect to the protocols for PESI.

Ultimately the ion signal is recorded using one or more ion detectors that record a signal when the ion passes by or hits a surface. There are a wide range of methods including faraday cups, ion-to-photon detectors, microchannel plates, systems that detect ions passing by a plate, and other methods common to the art.

The mass spectrometry data is independently generated and collected for each spatially-defined location of the sample. The spatial locations of the resulting mass spectrometry data are typically obtained by linking the position of desorption or desorption/ionization process to the resulting mass spectrometry data for a given location. For example, with reference to FIG. 1, spectral data can be stored sequentially and is indexed to the x, y, z coordinates of the spectrometry data at that position in the sample. In another embodiment, marker molecules within the sample are also used to provide spatial coordinates to create mass spectrometry images.

It should be understood, however, that the sample on the slide may be spatially defined such that there is a known relationship between two or more unique locations of the sample. For example, in some embodiments, the sample may be spatially defined by a coordinate system. Suitable coordinate systems may include, for example, a Cartesian coordinate system and a Polar coordinate system. The sample may also be spatially defined based on physiological factors, rather than distance. For example, in other embodiments, the sample may also be spatially defined by cells or cellular compartments (e.g., nucleus, membrane, or cytoplasm).

D. Calculating Molecular Flux Rates

Various methods and techniques may be employed to calculate molecular flux rates from the mass spectrometry data generated. For example, molecular flux rates may be calculated based on the content, rate of incorporation and/or pattern or rate of change in content and/or pattern of isotope labeling of the molecules of interest. See e.g., U.S. Patent Application No. 2005/0202406, which is hereby incorporated by reference for all purposes and specifically with respect to describing how to measure relative and absolute mass isotope abundances as described in paragraphs [0194]-[0205] and to calculate molecular flux rates in paragraphs [0206]-[0215].

In one embodiment, metabolic flux can be calculated by combinatorial probability and other mass isotopomer analytic methods known in the art. Typical kinetic parameters include, for example, synthesis rates, degradation rates, turnover rates, transport dynamics, metabolic sources, anatomic origins, subcellular interactions, oxidation, reduction, polymerization, conjugation, cleavage, addition, re-arrangement, transport, storage, secretion, or uptake; or the metabolic source or precursor pool used for biosynthesis; or other metabolic processes for each molecule or set of molecules.

Identification of the biosynthetic rate of a molecule is ultimately dictated by an enrichment or depletion in one or more mass isotopologues associated with that molecule. This general principle is extended to algorithms that model the isotopic pattern to best represent the detected signal. This process is applied throughout the data to identify spatially-defined biosynthetic rates. Methods and algorithms are known and described by Hellerstein M K, Christiansen M, Kaempfer S, Kletke C, Wu K, Reid J S, Mulligan K, Hellerstein N S, Shackleton C H, "Measurement of de novo hepatic lipogenesis in humans using stable isotopes," *J Clin Invest.* 1991 May; 87(5):1841-52.; Hellerstein M K, Neese R A, "Mass isotopomer distribution analysis: a technique for measuring biosynthesis and turnover of polymers," *Am J Physiol.* 1992 November; 263(5 Pt 1):E988-1001; Sperling E, Bunner A E, Sykes M T, Williamson J R, "Quantitative analysis of isotope distributions in proteomic mass spectrometry using least-squares Fourier transform convolution," *Anal Chem.* 2008 Jul. 1; 80(13):4906-17. Epub 2008 Jun. 4; Rockwood A L, Kushnir M M, Nelson G J., "Dissociation of individual isotopic peaks: predicting isotopic distributions of product ions in MSn," *J Am Soc Mass Spectrom.* 2003 April; 14(4):311-22, and in all of which are hereby incorporated by reference in their entireties.

In one embodiment, the isotopic pattern for a detected molecule is estimated as a function of the isotopic enrichment for one or more given elements. The appropriate isotopic enrichment for each element is the one that minimizes the difference between the theoretical isotopic pattern and the measured isotopic pattern. This process is repeated for multiple molecules across multiple spatial locations. As used herein, "isotopic pattern" refers to the internal relationships of isotopic labels within a molecule or population of molecules, e.g., the relative proportions of molecular species with different isotopic content, the relative proportions of molecules with isotopic labels in different chemical loci within the molecular structure, or other aspects of the internal pattern rather than absolute content of isotopes in the molecule. "Isotopic content" refers to the content of isotopes in a molecule or population of molecules relative to the content in the molecule or population of molecules naturally (i.e., prior to administration or contacting of isotope labeled precursor subunits). The term "isotope enrichment" is used interchangeably with isotopic content herein.

In another embodiment, the ratio of the peak associated with a molecule containing a neutron enriched nucleus (i.e., $M_1$, $M_2$, $M_3$, etc.) is normalized by either the monoisotopic peak (i.e., $M_0$), the sum of all isotopologues for that molecule, or some other scaling factor that demonstrates the isotopic enrichment or depletion.

In another embodiment for cases where the individual isotopomers cannot be resolved either due to the mass analyzer resolution or for ions such as biopolymers, it is possible to detect alterations in isotopic enrichment or depletion by the shift in either the average mass of the ions of interest or a shift in the measured mass of the isotopologues belonging to the isotopic envelope of the molecule of interest.

As used herein, "isotopologues" refer to isotopic homologues or molecular species that have identical elemental and chemical compositions but differ in isotopic content (e.g., $CH_3NH_2$ vs. $CH_3NHD$). Isotopologues are defined by their isotopic composition. Therefore, each isotopologue has a unique exact mass but may not have a unique structure. An isotopologue usually includes of a family of isotopic isomers (referred to herein as "isotopomers"), which differ by the location of the isotopes on the molecule (e.g., $CH_3NHD$ and $CH_2DNH_2$ are the same isotopologue but are different isotopomers).

"Mass isotopomer envelope" or "isotopic envelope" refers to the set of mass isotopomers that make up the family associated with each molecule or ion fragment monitored.

In another embodiment, the isotopically-enriched or depleted sample is compared to one or more control isotopic patterns. Often, the control patterns are the isotopic pattern including the natural distribution of isotopes. Alternatively the control pattern is often the isotopic pattern obtained after an extended period of labeling (i.e., the system has come reached a saturation point).

Mass Isotopomer Distribution Analysis (MIDA) and Related Techniques

In one exemplary embodiment, MIDA, or MIDA-like techniques, are employed to calculate molecular flux rates. MIDA analysis relies on looking at the ratio of mass isotopologues associated with a molecule to determine physical parameters.

Variations of MIDA combinatorial algorithm are discussed in a number of different sources known to one skilled in the art. See Hellerstein and Neese (1999), as well as Chinkes, et al. (1996), and Kelleher and Masterson (1992), and U.S. patent application Ser. No. 10/279,399, all of which are hereby incorporated by reference in their entirety. For example, MIDA variations may involve analyzing the lightest molecule in the dataset and determining f by looking at its M0 and M1 isotopologues, assuming that these peaks are purely from the starting molecule. Once f is determined, the complete isotopic pattern is calculated (M0, M1, M2, etc). These values are subtracted from the measured spectrum. Next, the second lightest molecule in the dataset can be fit using its M0 and M1 (following the subtraction of the pattern from the first molecule). These steps are repeated for all the molecules of interest in the dataset.

In one embodiment, the monoisotopic peak (M0) and the isotopologue containing one additional neutron (M1) can be compared to determine the fractional enrichment, referred to here as f, of a molecule. In another case, the ratios M0:M1 and the M0:M2, M0:M3, etc. can be used to fit not only the fractional enrichment but also the number of sites on the molecule where enrichment can occur. The number of sites where enrichment can occur may be referred to as N. The M0:M1 ratio is a function of both f and N. The M0:M2, M0:M3, M0:M4, etc. are functions of both f and N as well. Therefore, using the MIDA approach to determine f and N, at least the M0:M1 and the M0:M2 ratios are used.

Spectral Pattern Isotope Fitter (SPIF)

Alternatively, in other embodiments, a Spectral Pattern Isotope Fitter (SPIF) approach may be employed to calculate molecular flux rates. SPIF includes specific approaches for global analysis of spectra containing isotopic patterns from more than one molecule with overlapping isotopes using approximation for N, f or both parameters. This approximation is critical to many applications where one or both of these parameters cannot be measured and especially where few isotopologues are not overlapping with other molecules. Specifically, SPIR allows for global fitting of many molecules simultaneously, deconvolution of spectra into multiple labeled populations and unlabeled species, and appropriate and constrained use of approximations.

One SPIF approach, for example, involves fitting for each molecule a value of N and f and intensity for a labeled form of each molecule and the intensity for an unlabeled form of each molecule. By way of example, for 45 molecules, the following parameters would be curve fit: (1) 45 different values of f (one for each molecule); (2) 45 different values of N (one for each molecule); (3) 45 different intensity values (for each labeled molecule); and (4) 45 different intensity values (for each unlabeled molecule).

The approach described above can be simplified to solve the intensity values for each spectrum using non-negative regression. Now, for each guess of the 45 values of f and the 45 values of N, the 45 intensity values of the labeled molecules and the 45 intensity values of the unlabeled molecules are determined by techniques commonly used in linear algebra.

Another SPIF approach involves specifying N for each of the molecules. This significantly reduces the search space. Values of N can be specified from other experiments, literature, or by inference from biochemistry. Various multivariate optimization algorithms, including pattern search, swarm optimization, and genetic algorithms, can be used to determine the values of f and non-negative constraints on linear models can be used to determine the intensity values. For signal having suitable signal quality this is a very reasonable approach to utilize.

Yet another SPIF approach involves specifying f for each of the molecules. This also significantly reduces the search space. Values of f are specified from other experiments, literature, or by inference from biochemistry. Often in this approach f is maximally enriched due to prolonged feeding of isotopically enriched material. In other words, the molecules of interest are fully labeled. Various multivariate optimization algorithms, including pattern search, swarm optimization, and genetic algorithms, can be used to determine the values of N and non-negative constraints on linear models can be used to determine the intensity values. For signal having suitable signal quality this is a very reasonable approach to utilize.

Figure 24:
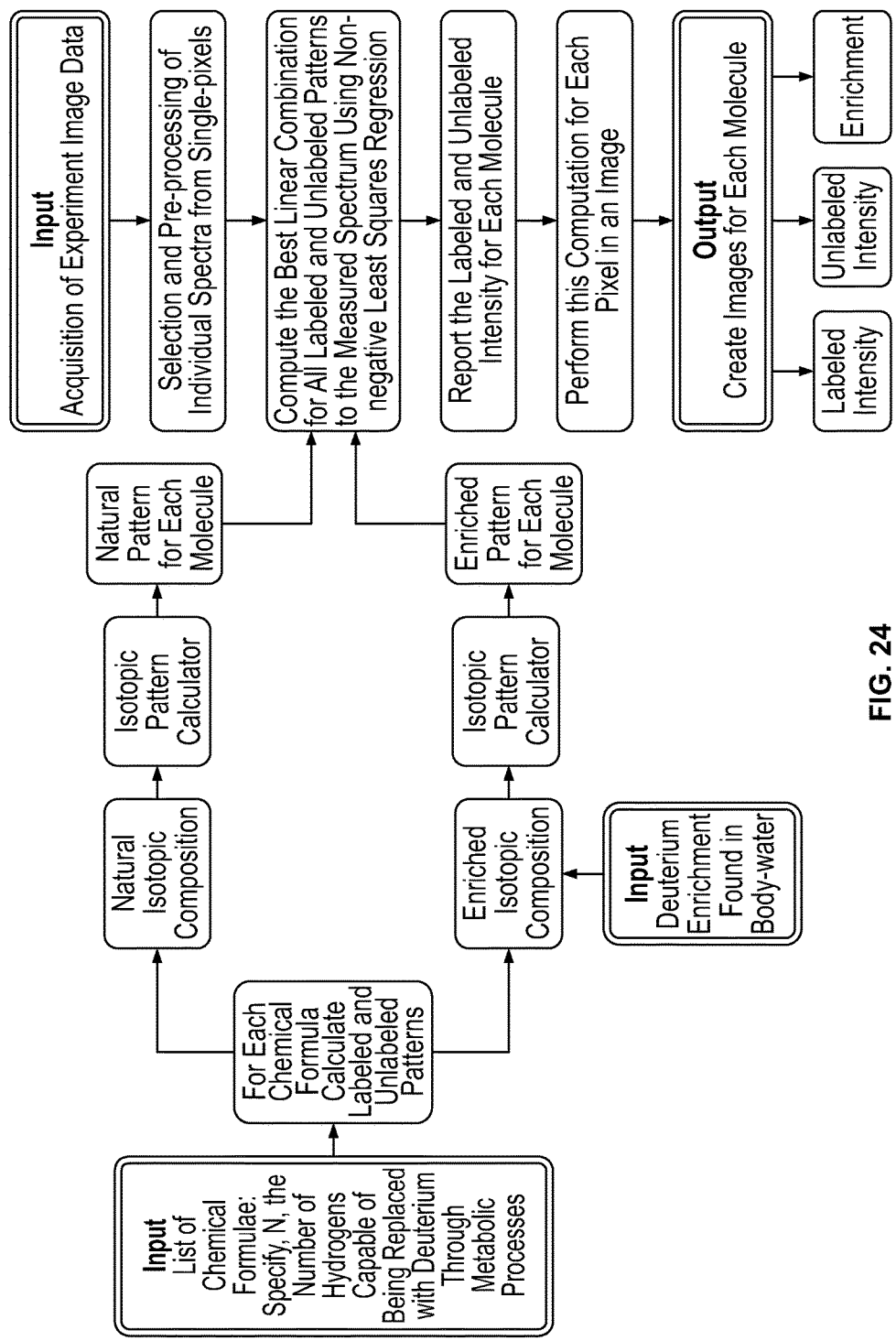
FIG. 24 depicts an exemplary process for analyzing mass spectrometry data containing isotopic patterns using spectral pattern isotope fitter (SPIF) analysis.

With reference to FIG. 24, an exemplary SPIF approach constraining both f and N for each labeled molecule is depicted. This information may be used to calculate the relative contribution of different labeled populations of molecules. For example, f can be estimated as equal to the enrichment in the body water of the animal. Values of N can be specified from other experiments, literature, or by inference from biochemistry. This approach does not require multivariate optimization and the intensity of each labeled molecule and unlabeled molecule can be determined from regression techniques alone. This approach specifically leaves out the M2 and higher isotopologues, and can be employed to deal with the overlapping isotopes from multiple molecules.

Generating Output

Figure 10:
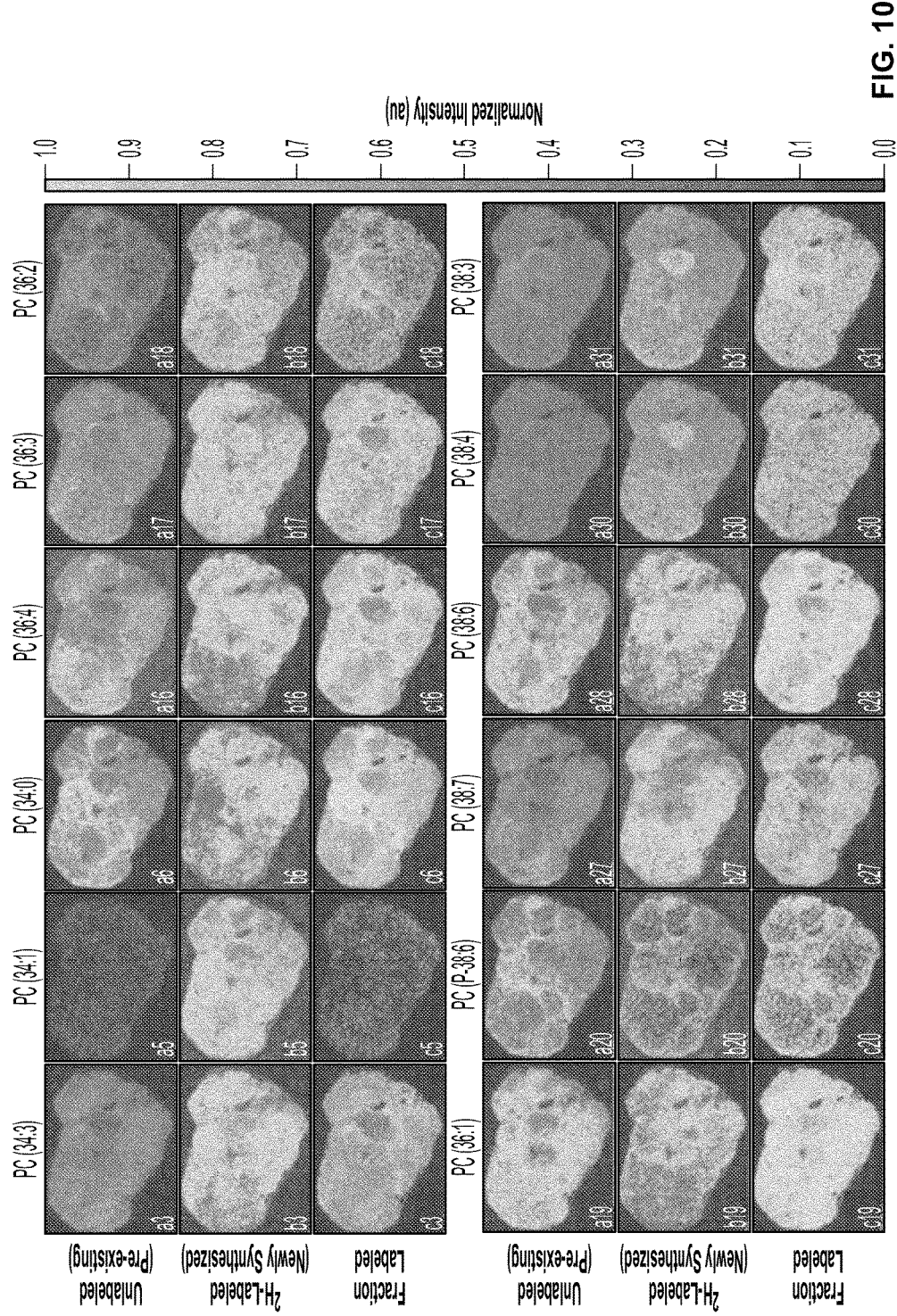
FIG. 10 depicts intensity images for twelve selected phospholipids where each column represents a unique lipid and the three rows in each panel are top: unlabeled (pre-existing); middle: $^2$H-labeled (newly synthesized); and bottom: fraction labeled ($^2$H-labeled/Total) (relative amounts of new versus pre-existing lipid levels), where image subscripts are provided to link to the comprehensive list of compounds characterized in Example 5.

Conversion of the resulting mass spectrometry data into metabolic flux data corresponding to spatially-defined locations of the sample can be accomplished by a computer processor with software that processes the relative abundance of mass isotopomers across the spatially-defined locations of the sample. For example, the kinetic images of lipid flux patterns for individual lipids (as shown in FIG. 10) were generated based on the relative contribution of the $^2$H-labeled vs. unlabeled population in the measured spectra for each pixel. SPIF can be used as a model for isotopic enrichment to calculate the total summed intensity in the measured spectra resulting from all isotopologues arising from each individual lipid, in either the $^2$H-labeled or unlabeled form. With reference to FIG. 10, all intensity values for each lipid (shown by the color bar) are normalized to the same value.

In some embodiments, the resulting mass spectrometry data are converted into metabolic flux images. Each pixel of an image is an elemental unit that represents metabolic flux data. Each pixel is also addressable to a spatial location of the sample, with a known spatial relationship to the other pixels in the image. The spatial location of a pixel in the image corresponds to the metabolic flux rate data of volatile molecules in a corresponding spatial location of the sample. In one embodiment, the metabolic flux image displayed may be the same size as the actual sample. In other embodiments, the metabolic flux image displayed may be smaller or larger than the actual sample. The image may be two-dimensional or three-dimensional. Analysis of serial sections from a sample allows assembly of three-dimensional metabolic flux images of a tissue.

In one embodiment of flux imaging, the relative abundances of mass isotopomers or the pattern of mass isotopomer abundances detected can be characterized down to a pixel-by-pixel basis across the spatial locations of the sample. In one embodiment, mass isotopomers are quantified for individual but more often a plurality of ion envelopes representing biomolecules of interest and analyzed by mathematical algorithms and software programs that are described herein. The pixel-by-pixel changes in mass isotopomer abundance patterns induced by the preceding in vivo metabolic labeling protocol reveals information about the spatially-localized kinetics or metabolic flux of each biomolecule detected as an ion envelope. For example, one to dozens, hundreds or thousands of volatilized molecules can be monitored as a metabolic flux fingerprint or signature of a tissue sample, a specific area of the tissue, or to localize a flux signature to a specific area of the tissue.

The image of each molecule's kinetics can be displayed as a heat map or a topologic map of the sample or other visualization techniques common to the art. In some embodiments, groups of molecules having similar kinetics across spatial coordinates are collapsed into a single representative image. In some embodiments, the mass analyzer can monitor one to thousands of molecules for each pixel, and each molecule monitored can be mapped and displayed as a separate image. The patterns or ratios of a plurality of molecules can also be mapped and displayed.

In one embodiment, overlaying images of the same section of a tissue preparation or from adjacent serial sections of the same tissue preparation, using other histopathologic methods known in the art, such as vital dyes, in situ hybridization, or immunohistochemistry, to correlate metabolic fluxes and functional processes based on their shared spatial coordinates with specific cell types, subcellular organelles, molecular aggregates or other known morphologic features of a tissue.

In other embodiments, the output of metabolic flux data corresponding to spatially-defined locations of the sample with known spatial relationships may be in the form of a table or a database.

The output generated according to the methods described herein represents kinetic data corresponding to known spatial coordinates of the sample analyzed. The methods and software described herein permit the visual representation of data as functional metabolic processes, in the form of heat maps, contour maps or other images by spatial coordinates in a biologic tissue or cell preparation. By way of examples, said images may include, for example, the spatial topology of mitochondrial lipid synthesis in muscle cells; of the spatial distribution of prostanoid and eicosanoid turnover in inflammatory infiltrate tissues; of the pattern of lipogenesis in biopsies of cancer or precancer, and the presence of functional hot spots within a tumor; of the topology of hormonal synthesis in an endocrine tissue; for the presence of autonomous functional areas; for localization of regenerating cells and cell membranes, in a tissue, as in peripheral neuropathies; for the identification of spatially-localized timed biosynthetic events in a tissue based on calculated precursor pool enrichments; and many other means of representing the dense information generated about metabolic fluxes in space and time.

In some embodiments, the methods and software can make use of univariate and multivariate statistical algorithms such as the analysis of variance, k-means clustering, principle component analysis, non-negative matrix factorization, and other approaches known to the field to grouping patterns of similar molecular distribution patterns and flux distributions patterns.

In some embodiments, the methods and software can also use mass difference alone or in conjunction with spatially varying patterns to resolve and identify adducts, degradation products, and multiple charge states for molecules. Molecules which can be monitored include molecules such as sugars, polysaccharides, lipids, metabolites, proteins, enzymes, nucleotides, etc.

In one embodiment, analysis of serial sections from a sample (such, for example, as a tissue specimen) allows assembly of three-dimensional metabolic flux images of a tissue. Static histochemical images of the same tissue section or of adjacent tissue sections can be generated and overlaid on the spatial coordinates of the metabolic flux maps, to link metabolic fluxes to specific cell types, subcellular structures or other standard histologic features. In cases where the individual isotopomers cannot be resolved either due to the mass analyzer resolution, but more typically for large ions such as biopolymers detected by MALDI, it is possible to detect alterations in flux by shifts in the average mass of ions of interest.

Implementation of Mass Spectrometry Analysis on a Computer Hardware Platform

Figure 25:
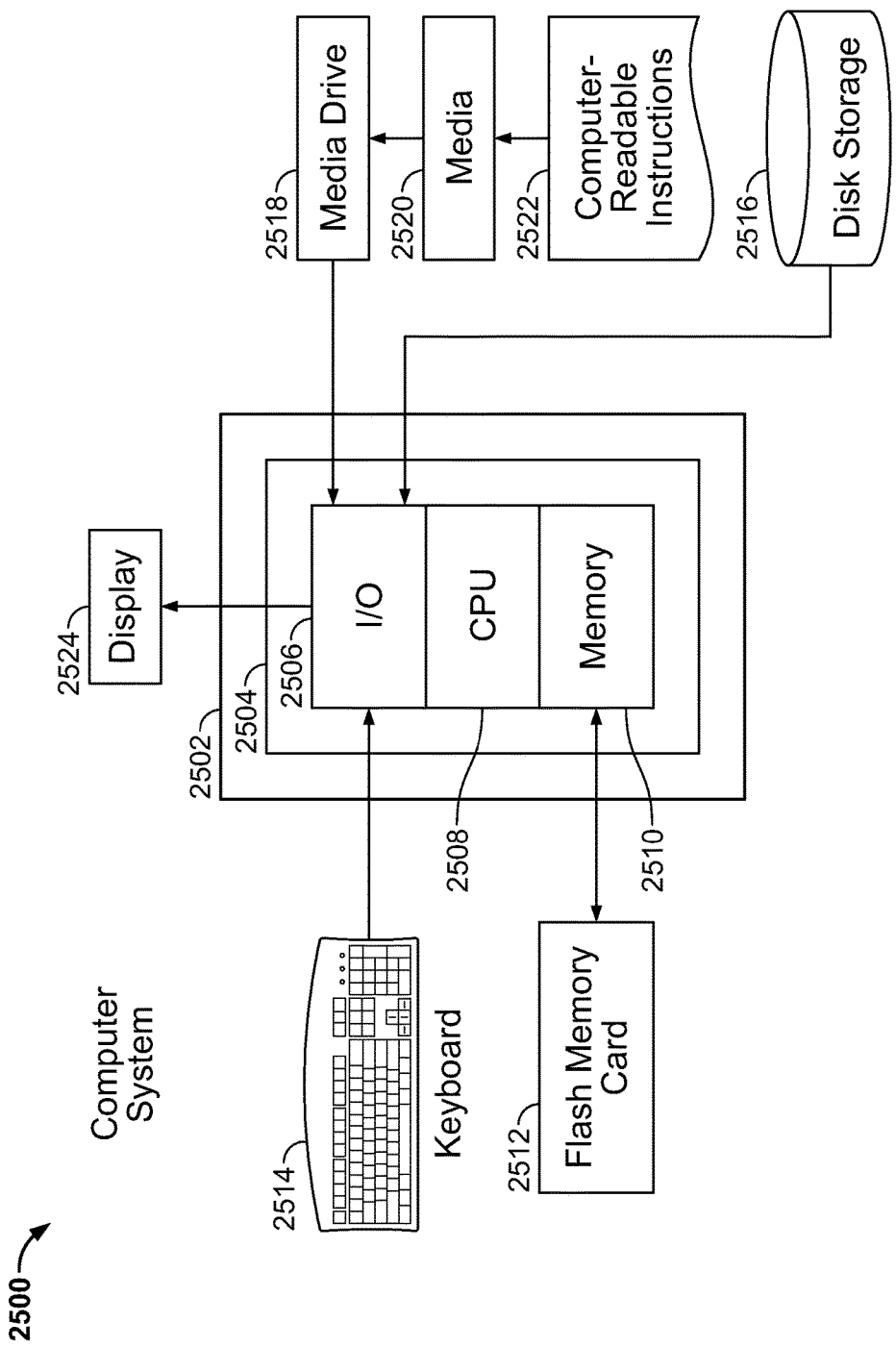
FIG. 25 depicts an exemplary computer system.

The methods described herein for processing the mass spectrometry data and determining molecular flux rates can be implemented in the form of computer software (computer-executable instructions) executed on a computer. FIG. 25 depicts an exemplary computer system 2500 configured to perform, for example, spectral peak finding, data loading, and chemical formula generation using algorithms for isotopic pattern generation, and/or algorithms for optimization and fitting isotopic patterns. In this context, computer system 2500 may be a general-purpose computer including, for example, a processor, memory, storage, and input/output devices (e.g., monitor, keyboard, disk drive, Internet connection, etc.). However, computer system 2500 may include circuitry or other specialized hardware for carrying out some or all aspects of the processes. In some operational settings, computer system 2500 may be configured as a system that includes one or more units, each of which is configured to carry out some aspects of the processes either in software, in hardware, or in some combination thereof. For example, in some embodiments, the analysis of the mass spectrometry data (as described above) may be computed on parallel computer processors or performed on separate computer systems.

FIG. 25 depicts a computer system 2500 with a number of standard components that may be used to perform the above-described analysis. The main system 2502 includes a motherboard 2504 having an input/output ("I/O") section 2506, one or more central processing units ("CPU") 2508, and a memory section 2510, which may have a flash memory card 2512 related to it. The I/O section 2506 is connected to a display 2524, a keyboard 2514, a disk storage unit 2516, and a media drive unit 2518. The media drive unit 2518 can read a computer-readable medium 2520, which typically contains computer-readable instructions 2522 and data.

At least some values based on the results of the data analysis can be saved for subsequent use. For example, the outputs of the system, including any tables, databases or images, can be saved directly in memory 2510 (e.g, RAM (Random Access Memory)) or another form of storage, such as disk storage 2516. Additionally, values derived from the data analysis, such as molecular flux rates, can also be saved directly in memory.

Additionally, a non-transitory computer-readable medium can be used to store (e.g., tangibly embody) one or more computer programs for performing any one of the above-described analyses by means of a computer. The computer program may be written, for example, in a general-purpose programming language (e.g., Pascal, C, C++) or some specialized application-specific language.

Applications of the Methods and Systems Described Herein

Given that control over biological processes is generally exerted as rate control, by the regulation of catalytic reactions and the partitioning of molecules through competing pathways, metabolic fluxes directly reveal the activity of functional processes and pathways in a tissue and often have functional significance in their own right. Accordingly, these in situ histopathologic images or spatial maps of metabolic processes represent the first example of "functional microscopy": spatially-localized displays of activities of functional processes, often with intrinsic physiologic or pathogenic significance, mapped on a spatially defined basis throughout a heterogeneous tissue. Because of the information density and spatial definition of the metabolic flux data produced, biologically or medically heterogeneities useful information can be learnt from metabolic flux patterns that are observed within a tissue, such as regions of increased or reduced metabolic fluxes (e.g., hot spots and cold spots), regions that differ or are similar for metabolic fluxes, complex signatures of metabolic fluxes for multiple molecules, complex patterns or gradients of metabolic fluxes for specific cells, organelles or structures, or other quantitative parameters related to the metabolic fluxes detected. Specifically, unique functional information about a tissue can be inferred from spatially-identified and patterns of dynamic processes (e.g., the degree of heterogeneity, reflected in kinetic hot spots and cold spots; the ratios of different molecular flux rates in selected areas of the tissue; regions of the tissue that are metabolically linked; shared or differing metabolic precursor pools; etc.), providing potential signatures of each individual's disease phenotype that have prognostic or therapeutic significance. Spatially-identified heterogeneities and patterns of dynamic processes can also focus more in-depth further analysis to specific regions of the tissue (e.g., to hot spots or cold spots) or to molecules or metabolic pathways that are identified as being altered and of interest.

Traditional (static) histpathology often incorporates spatial characteristics of a histologic tissue specimen in the diagnostic criteria and descriptions used for classifying diseases. Examples of spatial features commonly used in traditional histopathologic diagnosis include characteristics shown in Table 1 below.

TABLE 1

Spatial Characteristics Commonly Used in Traditional Histopathologic Diagnosis and Disease Classification

| Characteristic | Common Descriptors (Example) | Disease |
| --- | --- | --- |
| Pattern (Evenness) | Nodular, follicular vs diffuse | Lymphoma |
| | Focal, segmental vs zonal | Heptaic necrosis |
| | Cribriform (sieve-like) | Carcinoma of breast |

TABLE 1-continued

Spatial Characteristics Commonly Used in Traditional
Histopathologic Diagnosis and Disease Classification

| Charac-teristic | Common Descriptors (Example) | Disease |
|---|---|---|
| Geography (Location) | Peripheral vs. central | Necrosis of liver |
| | Circumferential | Giant cell arteritis |
| | Medial | Vessel wall necrosis |
| | Multi-centric, multiple | Adenomatous neoplasia |
| Enclosure (Topology) | Encapsulated | Neoplasia |
| | Cystic | Kidney; lung |
| | Islands | Pancreas; tumors |
| Regularity (Organization) | Irregular, disorganized | Tumors; granuloma tissue |
| | Eccentric | Atheromatous plaque |
| | Parallel | Fibrotic bands, fibroma |
| Shape | Discoidal, wedge-shaped | Infarcts (spleen) |
| | Onion-skinned | Vascular stenosis |
| Fullness (Emptiness) | Congestion | Lung, liver |
| | Lacunae (empty spots) | Brain, cancers |
| Variegation | Swiss cheese | Endometrial hyperplasia |
| | Monotonous | Chronic lymphocytic leukemia infiltrates |
| Borders (Margins) | Infiltrating, dissecting, intercalating | Tumors, aneurysms |
| | Junctional | Kidney |
| | Interlacing | Keloid collagen |
| Placement | Ectopic | Cardiac position, lipids |
| | Metastatic | Cancer |

Thus, a metabolic flux histopathologic report might describe spatial features of functional process from displayed images as follows, with diagnostic or therapeutic implications: e.g., "a circumferential zone of impaired myelin synthesis around a core of rapid myelination, indicating poor blood flow and carriage of the drug in this region of white matter"; or "an uneven, follicular pattern of reduced autophagic flux activity in the tumor consistent with early emergence of multiple resistant clones"; or "infiltrating regions of high caspase protein turnover and mitochondrial phospholipid breakdown spreading from peri-arterial zones in the liver, consistent with a spreading, blood-borne process" or "multi-centric islands of cholesterol synthesis in the atheroma suggesting impaired uptake or access of the drug to regions of the vessel wall"; or, "ectopic lipid synthesis in the peroxisomal region of the cell indicating a genetic variant"; or "a wedge-shaped area of cell membrane lipid deposition, nuclear membrane lipid synthesis and cell membrane TGF-beta receptor synthesis, indicating recovery from a recent vascular event"; and so on.

When overlaid with traditional histopathologic markers, metabolic flux maps and images can reveal cell-specific or subcellular structure-specific functional information throughout a tissue. Interrogation of tissue specimens collected from patients or animals with conditions such as cancer, inflammation, neurologic disorders, immune diseases, infections, fibrotic diseases, diabetes, obesity, arteriosclerosis, endocrine disorders, etc. for functional metabolic flux mapping and metabolic flux signatures thereby provides a novel and powerful tool for characterizing the phenotype (behavior, prognosis, pathogenic sub-class, optimal treatment strategy, response to ongoing treatment, etc.) for a tissue or disease.

In essence, then, metabolic flux microscopy combines spatial defined patterns of change in mass isotopomer abundances of ions to reveal metabolic fluxes (rates of dynamic biochemical processes in the dimension of time), while the spatially defined patterns of metabolic fluxes thereby calculated reveal information about the topology and morphology of functional processes in a tissue (distribution of metabolic fluxes in histopathologic space). This combination of information about time and space is unique in microscopy and biochemical diagnostics. The spatial metabolic flux "fingerprint" in a tissue can be correlated with clinical outcomes, genes, likely response to specific therapies, target modulation, or other biomarkers. The information density of metabolic flux microscopy results requires advanced data analysis and informatics techniques and brings histopathology into the information age.

Numerous applications in medical or veterinary diagnostics, companion diagnostics, drug discovery and development and biologic research are evident, and are described here. These include functional histopathologic display and mapping in disease tissues such as cancer, fibrosis, inflammation, metabolic disorders, atherosclerosis or neuropathology, for diagnosis, therapeutic targeting, patient stratification and personalized medicine. In particular, kinetic signatures or fingerprints in a tissue can be correlated with disease behavior or treatment response, for use in medical or veterinary disease management or in medical diagnosis and companion diagnostics.

Biomedical applications of in situ metabolic flux microscopy, include for example functional imaging of histopathology in disease tissues, such as cancer, fibrosis, inflammation, metabolic disorders, neuropathology, for spatial inhomogeneities that reveal areas of increased or reduced rates of a functional process (hot spots or cold spots, respectively), for diagnosis, therapeutic targeting, patient stratification or personalized medicine. Specific applications, for example, mapping cholesterol turnover in the core of an atherosclerotic plaque in a blood vessel, and the capacity of a high-density lipoprotein treatment to mobilize cholesterol from the core of a plaque; imaging autophagic pathways fluxes based on the turnover of proteins or peptides derived from proteins that are autophagic substrates, in a different regions of a cancerous tissue, neurologic tissue, or muscle tissue; displaying lipid synthetic fluxes or structural protein synthetic fluxes in different cellular compartments of muscle tissue from a sarcopenic or cachectic subject, including cardiolipin turnover in mitochodria, fatty acid synthesis and turnover in myocytes and in the extracellular space, as a biomarker of muscle quality or response to treatment; measuring the turnover of aggregated proteins, such as amyloid beta in Alzheimer's plaque, huntingtin or alpha-synuclein in neurodegenerative diseases, or of cellular storage granules, such as insulin in pancreatic beta cells; monitoring loss of labeled palmitate, glucose or other energy substrates from oxidative tissues like skeletal muscle or failing heart, as a marker of fuel utilization by specific cells in a tissue; visualizing myelin synthesis in the central or peripheral nervous system, in settings of demyelination, neurodegeneration or neuropathy; displaying the turnover of cell membrane receptors in disease states such as the epithelial sodium transporter in hypertension or the CFTR in bronchi in cystic fibrosis, LDL cholesterol receptor turnover in tissues from hyperlipidemic subjects and in response to lipid-lowering agents; metabolic conversion of steroid hormones to their active forms and target sites in a target organ, such as testosterone reduction to dihydrotestosterone in prostate tissue or muscle specimens and the effect of dihydrotestosterone inhibitors.

In situ metabolic flux microscopy may also be used for functional imaging (metabolic flux microscopy) of disease tissues, such as cancer, for kinetic signatures correlated with disease behavior or treatment response, for use in medical or veterinary disease management or in medical diagnosis and companion diagnostics. Specific applications include, for example, mapping lipid metabolic fluxes and protein turnover across cancer tissue slides, to identify hot spots and heterogeneity, as a marker of cancer aggressiveness or response to treatment; measuring lipid flux patterns in tissues potentially exhibiting lipotoxicity, such as muscle, pancreas and liver, to identify metabolic flux fingerprints associated with insulin resistance or diabetes risk; imaging patterns of lipid turnover in areas of skin in subjects with eczema or psoriasis as signatures of disease behavior or likely response to treatments, including response to cosmetic treatments; monitoring the patterns of transport of cargo proteins along neurons in different areas on the brain in neurodegenerative diseases; and many others apparent in the art.

The present invention may also be used for determination of the timing of spatially-localized kinetic processes, such as embryologic or other developmental events, by imposition of timed precursor label administration or a temporal gradient of precursor label administration, and displaying precursor pool enrichments for molecules in different locations within a tissue; determination of biosynthetic origins or metabolic sources of molecules in spatially-localized regions of cells (e.g., identifying the tissue or subcellular origin of transported molecules); or characterization of subcellular functional organization—for example, kinetic processes in subcellular organelles, lipid droplets, storage granules, secretory vesicles, endoplasmic reticulum, etc.—as a tool for understanding the in vivo regulation and control of metabolic flux in a tissue.

EXAMPLES

The following Examples are merely illustrative and are not meant to limit any aspects of the present disclosure in any way.

Example 1: Integration of Deuterium Isotopic Labeling with Nanostructure-Initiator Mass Spectrometry (NIMS)-Based Metabolite Imaging Technology to Generate Histochemical Flux Images Here we propose a novel integration of nanotechnology based mass spectrometric tumor imaging, with mass isotopomer quantitation and kinetic analysis after deuterium label incorporation, with the goal of quantifying fluxes directly within the 3D architecture of the tumor and the microenvironment. This overcomes critical challenges in the field by directly measuring metabolic phenotypes within the physiological context.

In vivo approaches for characterizing the molecular dynamics of complex biochemical networks, based on the internal patterns of incorporated labels have been developed, tested and extensively validated. See Hellerstein, M. K. and R. A. Neese, *Mass isotopomer distribution analysis at eight years: theoretical, analytic, and experimental considerations*. American Journal of Physiology—Endocrinology And Metabolism, 1999. 276(6): p. E1146. By using basic kinetic principles, the generation of these isotopically labeled metabolites can be monitored in vivo to measure metabolite dynamics. Integration of NIMS, with mass isotopomer quantitation and kinetic analysis after label incorporation, with the goal of quantifying fluxes directly within the 3D architecture of the tumor and the microenvironment to provide an additional dimension of how low-dose radiation alters metabolic flux within cells, biofluids and tissues. This method will be used to image mammary glands and tissues to detect rapidly growing cell populations that can be linked to adaptive response and genetic controls. It will also be used to investigate morphogenesis by pulsing the stable isotopic label into the media and determine when cells are made based on label incorporation.

Identification of Abundant Lipids to Support Flux Analysis.

We will establish proof of concept in mouse breast cancer models for the spatial measurement by NIMS of mass isotopomer patterns of lipid metabolites in histopathology specimens. Lipids have been selected as the target class of metabolites for flux analysis given their central role cell growth, signaling, proliferation, physiologic processes related to neoplastic behavior, diversity, the compatibility of hydrophobic materials with NIMS[33] and suitability of lipids for flux analysis [34].

Labeled MDAMB231 xenograft tumors and C(3)1/Tag transgenic mice will be generated for these studies. These studies will utilize 8 Individual C3(1)/Tag tumors provided by Jeffrey E. Green, M.D. (NCI) and 8 individual mammary glands from 10 wk old FVB/N mice snap frozen and stored at −80 C. These will be lyophilized (Lab Conco Freezone 2.5), homogenized (Biospec Products Mini-Beadbeater-96), extracted using 2:1 chloroform: methanol on ice, pelleted, and the supernatant dried (Savant: Speed vac plus SC110A) and resuspended in 200 µL of 1:2:2 water:methanol:isopropanol.

NIMS Surface Preparation:

The preparation of nanostructure-initiator mass spectrometry (NIMS) surfaces has been described in detail elsewhere in Woo, H., T. Northen, O. Yanes, and G. Siuzdak, *Nanostructure-initiator mass spectrometry: a protocol for preparing and applying NIMS surfaces for high-sensitivity mass analysis*. Nature Protocols, 2008. 3(8): p. 1341-1349 and in U.S. Patent Publication No 20080128608. Briefly, a 4" silicon wafer (single-sided polished P/Boron, orientation ⟨1-0-0⟩, resistivity 0.01-0.02 Ωcm, thickness 525±25 µm) obtained from Silicon Quest International (Santa Clara, Calif.) was cut into a 70×70 mm square, washed in Piranha solution (sulfuric acid/hydrogen peroxide), and etched with 25% hydrofluoric acid in ethanol in a custom made Teflon etching chamber under constant current of 2.4 A for 15 min. After etching, chips were coated with 400 µl of initiator liquid (bis(heptadecafluoro-1,1,2,2-tetrahydrodecyl)tetramethyl-disiloxane) purchased from Gelest (Morrisville, Pa.).

NIMS Analysis:

0.5 ul of tissue extract will be spotted with 8× independent replicates on the NIMS surface. Analysis will be performed on a 5800 TOF/TOF mass analyzer system (AB Sciex; Foster City, Calif.) in positive and negative reflector mode. The third harmonic of a Nd:YAG laser (355 nm) will be used at a repetition rate of 200 Hz with 8-15 shots per spot, laser intensity 2500-3200, delay time 150-300 ns to acquire a full mass spectrum ranging from 50 to 2,000 m/z. Tandem mass spectrometry will be performed on all major ions using a 2 KV potential.

LC/MS-MS Analysis:

We have observed that the TOF based MS is inherently more accurate in the measurement of isotopomer patterns than other MS instruments (e.g., Orbitrap). Identification of components within the extracted lipid solution will be performed to support NIMS identification using a Zorbax C18 column with 5 µm particles at a flow rate of 20 µl/minute. Data will be collected using an Agilent ESI-QTOF using rapid polarity switching and a capillary voltage of 4000 V, nebulizer at 25 psi, drying gas at 3.6 L/min, m/z range 50-1500. Custom software written in the MATLAB programming language will be used to define features within each sample and compare them across samples. All major ions will be subjected to fragmentation (10, 20, and 40 eV).

GC/MS Analysis:

Methods will be used as described previously in Hellerstein, M. K. and R. A. Neese, *Mass isotopomer distribution analysis at eight years: theoretical, analytic, and experimental considerations*. American Journal of Physiology-Endocrinology And Metabolism, 1999. 276(6): p. E1146, hereby incorporated by reference in its entirety. Basic lipid kinetics (cholesterol, fatty acids, phospholipids, etc.) will be compared, for confirmation, in tissue extracts.

Lipid Identification:

All MS/MS spectra will be searched against Metlin, MassBank, Theoretical Lipid MSMS databases, and Riken databases for identification to construct a Metabolite Atlas [28]. Lipid standards will be obtained when possible for abundant lipids detected using NIMS and identifications will be confirmed based on comparison of fragmentation patterns and retention times.

Measuring Dynamics of Lipid Metabolites in Healthy Mice.

We will establish the kinetics for optimal labeling of abundant mammary gland lipids identified, determination of the number of hydrogen atoms actively incorporated from body water, and the data handling and analysis algorithms necessary for kinetic histochemistry of human tissues. We will compare GC/MS and LC/MS-MS measurements of lipids from tissue regions of interest identified kinetically by NIMS, to validate the NIMS imaging method. The use of LC/MS-MS & GC/MS to validate the NIMS analysis is only applicable to metabolites which are homogeneously distributed across the tissue of interest; therefore as described below, laser capture microdissection will be used to isolate these cell populations.

We expect to see a similar diversity of rates among the lipids and small molecules. Therefore, 16 10 old female FVB/N mice will be initiated with a bolus injection of 0.035 mL $^2H_2O$ saline per gram of body mass, followed by uniformly 8% molar percent excess (MPE) enriched drinking water and mammary glands will be collected from a time course of FVB mice labeled at 8 time points (2 mice/time point) 1 hr, 4 hr, 12 hr, 1 day, 2 days, 4 days, 8 days and 12 days. This labeling regime will result in body water enrichment 4-5% for duration of the experiment. Body water $^2H_2O$ enrichments are determined by direct measurement of deuterium mole percent excess (MPE) in water distilled from the blood serum. Body water enrichments are measured against a $^2H_2O$ standard curve using laser water isotope analyzer (LGR, Los Gatos Calif.) according to Lis, G., L. Wassenaar, and M. Hendry, *High-precision laser spectroscopy D/H and 18O/16O measurements of microliter natural water samples*. Analytical chemistry, 2008. 80(1): p. 287-293, hereby incorporated by reference.

Tissue Collection and Staining:

Prior to collection of tissue, mice will be anesthetized using carbon dioxide gas. Tissue will be collected and snap frozen in dry ice super cooled 2-methyl butane. Sum thick frozen tissue sections will be prepared using a CM3050S Cryostat from Leica Microsystems (Bannockburn, Ill.) and serial sections will be placed directly on NIMS surfaces and glass slides for staining using established protocols as described in eindl, W., B. P. Bowen, M. A. Balamotis, J. E. Green, and T. R. Northen, *Multivariate analysis of a 3D mass spectral image for examining tissue heterogeneity*. Integr. Biol., 2011. 3(4): p. 460. Briefly, the mouse mammary tumor is dissected from a 5 month old female C3(1)-SV40T/t-antigen transgenic mouse in the FVB/N background and immediately frozen on dry ice. The tissue is subsequently stored at −80° C. until further use. Sectioning of the tissue is carried out on a CM3050S Cryostat from Leica Microsystems (Bannockburn, Ill.). Sections were cut directly from frozen tissue at a thickness of 7 µm. For imaging mass spectrometry a total of 30 sections are cut every 28 µm in the z-direction and thaw-mounted onto the mass spectrometry surface, so that a tissue thickness of ~1 mm is covered. Additionally, in each case two more 7 µm sections directly following the sections used for mass spectrometry are thaw-mounted onto glass slides and used for H&E and Oil Red O staining, or any other type of histopathology staining.

One set of sequential sections is subjected to hematoxylin and eosin (H&E) staining. To this end, sections are fixed in 10% formalin (Azer Scientific; Morgantown, Pa.), followed by staining with Mayer's hematoxylin solution (Dako; Carpinteria, Calif.), transfer into 80% ethanol, and staining with eosin solution (VWR; West Chester, Pa.). After subsequent washes in 80% ethanol, 95% ethanol, 100% ethanol, and xylene, slides are mounted using Permount mounting medium (Fisher Scientific; Pittsburgh, Pa.). Another set of sections is stained using Oil Red O. Sections are first fixed in 10% formalin (Sigma-Aldrich; St. Louis, Mo.), transferred into 60% isopropanol, and stained with a 3 mg ml$^{-1}$ solution of Oil Red O (Sigma-Aldrich; St. Louis, Mo.) in 60% isopropanol. After rinsing with 60% isopropanol, slides are mounted with VectaShield mounting medium (Vector Labs; Burlingame, Calif.). For both staining, microscopy is performed on a MZ16 stereomicroscope and images are recorded on a DFC420 camera from Leica Microsystems (Bannockburn, Ill.).

Laser Microdissection will be used when necessary to isolate lipids for further analysis, e.g. for tandem mass spectrometry identification by isolating tumor cell populations for extraction and solution based NIMS or LC/MS-MS as described above. Tissue will be snap frozen in OCT cryopreservative solution (Sakura Finetek Corp), 10 micron thick cryosections are cut, and mounted on slides coated with a PET (polyethylene terephthalate) thermoplastic foil. Slides containing multiple tissue sections are then stained according to a modified hematoxylin and eosin (H&E) staining procedure that preserves sample integrity by minimizing the time spent at room temperature. Slides are then air dried, and immediately cut out using a Leica AS LMD system (Leica Microsystems, Allendale, N.J.). Slides are mounted in an inverted position on the stage, and a sample collection tube is placed directly under the tissue specimen and an ultraviolet laser is directed at the PET thermoplastic foil, and traces along the operator specified path until the region of interest is liberated from the slide, subsequently falling under the force of gravity into the collection tube.

NIMS and LC/MS-MS Analysis:

Mammary glands will be processed and analyzed as described above.

Figure 6:
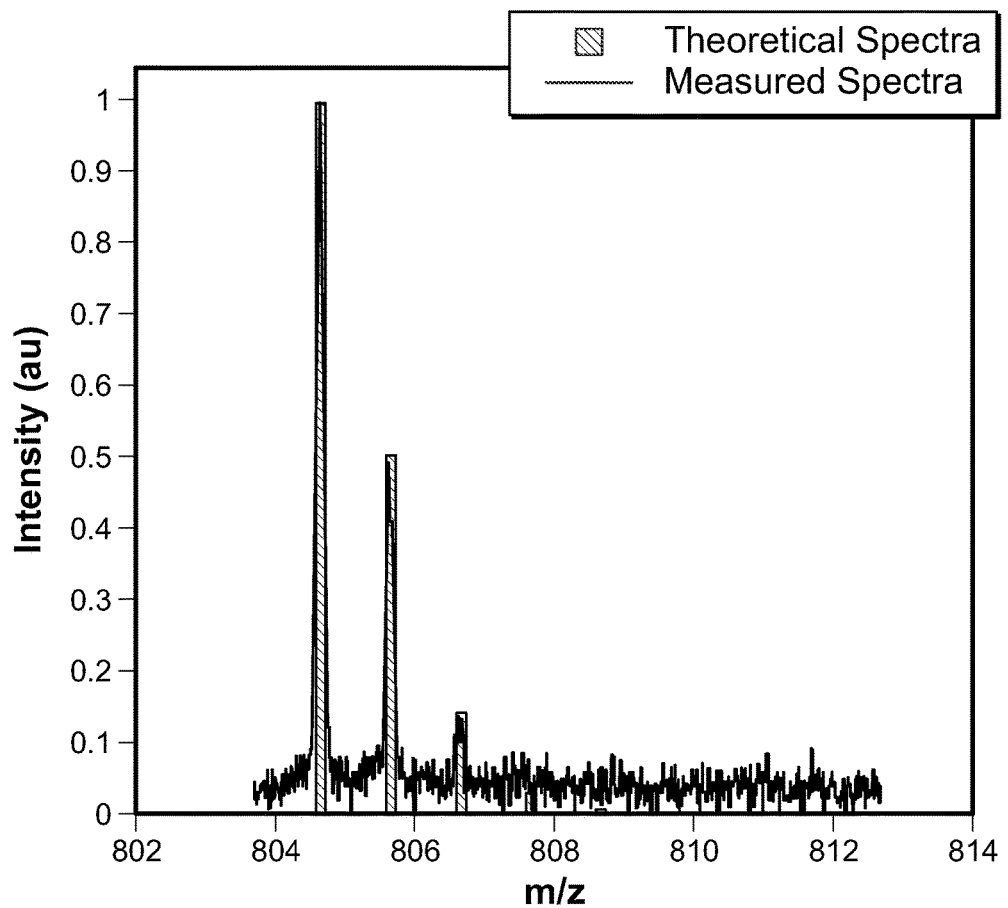
FIG. 6 depicts a NIMS spectrum comparing a lipid standard and the corresponding theoretical relative isotopic pattern to verify that NIMS ionization and detection was capable of sufficient linearity for the experiment in Example 1.
Figure 8B:
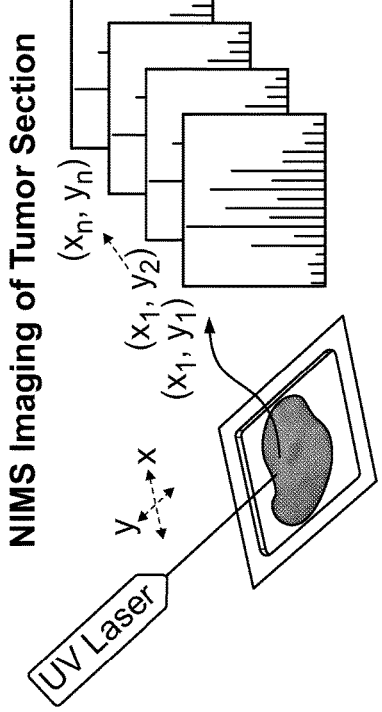
FIGS. 8A-8D depicts an exemplary workflow for using kMSI to define the spatial heterogeneity of lipid composition and biosynthesis.
Figure 8D:
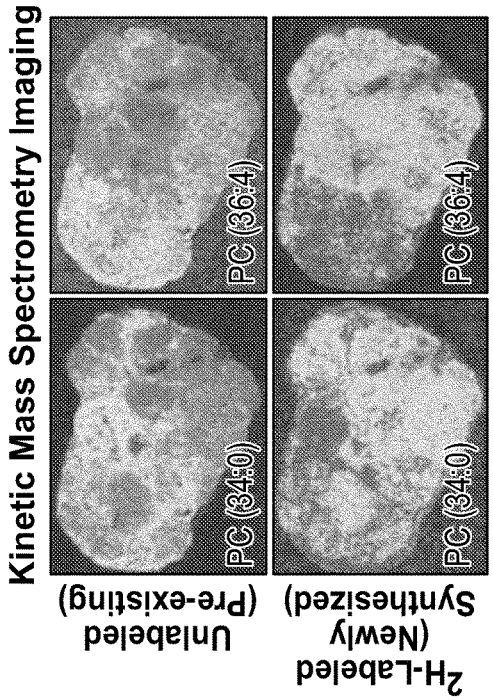
Figure 8A:
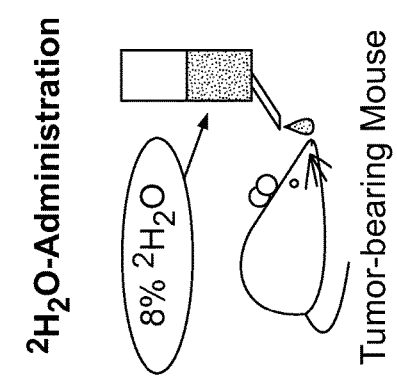
Figure 8C:

Isotopomer Analysis:

The Mass Isotopomer Distribution Analysis (MIDA) algorithm[26] is based on time dependent change in the relative intensities of isotopic masses within the mass spectrum. For determination of n and percent maximal labeling, elemental composition (i.e., chemical formula) is the key variable, the chemical structure is only important for later biological interpretation of the turnover rates. Fractional synthesis calculations are based on the enrichment of the precursor population (p) and the total possible number of isotopic labels (n) that can be incorporated into a biomolecule. Importantly, p matches the enrichment of the body water (Busch et. al. 2006 [40]) allowing us to accurately measure this variable throughout the experiment. The total possible number of isotopic labels (n) that can be incorporated into a biomolecule cannot be quantified a priori as it depends upon which covalent C—H bonds equilibrate with the solvent in the biosynthetic pathway. Palmitate, for example, has 32 total hydrogens, 31 of them are involved in covalent C—H bonds, while experimental analysis measured an n=22[34]. We and others[38] have experimentally defined the n for each amino acid allowing us to generate a unique n for the analysis of every peptide we observe. For a given peptide, n is the sum of the individual amino acid n's. The plateau value can then be calculated as a function of n and p (FIG. 6). Working with mice we have the advantage of fast metabolic turnover. After one year, we estimate that >90% of the tissue will have turned over, generating metabolites labeled to the maximal possible value (n) [39]. Accurate measurement of the isotopomer pattern will allow n to be derived experimentally for lipids within this experiment.

Kinetic Calculations:

Fractional synthesis (f) is the ratio of newly synthesized protein/metabolite within the total protein/metabolite pool [38, 40]. The change in the distinct pattern of the individual mass isotopomers is unique for a single n and percent fractional synthesis. In the mouse experiment, a bolus of labeled water ensures that the body water enrichment reaches plateau within less than an hour, therefore simple single pool kinetics can be used to calculate the fraction of newly synthesized molecules at any timepoint.

At the isotopic enrichments of p used in this study (1-5%), labeled and unlabeled metabolite populations have m/z ranges that overlap. In a mixed pool (i.e, for fractional syntheses between 0-100%), deconvoluting the two subpopulations can be accomplished by calculation of the relative change in the isotopic intensity. Each isotopomer is normalized according to the total intensity of the isotopomer envelope, typically 4 masses M0-M3. In this study, we base our calculations for f upon the change in intensity of the normalized monoisotopic peak (EM0). In theory the shift in intensity of each isotope peak should reveal the same fractional synthesis. In practice, we find that the signal to noise is most favorable for the EM0, because of the larger intensity change for this isotopomer. GC/MS and LC/MS measurements of lipid metabolite mass isotopomer abundances and calculation of fluxes by MIDA will be performed on microdissected tissue samples, an area of active research in the lab (Hayes G, Misell L, Hellerstein M K, manuscript submitted, J Clin Oncol). The results of the NIMS experiment will be analyzed in the same fashion. Integration of isotopomer analysis with NIMS imaging allows determination and localization of fluxes within tissues as shown in Example 2.

Identification of Isotopic Patterns and Linearity of Intensity Using NIMS.

Figure 4A:
FIG. 4A depicts hematoxylin and eosin (H&E) staining image of tumor #458 in Example 5.
Figure 4B:
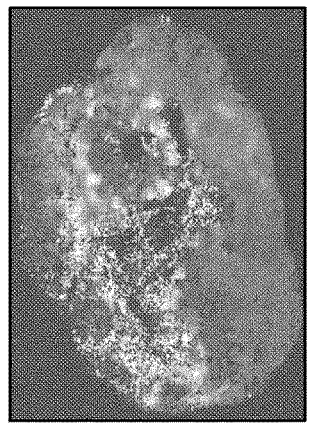
FIGS. 4B and 4C depict images from Example 5, corresponding to flux demonstrate the presence of both spatially heterogeneous flux and differences in flux for different metabolites (e.g., phospholipids with different fatty acid chain lengths.
Figure 4C:
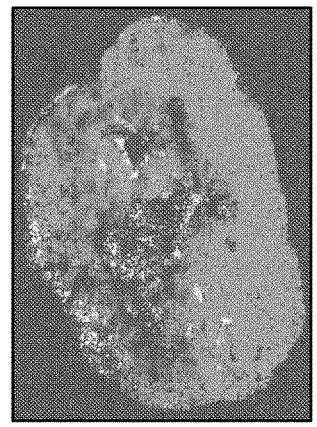

As is described above, time of flight based mass spectrometry offers a large dynamic range (up to 5 orders of magnitude) with a linear intensity (typically better than 1%). To ensure that NIMS based ionization and detection offers the same quality of data, lipid standards were profiled with NIMS. We typically use an isotopic fine structure estimation algorithm when working with high mass accuracy data, but for estimating the intensity of each isotopomer about a nominal mass value, convolution of the multinomial probability distributions for each element can be used, and for each value of n, the D/H ratio can be calculated. The chemical formula is rewritten as $C_iH^F_jH^4_kN_mO_nP_oS_q$. Where $H^4$ refers to the hydrogens that originate from water and $H^F$ refers to the hydrogens that originate from other nutritional sources (ie: carbohydrate, fat, and protein). By varying the isotopic enrichment for $H^4$, and keeping all the other elements at their natural isotopic abundance, convex optimization algorithms can be used to calculate the fractional enrichment in deuterium at the available sites of a specific molecule. As is demonstrated in FIG. 4, NIMS analysis and instrumentation is sufficient for isotopic pattern fitting described in the proposed work.

Kinetic-Histochemical Study of Cancerous Tissue in Mice.

This aim will establish proof of concept for flux imaging to differentiate metabolic flux in paclitaxel responsive and non-responsive tumors using two well characterized mouse models.

Briefly, MDAMB231 cells are injected into the fat pad of the NOD-SCID female mice as previously described by Borowsky et al. [44]. Each mouse will receive an injection of a sensitive or resistant clone of MDAMB231 into its inguinal mammary glands. Tumors appear within about a week after injection. Once measurable tumors are observed, a time course of labeling will be measured by collecting tumors at 1 Hr, 1 Day, and 3 Days after administration of $^2H_2O$. In the second system, tumors from FVB/N TgN [C3(1)T-Ag] mouse model (BTNBC) will be analyzed 4-6 months after birth. Tumors isolated from these mice can be categorized in three diagnostic groups; growth inhibited, unresponsive, and metastatic. There will be approximately 6 tumors from each group, and in both systems mice will be treated with 4.5 mg/kg paclitaxel QD×5 days and tumors will be collected for histological analyses (fixed in 4% paraformaldehye) and NIMS analyses (snap frozen) at 1 hr, 1 day, and 3 days with tumor harvesting at 5 days post drug administration. Once tumors are observed $^2H_2O$ will be administered as described in Aim1B using the time-point that should achieve an average enrichment of 50% in tumor lipids at day 1 post drug. Measurement of DNA enrichment over time as published previously (Misell 2005) will allow us to normalize lipid flux based on the cellular expansion of the tumor.

NIMS Flux Imaging:

Tumors will be harvested, immediately snap frozen, placed in OCT, sectioned, stained, imaged, and analyzed. Complete spectra will be collected at each x-y step-size of 25-75 µm using MALDI-MSI control software. All sections will be imaged with identical settings, and imaging data will be stored in the Analyze 7.5 data format (Mayo Foundation; Rochester, Minn.). Given the large size of the NIMS chips vs. the tumors, a minimum of one section of each diagnostic group will be placed on the same chip for direct comparison of fluxes in the three groups. NIMS data analysis Identification of differential fluxes for the growth inhibited, unresponsive, and metastatic tumors will be accomplished using existing custom software used to analyze the instruments raw binary file (10-40 GB) to compare lipid isotopomer ratios.

Outcome Based Design Changes to Aim 1:

TOF-SIMS analysis [9] will be used if higher resolution imaging is required to study small cell populations. For example, an entire TOF-SIMS image could fit into a single pixel in a typical NIMS image. In this case, tissues are sectioned as described for NIMS, with the exception that the frozen tissue is placed on an unetched silicon substrate. Preliminary results section shows that this approach can image deuterium incorporation into single-cells within mouse tissues with 200 nm resolution.

Example 2: Kinetic Histology of Mouse Tissue with NIMS

Figure 5A:
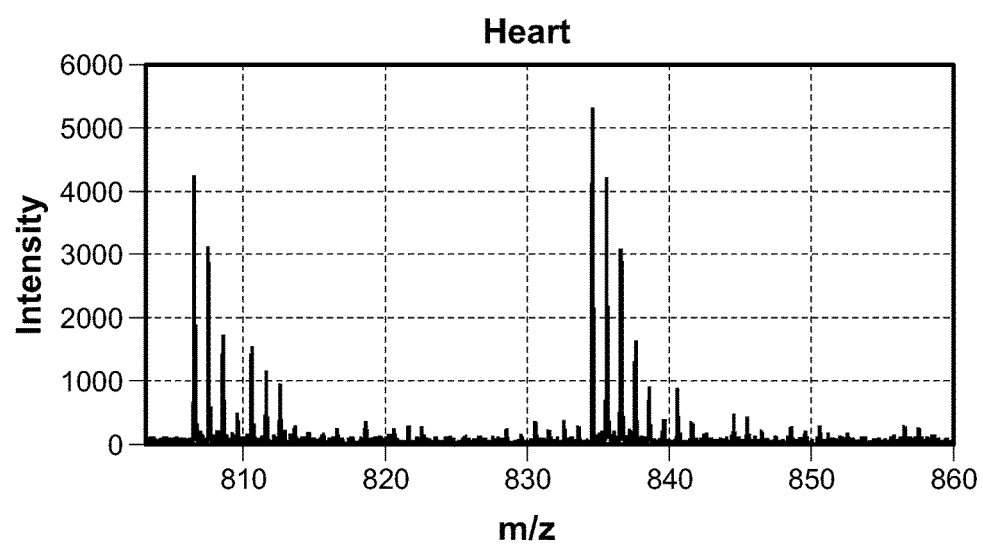
FIG. 5 depicts NIMS spectra to screen the classes of molecules present and the bulk labeling present in different tissues (5A—heart, 5B—kidney, 5C—liver and 5D—tumor) in Example 2. The various tissues have unique metabolite abundance patterns. It is clear that the tumor has the highest rate of synthesis of many compounds (e.g., lipids, gangliosides, carnitines).
Figure 5B:
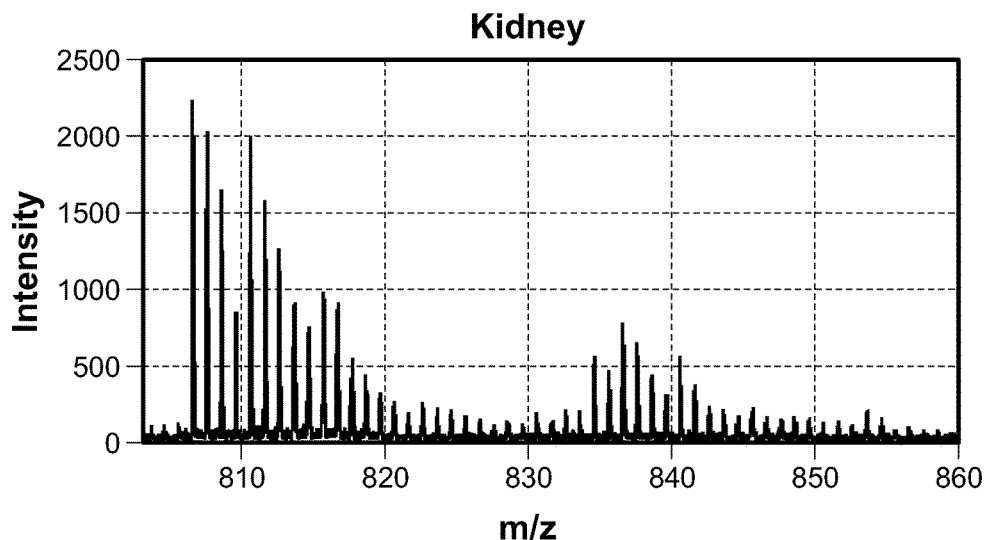
Figure 5C:
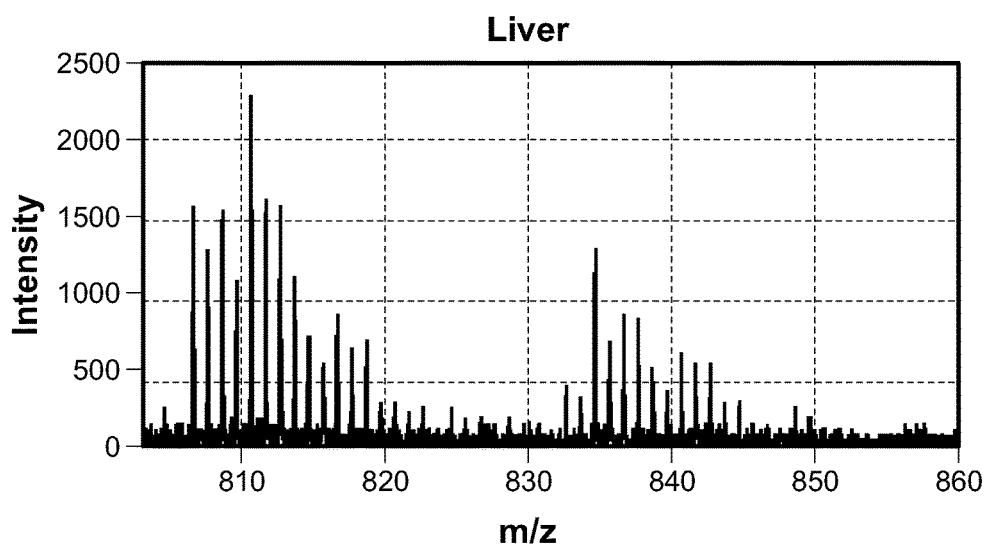
Figure 5D:
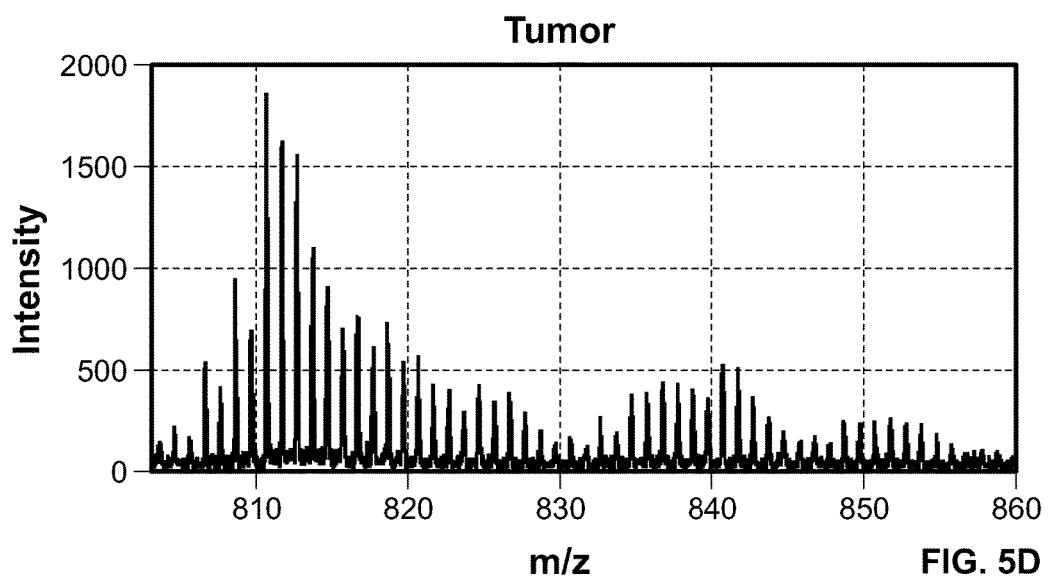

Whole mouse imaging has shown that there are complex metabolite patterns that can be imaged using NIMS over large areas. To determine the ability to image isotopomer abundance patterns and consequently determine the flux, dissected tissues from adult mice that were given 5% $^2H_2O$ for three days were sectioned and imaged with NIMS (FIG. 7B). For each pixel, numerous labeled metabolites could be observed. For example, phosphocholine was one of the dominant signals[37] in the TOF-SIMS imaging spectra. In the case of phosphocholine, there are 15 hydrogen atoms in C—H bonds. As can be seen in FIG. 7D, the ratio of M1/(M1+M0), or relative flux, increases over the course of 3 days of administration of $^2H_2O$. It can be calculated that there are 3 hydrogens that could be exchanged with deuterium in cellular water for phosphocholine. All of the other hydrogens are non-labile metabolically and come from nutritional-sources such as exogenous carbohydrates, lipids, and proteins. Knowing that n=3 for phosphocholine, the flux could be converted into an image (FIG. 5D). In the case that it is necessary to resolve sub-micron lipid flux, TOF-SIMS can be used to detect deuterium incorporation into hydrocarbon fragments.

Analysis of Human Tissue and Tumors.

We have explored tumor heterogeneity in preliminary experiments and described them in Reindl, W., B. P. Bowen, M. A. Balamotis, J. E. Green, and T. R. Northen, *Multivariate analysis of a 3D mass spectral image for examining tissue heterogeneity*. Integr. Biol., 2011. 3(4): p. 460, hereby incorporated by reference. Analysis of human tissue and tumors will be conducted measuring metabolic flux which will generate 3D topographic images similar to those described in Reindl et al., Integr. Biol., 2011. 3(4): p. 460 to study tumor heterogeneities.

Example 3: Flux Microscopy for Healthy Human Tissue

Determine Spatial Turnover Kinetics of Lipid Metabolites (Kinetic Histochemistry) in Healthy Human Tissue.

Here, we will validate existing clinical protocols and determine the clinically feasible time points for tissue collection that give useful lipid flux distributions using NIMS tissue imaging. Specifically, we will define the clinical $^2H_2O$ administration, sample handling, and analysis protocols by using relatively accessible human tissue samples to identify and overcome procedural and technical challenges. Compared to preclinical experimentation, human studies have a number of distinct challenges that affect the quantification of newly-synthesized metabolites in heavy water labeling studies. Different isotopic enrichments in the metabolic products compared to mouse tissues will almost surely result due to slower basal turnover rates, lower precursor pool enrichments ($^2H_2O$ % in body water), and time-varying labeling enrichment curves. Accordingly, the techniques that have been used in rodent studies require modification/optimization for clinical use.

Previous observations showed that the fractional synthesis of cholesterol is 1.3% per day in skin (data not shown). For labeling periods ranging from 1-4 weeks, this synthesis rate would result in 10-30% of cholesterol molecules being labeled. As we have seen, under labeling conditions achievable in human beings, this level of fractional synthesis can be successfully quantified by GC/MS and LC/MS. Accordingly, towards the goal of establishing NIMS in a clinical setting, we will enroll subjects for this aim to provide dermal punch biopsies.

Administration of $^2H_2O$:

Subjects will be given a supply of GLP $^2H_2O$ aliquots and asked to self-administer two doses daily. This will result is a 4-7 day ramp in $^2H_2O$ followed by a plateau enrichment at 1-1.5 MPE. Because this is applied to humans, this labeling strategy is slightly extended in time compared to that for the mouse (which was only 3-5 days), but minimizes the risk of $^2H_2O$ induced vertigo.

Clinical Sample Collection:

Two subjects will be enrolled and administered heavy water for 56 days prior to collection of two biopsies from each subject. Weekly salivette body water sampling as well as blood draws on the day of the biopsy will be used for verifying patient compliance by heavy water enrichment and for quantification of blood borne kinetic metabolites. Full-thickness cross-sectional sections of the punch biopsies will be processed, snap-frozen, and stored at −80 C as described in Aim 1.

Construction of Skin Lipid Atlas to Support Kinetic Studies.

As described in Aim 1, accurate chemical formulas are necessary for flux calculations, therefore the commercially available control skin will be lyophilized, homogenized, extracted, analyzed using NIMS, GC/MS and LC-MS/MS, and abundant ions on NIMS will be identified using tandem mass spectrometry. Two of the treated tissues will be identically processed for validation of bulk fluxes by comparison with flux images of lipids homogenously distributed in the tissues.

NIMS Imaging.

The labeled biopsies (4) will be placed in OCT, sectioned, and imaged as described above.

Validation of MIDA Variables:

Using the highly labeled lipids from the human skin we will calculate n values for observed metabolites, our expectation is that as we observed for peptides (data not shown) n values will be similar for most metabolites in both mouse and human.

Optimization:

In the event of low labeling, it is important to distinguish between patient compliance with $D_2O$ administration and the need for longer $D_2O$ administration. Weekly blood draws will be used to verify compliance with protocols, and if needed, the study will be repeated with a longer duration.

Measure Spatial Lipid Metabolic Fluxes within Normal Human Tissue.

We will experimentally define the maximal deuterium isotope label incorporation (n) for metabolites observed within human tissues. Use of multiple labeling time points will allow us to measure flux and metabolites with a wide range of rates. Regional areas exhibiting interesting lipid kinetics, as identified by NIMS imaging, will be validated by laser microdissection using GC/MS or LC/MS-MS.

Using the labeling method outlined above we will label three human subjects and collect time points of skin labeled at either 14 or 28 days, to generate a time course of NIMS-calculated kinetics.

$^2H_2O$ Administration:

Subjects will be enrolled following existing protocols and $D_2O$ will be administered as above.

Skin Biopsy Collection:

Tissues will be collected and processed as in previous example.

Flux Analysis:

Flux calculations for each analyte will be performed as described in Aim 1 with a correction incorporated for the time dependent change in enrichment (p). Using the body water enrichments measured in the saliva a model for calculating turnover and flux will be applied to each metabolite NIMS Analysis.

Frozen tissues will be sectioned and imaged as described in Aim 1. Alignment of NIMS data from serial sections of the punch will be used to create a 3D lipid flux model (x,y,z, Fractional Synthesis) of the punch in the same manner as we have shown previously for a 3D metabolite image of a tumor[37] and as we propose to perform with the neoplastic breast tissue.

Example 4: Flux Microscopy in Human Normal and Neoplastic Breast Tissue

The heavy water labeling approach has proven to be highly informative for characterizing phenotype in other neoplastic or hyperproliferative conditions, including chronic lymphocytic leukemia [45], psoriasis [46] and HIV-1 infection[47]. In a previous collaboration with Dr. Shelley Hwang MD (UCSF) proliferation of normal and tumor breast epithelial cells (BEC) were measured from breast tissue biopsies in women undergoing mastectomy.

A total of 15 patients will be enrolled for this study: 5 prior to surgery for benign disease and 10 untreated triple-negative breast cancer patients undergoing definitive surgery.

$^2H_2O$ Administration:

$^2H_2O$ will be administered for two weeks prior to surgery under Dr. Hwang's supervision. During $^2H_2O$ administration, weekly saliva samples will be obtained from all subjects at home via a Salivette kit (Sarstedt, Newton, N.C.) to monitor compliance.

Tissue Acquisition:

In cases with tumor, tissue from each quadrant of the breast will be collected in addition to the tumor-bearing region; for prophylactic mastectomies as well as reduction mammoplasties, we will attempt to collect tissue from each quadrant of breast as well as the nipple-areolar complex. 5×5×10 mm tissue samples will be collected and snap frozen. Samples of either normal stroma or invasive cancer and surrounding stroma measuring approximately 5×3×10 mm will be acquired. For samples containing tumor, targeted goal of tissue acquisition will be that up to one third of the specimen be comprised of normal stroma. In cases where a contralateral mastectomy is performed, paired tissues from the second breast corresponding to the same breast quadrant as the tumor) will be collected. Following standard pathological analysis, tissues will be snap frozen.

Histology and Immunohistochemistry:

Staining and sectioning will be performed in consultation with a pathologist. H&E sections will be evaluated in consolation with Dr. Stoppler in areas where tumor concentration exceeded 50% based upon surface area will be marked. The corresponding areas of the unstained sections will be microdissected and scraped into eppendorf tubes and shipped for distribution. We will use purified genomic DNA to measure proliferation rates of 1-3% per week for normal tissues, with progressive increases in proliferation rates in graded regions. Expression profililng will be performed in consolation with Dr. Stoppler and will include a standard panel of ER, PR, Her2, CK5/6, EGFR, Ki67, CSF1, CSF1R, as well as CSF1-response proteins (FCGR3a, FCGR2a. CTSL1, CD163) will be evaluated based on standard established IHC protocols. Conditions for antigen retrieval, proteolytic processing (if necessary), antibody titer, and positive/negative controls have been developed by the UCSF collaborators of Dr. Hellerstein and include over 100 antigens. Positively and negatively staining cell lines will be used as controls for all assays as needed.

NIMS Flux Analysis.

Frozen tissues will be sectioned and imaged as described in Aims 1&2 with care to image representative sections spanning the tumor and adjacent tissues.

Planned Analysis:

Our statistical approach will be exploratory in nature. Kinetic images will be characterized for turnover of a variety of lipids and for inhomogeneity (hot spots and cold spots). These qualitative features will be scored and compared to immunohistochemical results, using regression analysis. The intent is to validate the technology and generate hypotheses, not to identify definitive signatures at this time.

Clinical Interpretation of Results.

Lipid flux images will be compared with the standard pathological analysis from stained tissue sections and results from triple-negative xenograft and mouse models in order to link flux phenotypes to existing markers and response groups. Imaging of the tumors and surrounding tissues will be used to compare fluxes between benign vs. other subtypes of tissue and within the tumor vs. at the stromal interface to identify flux markers of cancer subtypes and the stratification of patients into different therapeutic-response classes based on flux patterns.

Example 5: In Situ Kinetic Histochemistry

This Example demonstrates the use of kMSI, a technique for imaging metabolic turnover based on the in vivo incorporation of stable isotope-labeled precursors into intact, non-fragmented molecules. The approach couples soft desorption/ionization mass spectrometry imaging with in vivo metabolic labeling with deuterium to generate kinetic images of biological processes. In this Example, kMSI was applied to a tumor, a tissue in which high growth rates and a diversity of metabolically transformed cells characterize the disease state. By isotopically labeling mice with deuterium and imaging excised tumors with nanostructure-initiator mass spectrometry (NIMS), kinetic images of lipid flux were generated as a first step towards spatially resolving synthesis rates of intact molecules that distinctively characterize metabolically heterogeneous tumor cell subpopulations.

Materials and Methods

Animal Care, Deuterium Administration and Tissue Collection.

Solid mammary tumors were obtained by transplanting Trp53-null mammary epithelium fragments (Balb/c background) into the cleared fat pad of F1 backcross female mice generated by the female interspecific F1 hybrid mice between BALB/c and SPRET/EiJ crossing with BALB/c male mice. $^2H_2O$ was administered by injecting a 30 mL/kg intraperitoneal bolus dose of sterile 99.9% $^2H_2O$+0.1% NaCl [58], followed by free access to drinking water (8% $^2H_2O$) and standard mouse chow. Animals were euthanized 5 days after $^2H_2O$ administration, then mammary tumor and serum were harvested, immediately flash-frozen on dry ice and stored at −80° C. As an unlabeled control, tumor and serum were also collected from a mouse never given $^2H_2O$. Animal treatment and care was performed in accordance with animal protocols approved by the Animal Welfare and Research Committee at Lawrence Berkeley National Laboratory (AUP 9111 & 27010).

NIMS Imaging.

For each tumor, one half was embedded in OCT medium and sectioned at −18° C. using a Leica 1950S cryostat and the other half was used for lipid extraction. Tumor cross-sections 5 μm thick were thaw-mounted onto a NIMS chip in preparation for MSI. Image acquisition was performed using a 5800 TOF/TOF (AbSciex, Foster City, Calif.) in positive reflector MS mode, with an Nd-YAG laser (200 Hz, 4650 laser intensity) acquiring spectra over a range of 500-1500 Da (900 Da focus mass) and accumulating 18 shots/spot. The 4800 Imaging Tool software was used to raster across the sample and record spectra in 50 μm×50 μm step-sizes. Data viewing and image reconstruction was performed using custom software developed in-house using the Matlab (Mathworks, Natick, Mass.) programming language.

Metabolite Extraction.

Frozen tumor samples (~4 mm×4 mm) were dried in a FreeZone 2.5 lyophilizer (Labconco, Kansas City, Mo.) (20-50 mg dry weight), homogenized using a Mini-Bead-beater (BioSpec Products, Bartlesville, Okla.) for 5 seconds, then further homogenized in 350 μL MeOH:IPA:$H_2O$ (3:3:2 v/v) extraction solvent for 4 seconds (2×). Samples were centrifuged at 15,000 rpm for 2 minutes, and the supernatant collected, filtered, and stored at −80° C.

NIMS of Tumor Extracts.

Sample extracts dissolved in MeOH:IPA:$H_2O$ (3:3:2 v/v) were spotted directly onto a NIMS chip in 0.5 μL drops, air-dried 30 seconds, then excess sample wicked off. Mass spectra were obtained using a 5800 TOF/TOF (AbSciex, Foster City, Calif.) in positive reflector MS mode with an Nd-YAG laser (200 Hz, 2950 laser intensity). Spectra were acquired over a range of 250-1500 Da (900 Da focus mass) and accumulating 18-22 shots/spot.

Liquid Chromatography Electrospray Ionization-Mass Spectrometry (LC ESI-MS) and MS/MS of Tissue Extracts.

MS of tumor extracts was performed using LC-MS normal phase chromatography on a 2.1 mm×150 mm 1.7 μm Acquity UPLC BEH Amide HILIC column (Waters Corporation, Milford, Mass.) and MS and MS/MS data were collected using an Agilent ESI-QTOF. Chromatography was performed at a flow rate of 40 μL/min using a 2 or 4 μL sample injection volume. The column was equilibrated with 100% buffer B (90% acetonitrile w/ 5 mM ammonium acetate) for 5 minutes, diluting buffer B down to 45% with buffer A ($H_2O$ w/ 5 mM ammonium acetate) over 30 minutes, and finally isocratic elution in 45% buffer B for 10 minutes. For LC/MS/MS, fragmentation data was acquired using 10, 20 and 40V collision energies.

Histopathology Stains.

Staining was performed on 10-μm thick tumor serial sections taken within 300 μm of the NIMS-imaged section. Chemical stains included hematoxylin and eosin (H&E), which differentiated cell nuclei (blue) from cytoplasm and protein (red). An immunohistochemical HRP/DAB stain (brown) for the cell proliferation marker Ki67 was also performed using monoclonal [SP6] to Ki67 (abcam, Cambridge, Mass.; #ab16667). Digital images were acquired using a ScanScope XT (Aperio, Vista, Calif.). Stains were performed both in-house and by the UCSF Helen Diller Family Comprehensive Cancer Center, Immunohistochemistry Core Facility.

Deuterium Enrichment in Serum.

Serum samples were analyzed for the amount of deuterium in body water by cavity ringdown spectroscopy using a Liquid Water Isotope Analyzer with an automated injection system, version 2 upgrade (Los Gatos Research, Mountain View, Calif.). Deuterium-enriched serum was diluted 1:100 prior to injection while unenriched serum was analyzed without dilution. Each sample was injected 6 times and the average of the last three measurements used for data analysis. A standard curve was run before and after samples for calculation of deuterium enrichment. Intra-run precision was less than 2 delta per mil (parts per thousand) and inter-run precision was less than 3.5 delta per mil. This analysis was performed by Metabolic Solutions, Inc. (Nashua, N.H.).

NIMS Wafer Fabrication.

Preparation of a NIMS surface has been thoroughly described elsewhere [35, 37]. Briefly, silicon wafers (Silicon Quest International, Santa Clara, Calif.) (single-sided polished P/Boron, orientation <1 0 0>, resistivity 0.01-0.02 Ωcm, 525+/−25 μm thick) were electrochemically etched using 25% hydrofluoric acid in ethanol under a constant current of 2.4 A for 15 minutes, then coated with bis (heptadecafluoro-1,1,2,2-tetrahydrodecyl) tetramethyl-disiloxane (Gelest, Morrisville, Pa.) as initiator.

Mass Spectrometry Imaging Data Processing.

Raw spectra with m/z values in the range of 790-880 were imported from each image file (.img format, generated by the 4800 Imaging Tool). The representative peaks with high average intensity correlated with the theoretical mass of the identified tumor lipids are provided in Table 2 below. The monoisotopic mass of each identified compound is shown for both $[M+H]^+$ and $[M+K]^+$ adducts. The difference between the measured mass and theoretical monoisotopic mass (ppm) is shown for mass spectra from direct NIMS imaging (comparing $[M+H]^+$ adducts) of tumor tissue and LC/MS (comparing $[M+H]^+$ adducts) of tumor extract. Values <30 ppm are shaded, with values <5 ppm in bold. The last column shows detection of the characteristic phosphocholine fragment (m/z=184) using LC/MS/MS, which confirms identification of the precursor ion as a choline phospholipid (n/d=not detected, n/p=not performed). Values of N used in the model of isotopic enrichment are also shown.

TABLE 2

Identification of phosphocholine (PC) lipid compounds in tumor mass spectra

| | Monoisotopic mass | | | | Measured - Theoretical (ppm) | | |
|---|---|---|---|---|---|---|---|
| # | $[M + H]^+$ | $[M + K]^+$ | Chemical Formula | N | NIMS, tumor tissue | LC/MS, tumor extract | Detected PC fragment from LC/MS/MS |
| 1 | 752.5225 | 790.4783 | C42H74NO8P | 30 | 3.4 | 45.6 | n/p |
| 2 | 754.5381 | 792.4939 | C42H76NO8P | 33 | 4.6 | 22.8 | n/d |
| 3 | 756.5538 | 794.5096 | C42H78NO8P | 36 | 2.6 | 0.1 | 184 |

TABLE 2-continued

Identification of phosphocholine (PC) lipid compounds in tumor mass spectra

| | Monoisotopic mass | | | | Measured - Theoretical (ppm) | | Detected PC fragment from LC/MS/MS |
|---|---|---|---|---|---|---|---|
| # | $[M + H]^+$ | $[M + K]^+$ | Chemical Formula | N | NIMS, tumor tissue | LC/MS, tumor extract | |
| 4  | 758.5694 | 796.5252 | C42H80NO8P | 39 | 2.6   | 1.2  | 184 |
| 5  | 760.585  | 798.5408 | C42H82NO8P | 42 | 26.7  | 0.7  | 184 |
| 6  | 762.6007 | 800.5565 | C42H84NO8P | 45 | 71.8  | 6.9  | 184 |
| 7  | 764.5589 | 802.5147 | C44H78NO7P | 33 | 4.2   | 49.2 | 184 |
| 8  | 766.5745 | 804.5303 | C44H80NO7P | 36 | 5.3   | 0.8  | 184 |
| 9  | 768.5901 | 806.5459 | C44H82NO7P | 39 | 3.1   | 8.8  | 184 |
| 10 | 770.6058 | 808.5616 | C44H84NO7P | 42 | 16.8  | 7.1  | 184 |
| 11 | 772.6215 | 810.5773 | C44H86NO7P | 45 | 46.0  | 6.6  | 184 |
| 12 | 774.6371 | 812.5929 | C44H88NO7P | 48 | 53.3  | 46.5 | 184 |
| 13 | 776.5225 | 814.4783 | C44H74NO8P | 27 | 64.9  | 47.1 | n/d |
| 14 | 778.5381 | 816.4939 | C44H76NO8P | 30 | 7.3   | 48.3 | 184 |
| 15 | 780.5538 | 818.5096 | C44H78NO8P | 33 | 9.8   | 14.2 | 184 |
| 16 | 782.5694 | 820.5252 | C44H80NO8P | 36 | 5.0   | 0.1  | 184 |
| 17 | 784.5851 | 822.5409 | C44H82NO8P | 39 | 2.5   | 1.7  | 184 |
| 18 | 786.6007 | 824.5565 | C44H84NO8P | 42 | 24.0  | 0.1  | 184 |
| 19 | 788.6164 | 826.5722 | C44H86NO8P | 45 | 66.2  | 1.6  | 184 |
| 20 | 790.5745 | 828.5303 | C46H80NO7P | 33 | 1.3   | 55.5 | 184 |
| 21 | 792.5901 | 830.5459 | C46H82NO7P | 36 | 2.3   | 3.4  | 184 |
| 22 | 794.6058 | 832.5616 | C46H84NO7P | 39 | 12.5  | 1.3  | 184 |
| 23 | 796.6215 | 834.5773 | C46H86NO7P | 42 | 42.8  | 7.7  | 184 |
| 24 | 798.6371 | 836.5929 | C46H88NO7P | 45 | 51.6  | 17.2 | 184 |
| 25 | 800.6528 | 838.6086 | C46H90NO7P | 48 | 75.9  | 54.3 | n/d |
| 26 | 802.5381 | 840.4939 | C46H76NO8P | 27 | 2.5   | n/d  | n/d |
| 27 | 804.5538 | 842.5096 | C46H78NO8P | 30 | 2.1   | 7.5  | 184 |
| 28 | 806.5694 | 844.5252 | C46H80NO8P | 33 | 4.6   | 0.5  | 184 |
| 29 | 808.5851 | 846.5409 | C46H82NO8P | 36 | 8.4   | 2.3  | 184 |
| 30 | 810.6007 | 848.5565 | C46H84NO8P | 39 | 18.5  | 0.4  | 184 |
| 31 | 812.6164 | 850.5722 | C46H86NO8P | 42 | 44.3  | 2.6  | 184 |
| 32 | 814.632  | 852.5878 | C46H88NO8P | 45 | 67.0  | 4.9  | 184 |
| 33 | 816.5901 | 854.5459 | C48H82NO7P | 33 | 1.3   | 0.5  | 184 |
| 34 | 818.6058 | 856.5616 | C48H84NO7P | 36 | 0.4   | 0.2  | 184 |
| 35 | 820.5851 | 858.5409 | C48H86NO7P | 39 | 27.5  | 38.9 | 184 |
| 36 | 822.6371 | 860.5929 | C48H88NO7P | 42 | 63.0  | 3.2  | 184 |
| 37 | 824.6528 | 862.6086 | C48H90NO7P | 45 | 108.3 | 10.1 | n/d |
| 38 | 826.5381 | 864.4939 | C48H76NO8P | 24 | 0.1   | n/d  | n/d |
| 39 | 828.5538 | 866.5096 | C48H78NO8P | 27 | 3.8   | n/d  | n/d |
| 40 | 830.5694 | 868.5252 | C48H80NO8P | 30 | 4.7   | 5.3  | n/d |
| 41 | 832.5851 | 870.5409 | C48H82NO8P | 33 | 3.1   | 1.3  | n/p |
| 42 | 834.6007 | 872.5565 | C48H84NO8P | 36 | 1.4   | 2.0  | n/p |
| 43 | 836.6164 | 874.5722 | C48H86NO8P | 39 | 9.7   | 5.0  | n/p |
| 44 | 838.632  | 876.5878 | C48H88NO8P | 42 | 54.1  | 5.8  | n/p |
| 45 | 840.6476 | 878.6034 | C48H90NO8P | 45 | 77.7  | 12.3 | n/p |

* n/d = no data

The exact masses of the identified lipid species were then used to calibrate m/z values comprising all spectra (FIG. 12). Using the calibrated spectra, peak heights in each pixel within +/−0.05 Da of either the theoretical monoisotopic peak or corresponding isotopologue peak were selected to generate images of 90 intensity values corresponding to the 45 phospholipids. For each intensity value, the measured background value (4 counts) was subtracted in each pixel. All further analyses, including K-means clustering and calculation of isotopic enrichment, were performed on these calibrated spectra.

K-Means Clustering.

Pixels comprising the mass spectrometry image were grouped into 9 regions by K-means analysis using a correlation distance function in Matlab 2011b [85]. This identified and grouped pixels with similar spectral patterns based on having similar relative intensities for the detected ions. This process was repeated 10 times and the iteration with the smallest error was used for analysis.

Model of Isotopic Enrichment.

Spectrum of each pixel were deconvoluted to separate individual lipid species into two groups—unlabeled and $^2$H-labeled—reflecting pre-existing and newly synthesized lipids, respectively. An unlabeled lipid was modeled as having an isotopic pattern specified by chemical formula and naturally-occurring distribution of heavy isotopes (FIG. 13—F1); the $^2$H-labeled lipid was modeled as having an isotopic pattern modulated by an increased amount of heavy hydrogen isotopes ($^2$H replacing H) due to metabolic incorporation from $^2$H-enriched water (FIG. 13—F2), with the modulation determined by (i) the amount of deuterium measured in enriched body water, atom % $^2$H (D), and (ii) N, the maximum number of deuterium atoms capable of being incorporated into newly synthesized lipids originating from water [65]. The final measured spectrum is a composite of both $^2$H-labeled and unlabeled isotopic patterns from the detected lipids (FIG. 13—Measured).

A SPIF approach, as exemplified in FIG. 24, was used to determine molecular flux rates. Model isotopic patterns were generated using the fast Fourier transform-based method [78, 79] in which isotopic abundances for any given elemental isotopic composition are user-specified. A fitting algorithm, implemented in Matlab 2011b, then finds a coefficient, $x_i$, for each term, $F1_i$ and $F2_i$, in the model (i.e.: 45 unlabeled and 45 $^2$H-labeled patterns) that minimizes the difference between the model and measured spectra using non-negative least squares fitting: Minimize x in $\|F \cdot x - M\|^2$, where x≥0, F is the matrix of spectrum for the model patterns and M is a vector of the measured spectra at a given position[80]. For each pixel spectrum, this model can be used to calculate the relative fraction of newly synthesized species.

Figure 9:
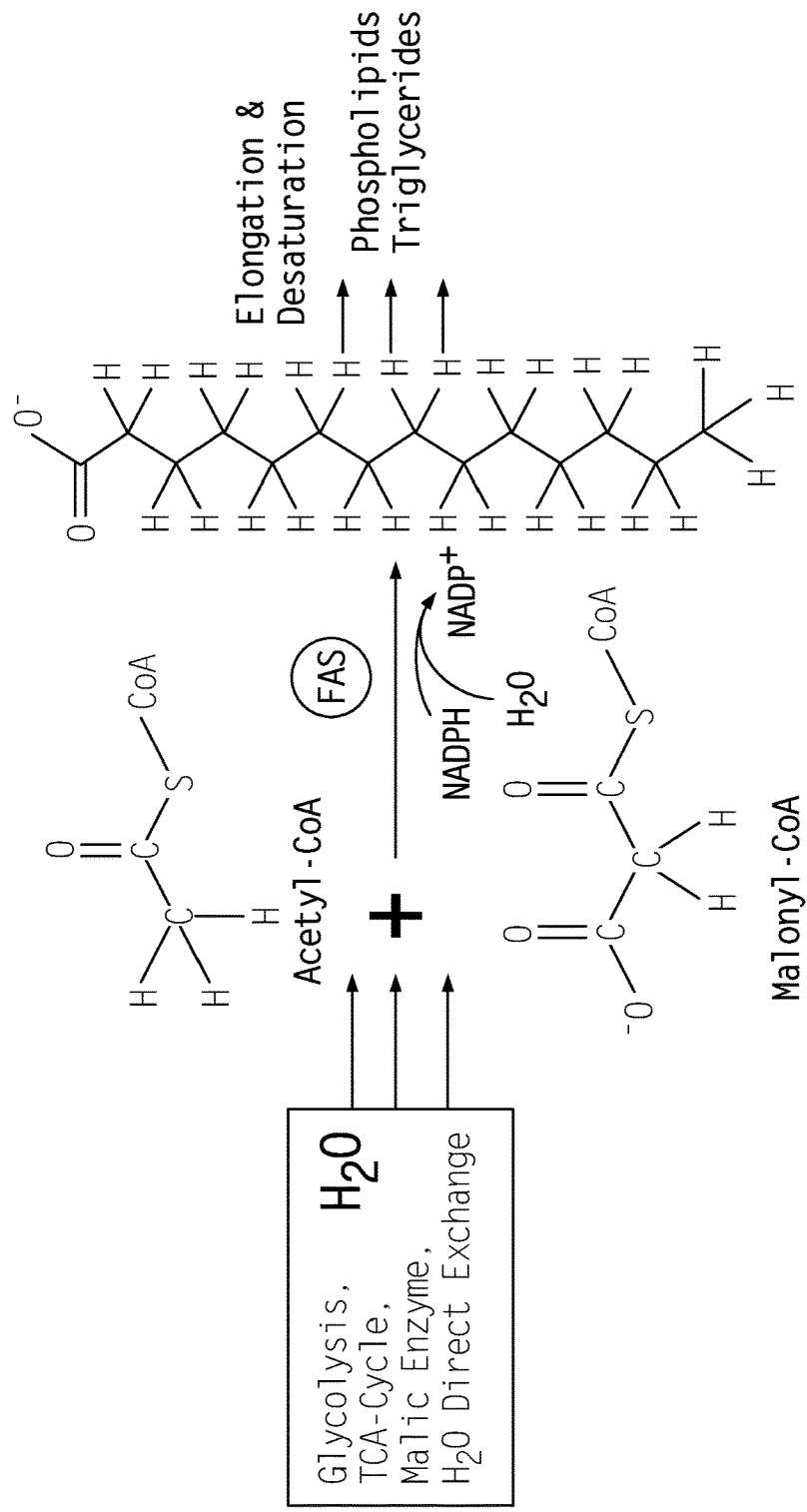
FIG. 9 depicts an exemplary reaction scheme for deuterium incorporation into phospholipids occurs during de novo fatty acid synthesis, a pathway utilizing substrates that have become metabolically deuterium-enriched themselves, including acetyl CoA, NADPH and water. Hydrogen atoms highlighted in red indicate the location on a newly synthesized fatty acid where deuterium may replace hydrogen, as well as the locations on metabolic precursor molecules.

As summarized in FIG. 9, deuterium incorporation into choline phospholipids occurs during synthesis of fatty acid chains by fatty acid synthase (FAS), with elongation and desaturation reactions increasing or decreasing the value of N [64]. During de novo lipogenesis, hydrogen molecules are derived from metabolic precursors already enriched from $^2$H$_2$O through various metabolic pathways, and contribute $^2$H instead of an H onto the growing fatty acid chain in proportion to the $^2$H/H ratio in body water [81]. While theoretically the maximum number of $^2$H's on a C-16 saturated fatty acid chain (palmitate) is N=31, experimental values measured in vivo are typically lower depending on tissue type and other biological considerations [34]. Based upon these previously reported values and experimental results, our model used D=4.5 atom % and N=21 for palmitate synthesis, with N+/−3d (d is the number of incremental 2-C units above or below C-16) to account for elongation or unsaturation[65]. Hydrogen atoms bound to heteroatoms are labile and therefore exchange with H in natural abundance in biochemical processing of a sample and not considered in the calculation of N.

Validation of Values for N.

Figure 14A:
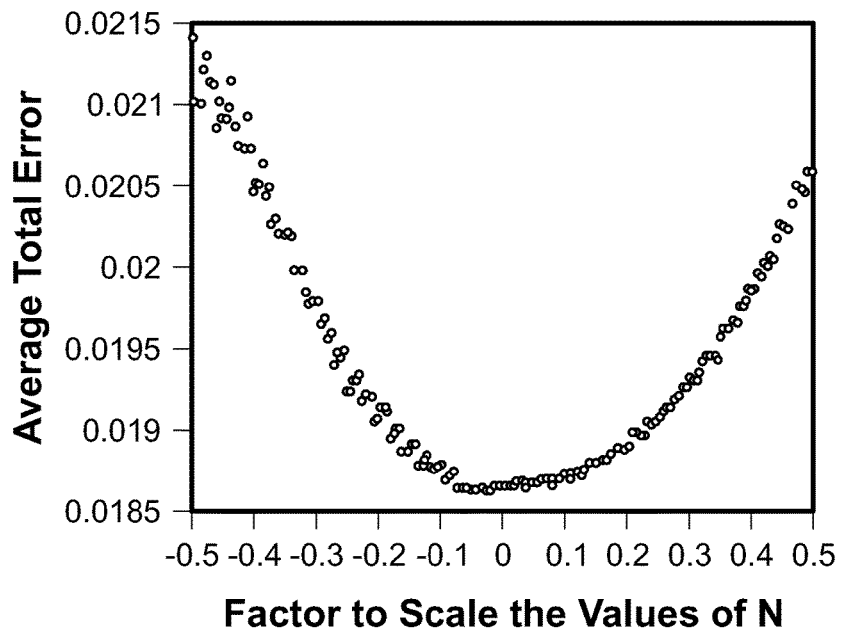
FIGS. 14A and 14B are graphs depicting the calculation of error using alternate values of N, the maximum number of hydrogen sites originating from water. In panel A, alternative values of N are calculated by scaling the original values by a factor (+/−50%). Modifying N by approximately +/−10% has little effect on the overall quality of the fit. In panel B, new values of N are calculated by directly adding or subtracting +/−15 hydrogens to each value of N in the model. Modifying N by approximately +/−5 has little effect on the overall quality of the fit.
Figure 14B:
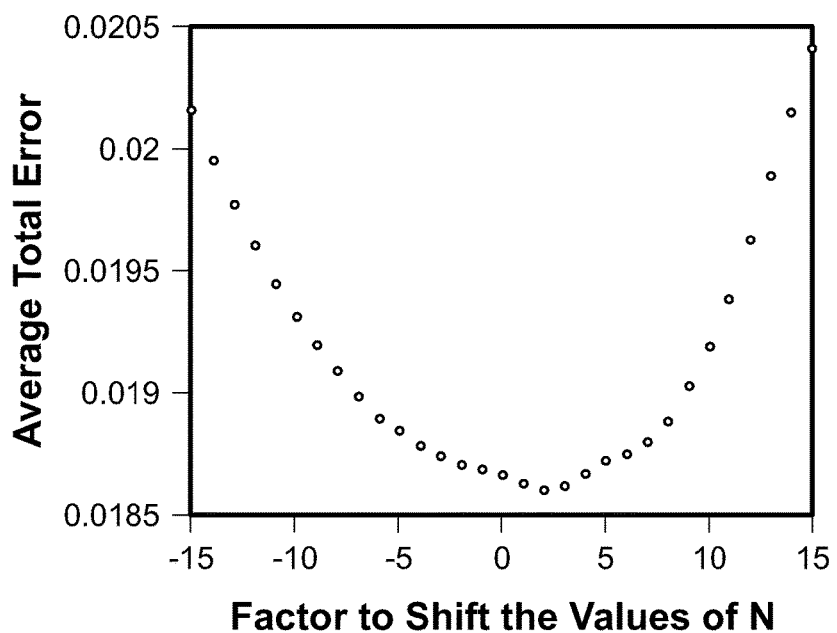

To evaluate selected values of N for each lipid, the isotopic enrichment model was also implemented using alternate values of N. Quality of fit over a range of values was tested by shifting or scaling the values of N (FIG. 14) by +/−50% or +/−15, respectively. Spectra with pixels having total intensity in the top 5$^{th}$ percentile were modeled by non-negative least squares fitting of the isotopic enrichment model. Plots in FIG. 14 show the average error minima is within only 5% or 2 hydrogen atoms from our selected values for N.

Results

In Vivo Biosynthetic Incorporation of Deuterium into Tissue:

The kMSI workflow for generating and imaging deuterium labeled tissues is summarized in FIG. 8. Briefly, administration of deuterated water ($^2$H$_2$O) to a tumor-bearing mouse provided known pathways for the biosynthetic incorporation of deuterium ($^2$H) into tissue lipids (FIG. 8A). Via active metabolic pathways, newly synthesized lipids became isotopically labeled with deuterium, whereas pre-existing lipids remained unlabeled (FIG. 9). By direct NIMS imaging of a deuterium-enriched tissue section, a unique mass spectrum was generated for each position for a variety of lipids (FIG. 8B) [9, 23]. Since each spectrum is a combination of isotopologues from unlabeled and $^2$H-labeled molecules at a given $^2$H$_2$O enrichment, spectra could then be deconvoluted to identify and quantify specific unlabeled and newly synthesized lipids at each location throughout the tissue (FIG. 8D). This enabled determination of the relative amount of newly synthesized lipid during the period of label exposure as a fraction of total lipid, which could then be correlated with static histopathology-based findings, including spatially-distinct tissue morphology and cellular subpopulations (FIG. 8C).

Figure 15A:
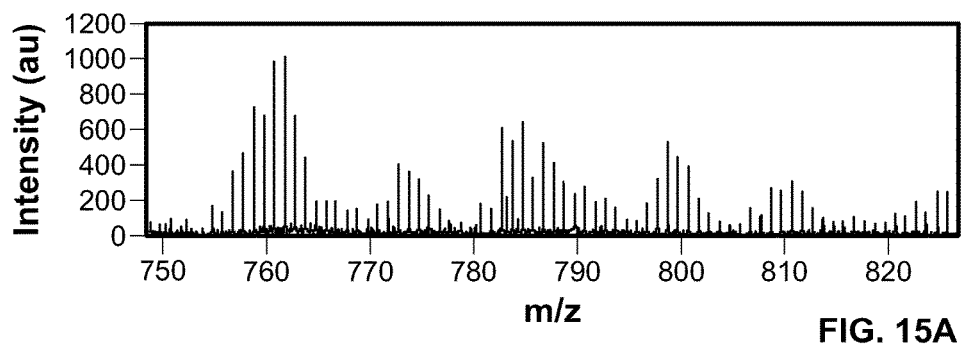
FIG. 15 depicts mass spectra generated from extracts spotted directly onto a NIMS chip from a (A) labeled and (B) unlabeled tumor, which show that, by visual inspection, the frequency in which the M1 isotopologue's intensity is either greater or near to the M0 isotopologue's (monoisotopic mass) intensity indicates deuterium enrichment in the labeled tumor and not in the unlabeled.
Figure 15B:
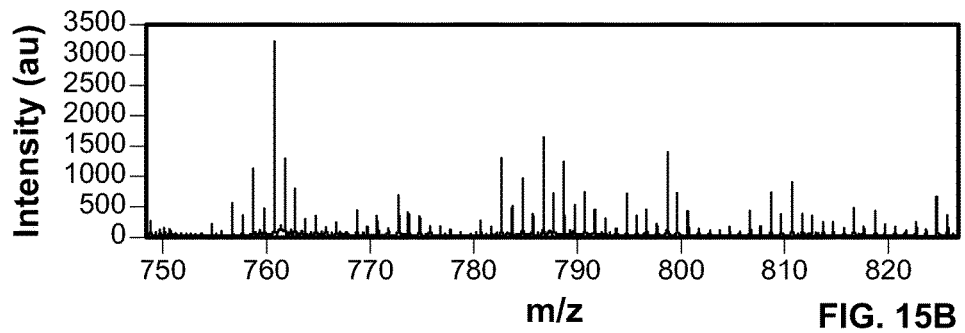

Isotopic incorporation of $^2$H into tissue was confirmed by comparing mass spectra generated from solvent-extracted tissue from a deuterium-treated versus an untreated mouse using liquid chromatography mass spectrometry (LC/MS) and NIMS. Isotopic patterns in spectra from the control, unlabeled mouse were consistent with naturally occurring isotopes; in contrast, isotopic patterns from the deuterium-treated mouse were composed of both $^2$H-labeled and unlabeled metabolites (FIG. 15). This is apparent by visual observation of the frequency in which the M1 isotopologue's intensity is greater than the M0 isotopologue's (monoisotopic mass) intensity [57]. As is typical in mass spectrometry, spectral patterns convey information on molecular composition; however, when tissue is also isotopically labeled, metabolic synthesis rates were also embedded within spectral patterns [58].

Deuterium Enrichment of Lipids:

Mass spectra were analyzed to identify detected molecules in deuterium-enriched tumor tissue. NIMS and LC/MS analysis revealed abundant ions (as measured by ion intensity) detected between the mass range m/z 750-846. Based upon exact mass and LC/MS/MS fragmentation spectra, these molecules were identified as being composed primarily of the protonated [M+H]$^+$ adducts of choline phospholipids (see Table 2 above). Detection of phospholipids, using either NIMS or matrix-assisted laser desorption ionization (MALDI), has been well-established due to good ionization and desorption properties [23, 59-61], and since they are a major component of cell membranes, phospholipids occur in naturally high abundance in biological tissues [62]. In tumors specifically, the tissue analyzed here, choline lipids are highly upregulated and implicated in the pathology of tumor metabolism and malignancy [63].

Validation of Model of Isotopic Enrichment:

Based on choline phospholipids, we developed a model of isotopic enrichment to apply to spectral patterns to quantify both composition and new synthesis for each lipid. A full description of the model is provided in the Supplementary text but summarized briefly here. As shown in FIG. 9, deuterium is incorporated into choline phospholipids during synthesis of fatty acid chains, with deuterium-enriched water contributing $^2$H instead of an H onto the growing fatty acid chain and modulating the isotopologue distribution pattern detected by mass spectrometry [64]. While the maximum theoretical number (N) of $^2$H's originating from water and capable of replacing H on a 16-carbon saturated fatty acid chain (palmitate) is N=31, experimental values measured in vivo are typically lower depending on tissue type and other biological considerations [34]. Based upon previously reported values and experimental results, our model used N=21 for palmitate synthesis, with N+/−3d (where d is the number of incremental 2-carbon units above or below a 16-carbon chain length) to account for elongation or unsaturation of fatty acid chains of each phospholipid [65]. Also, using cavity ringdown spectroscopy, body water was measured at 4.5 atom % $^2$H (see Table 3 below) to allow calculation of a value for D, the fraction of exchangeable H's actually replaced by $^2$H during synthesis of a newly labeled molecule.

TABLE 3

Measurement of atom % D in body water

| Sample | Average Atom % D |
|---|---|
| Serum, deuterium-enriched mouse | 4.50 |
| Serum, control mouse | 0.0149 |

Figure 19:
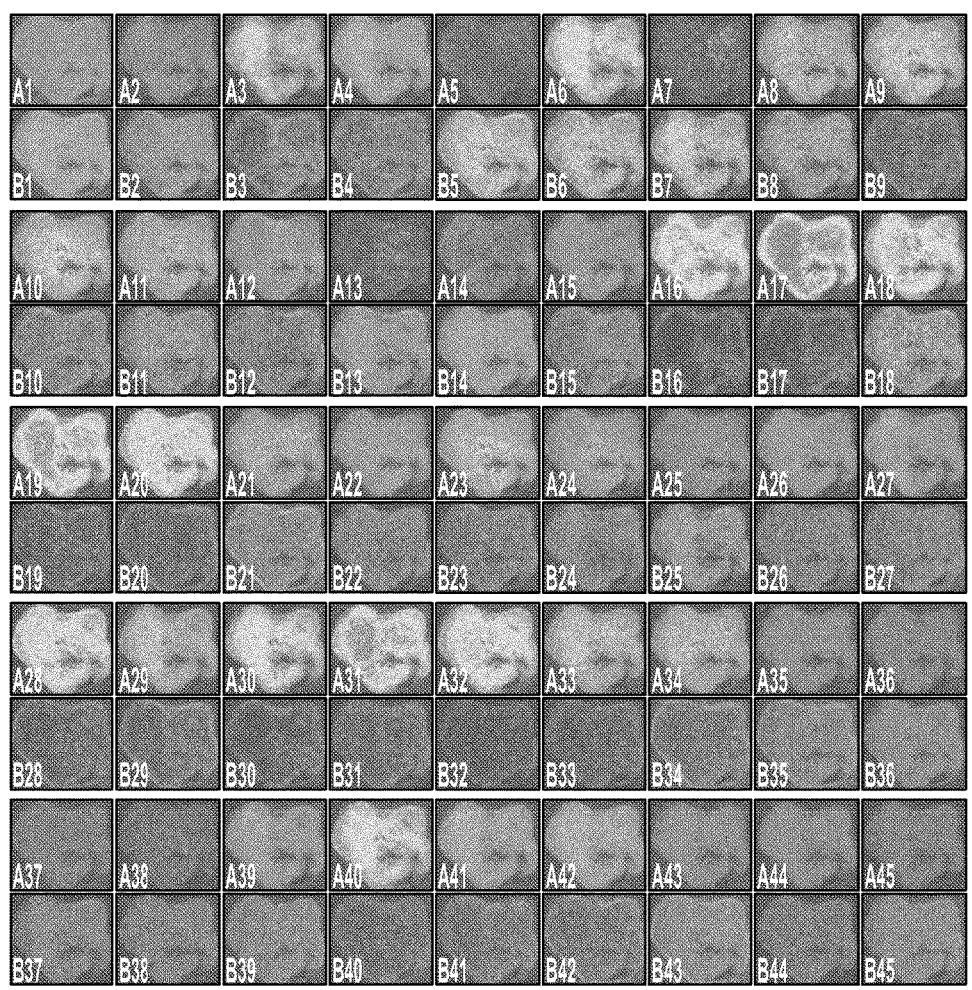
FIG. 19 depicts intensity images of the unlabeled, control tumor for the 45 phospholipids identified in Example 5, where each column represents a unique lipid. For each block, the top row is unlabeled (pre-existing) and bottom row is $^2$H-labeled (newly synthesized), and where image subscripts link to Table 2 in Example 5 corresponding to specific lipid species.
Figure 20:
FIG. 20 depicts intensity images of the deuterium-enriched tumor for the 45 phospholipids identified in this study, where each column represents a unique lipid. For each block, the top row is unlabeled (pre-existing) and bottom row is $^2$H-labeled (newly synthesized), where iImage subscripts link to Table 2 in Example 5 corresponding to specific lipid species.

These values for N (see Table 2 above) and D were used to deconvolute the spectra and separate individual lipid species into two groups—unlabeled and $^2$H-labeled—reflecting pre-existing and newly synthesized lipids, respectively. We validated our model and that selected parameters (see Table 3 above) were capable of discriminating between $^2$H-labeled versus unlabeled lipids. This resulted in the fraction of $^2$H-labeled lipids in the control tumor to be quantified as near zero (within noise), while each lipid in the deuterium-treated tumor was found to be enriched in $^2$H-labeled isotopologues (FIGS. 19 and 20).

Mass Spectrometry Imaging of Isotopically Enriched Tumor Lipids:

To explore whether alterations in spectral patterns could also be used to spatially discriminate biosynthetic rates among tumor subregions, this model was applied to spectra derived from mass spectrometry imaging of tumor sections. By performing NIMS imaging directly on a thin tumor section, an individual mass spectrum was generated for each location in 50 μm increments. Spectra revealed abundant ions (as measured by ion intensity) detected between the mass range m/z 788-884. As is typical in mass spectrometry imaging, the potassium adducts [M+K]$^+$ of choline phospholipids were detected from direct imaging of the tissue; these corresponded to the protonated species [M+H]$^+$ of choline phospholipids already identified in the tumor extracts [66]. Comparable to spectra from tumor extracts, imaging spectra from the control tumor displayed natural isotopic abundance, while spectra from the labeled tumor displayed composite spectra of $^2$H-labeled and unlabeled species.

Heterogeneous Distribution of Lipid Flux: Newly Synthesized Vs. Pre-Existing Lipids:

To visualize the spatial distribution of newly synthesized versus pre-existing lipids, our model of isotopic enrichment was used to generate intensity images ($^2$H-labeled and unlabeled) for each lipid species (FIGS. 19 and 20). Some of the most abundant lipids are shown for the deuterium-enriched tumor in FIG. 10. Interestingly, the spatial distribution of newly synthesized lipids did not correspond to that of pre-existing lipids. While some newly synthesized lipids localized in specific regions, others were distributed more heavily in the general periphery. This lipid-specific regional variation in flux demonstrates that active metabolic processes are region-specific and may correspond to cellular subpopulations or other characteristics of the tumor environment.

Figure 11A:
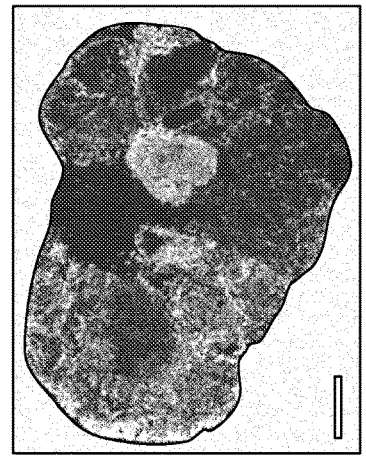
FIG. 11A depicts a spatial distribution of clustered pixels for each K-means region attributed to the tumor phospholipids shown as individual images (left) and a merged overlay (right) with colors corresponding to the following regions: I—red, II—green, III—cyan, IV—yellow, V—blue, VI—purple. Scale bar, 5 mm.
Figure 11A:
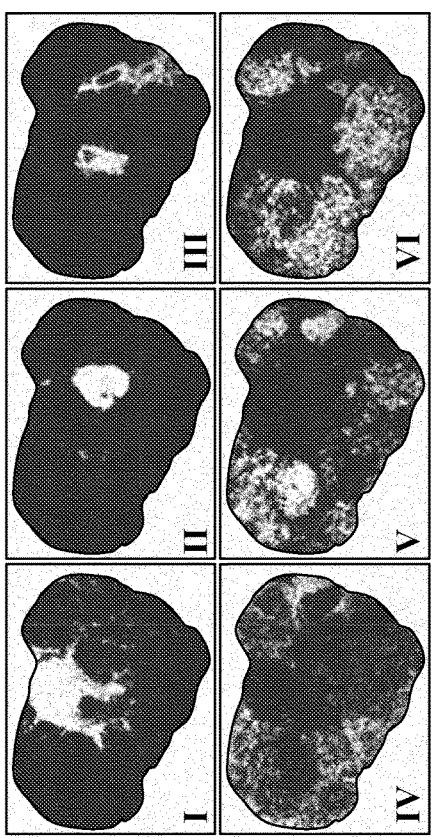
Figure 11B:
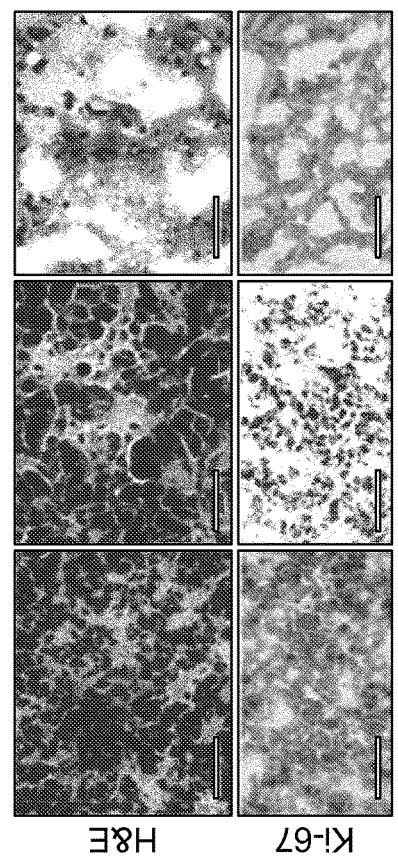
FIG. 11B depicts H&E and Ki-67 stains corresponding to K-means regions I to III, scale bars, 50 μm (H&E) and 100 μm (Ki-67).
Figure 11C:
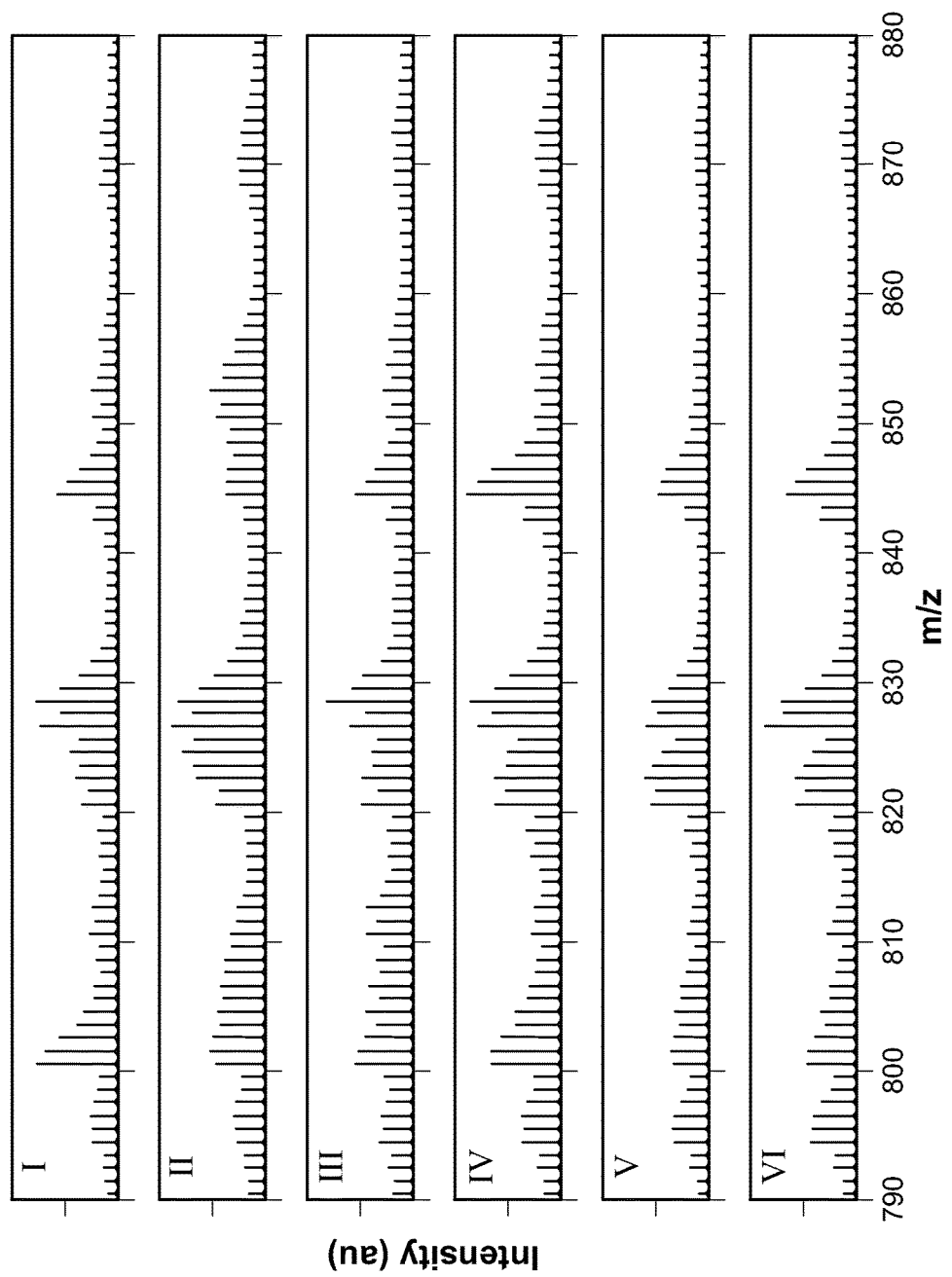
FIG. 11C depicts an average spectra corresponding to each K-means region identified in the $^2$H-labeled tumor.
Figure 16:
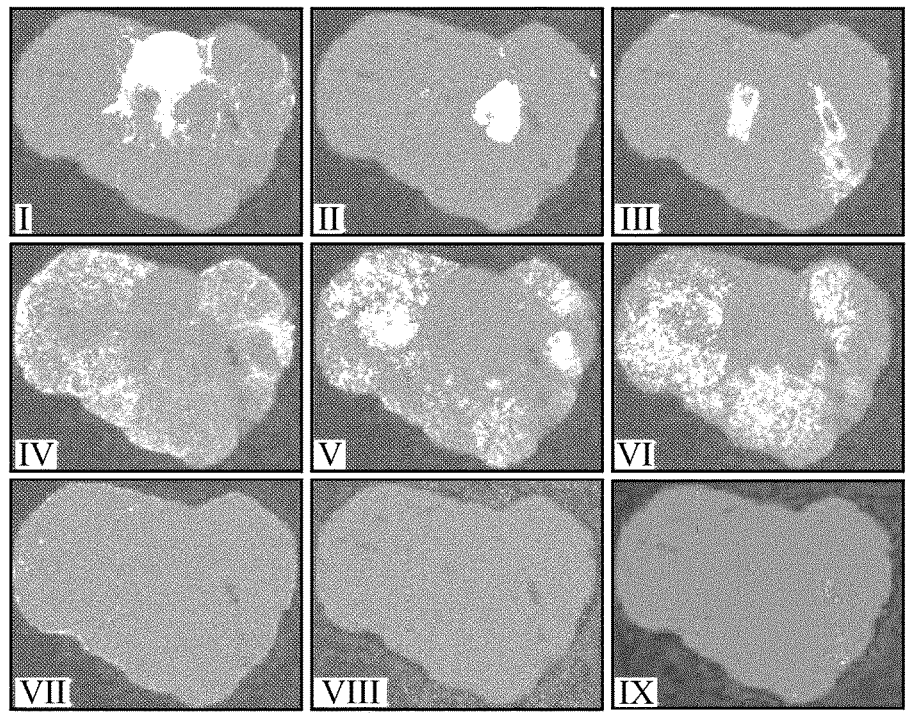
FIG. 16 depicts images of the nine regions identified in the deuterium-enriched tumor by applying K-means analysis, identifying 3 regions associated with background (Regions VII-IX) and 6 regions associated with the tumor (Regions I-VI).
Figure 17:
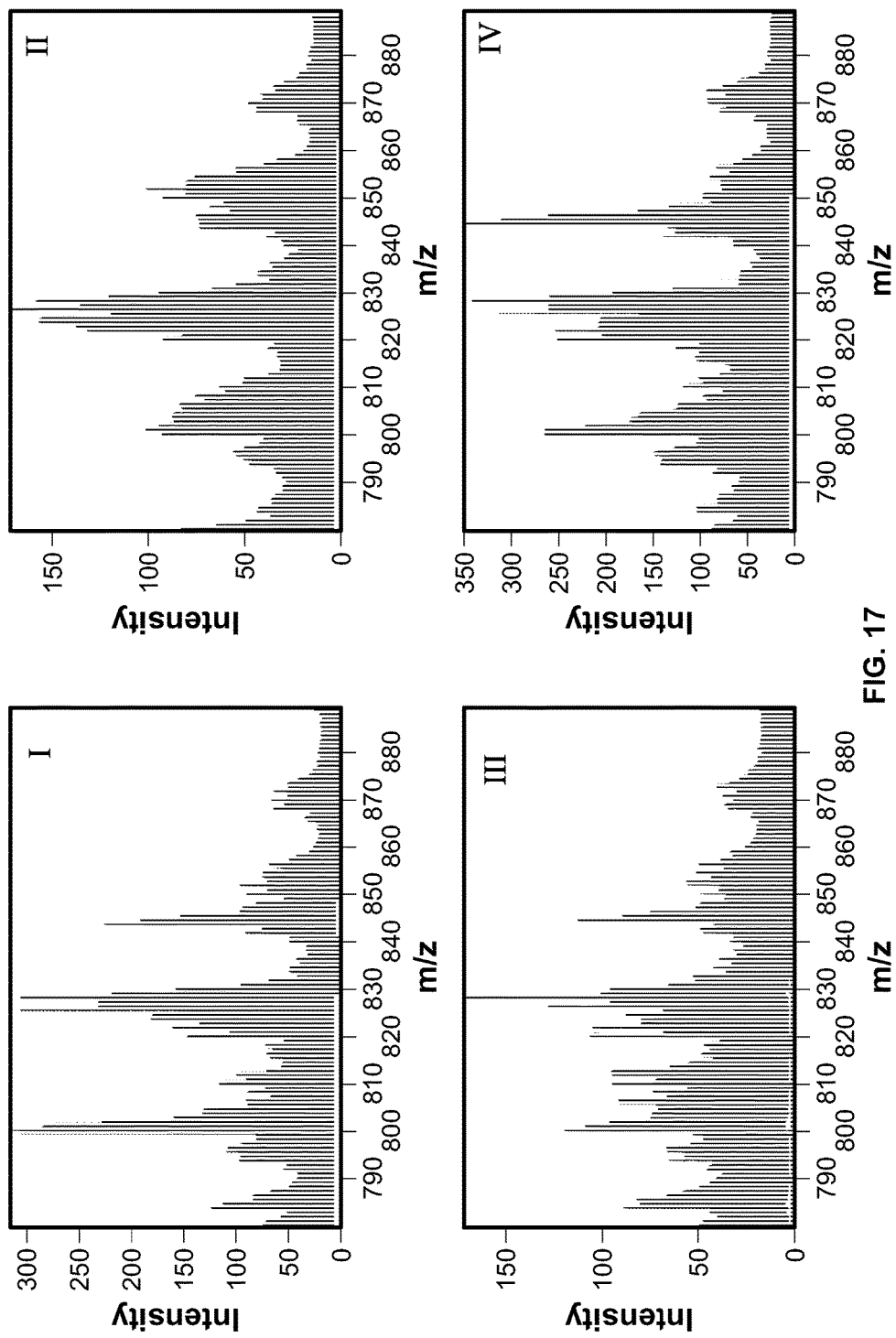
FIG. 17 depicts average spectra corresponding to the nine regions identified in the deuterium-enriched tumor by applying K-means analysis.
Figure 17:
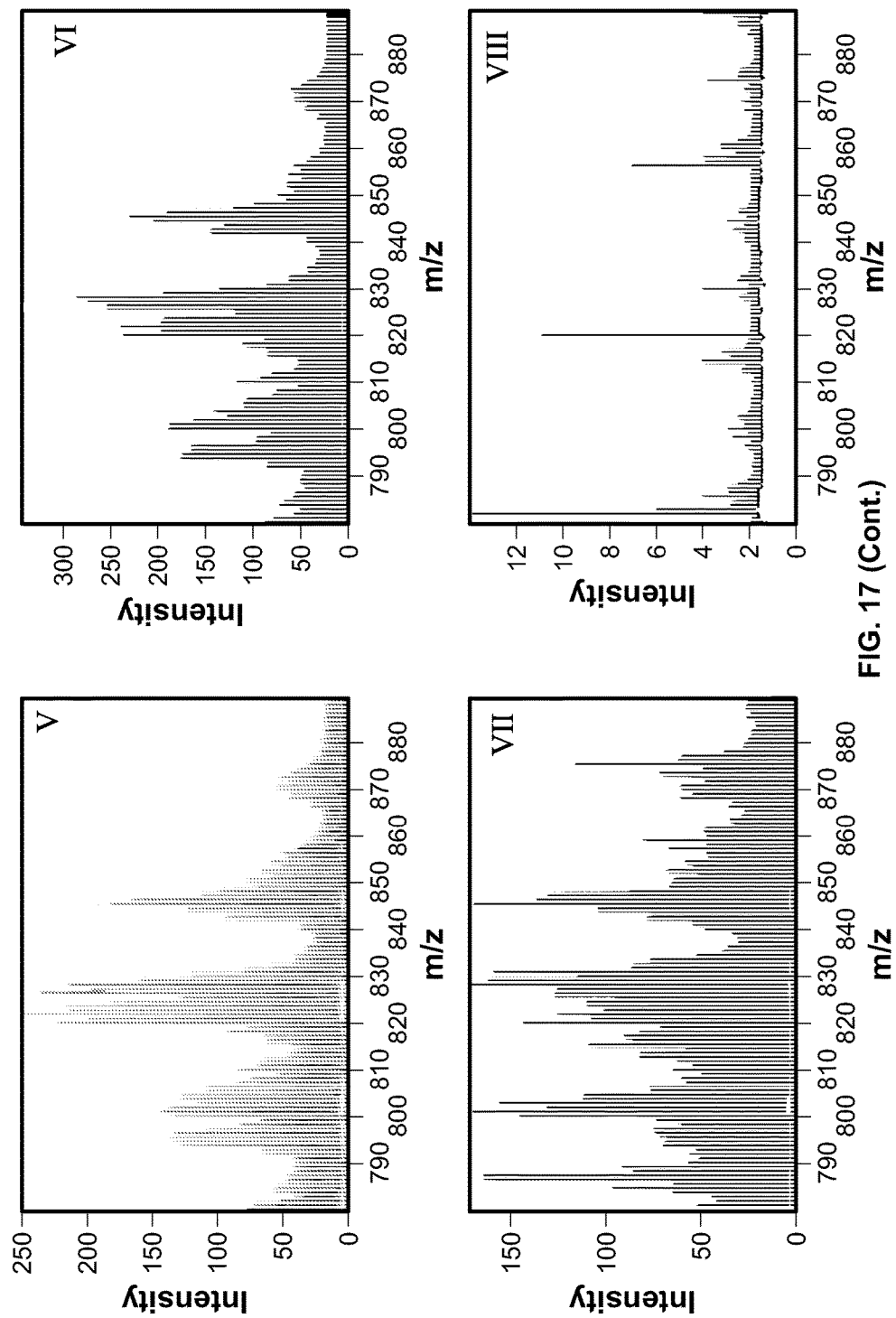
Figure 17:
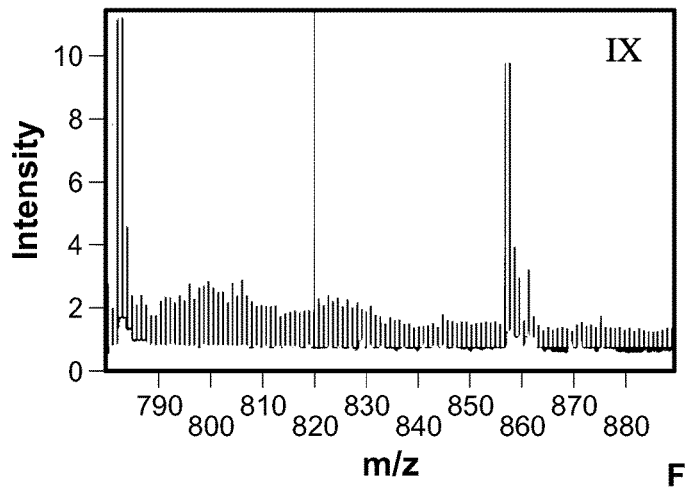

Identification of Tumor Sub-Regions Using kMSI Spectra:

To identify tumor subregions based upon both lipid composition and metabolic synthesis, K-means analysis was applied to each pixel of the tumor image. This analysis clustered pixels into 9 distinct patterns based upon spectral similarity [67]. Images and average spectra of pixels comprising each pattern tended to cluster spatially (FIGS. 11A and 11C; FIGS. 16 and 17). Based upon spectral patterns and spatial distribution, 3 regions were identified as artifact unrelated to tumor biology (IX—NIMS background ions; VII, VIII—embedding medium used in sectioning), while the remaining 6 were attributed to detection of endogenous tumor phospholipids. The overlay image in FIG. 11A shows the relative spatial distribution of each region. While Regions I-III localize in spatially-distinct areas, regions IV-VI overlap and appear more dispersed throughout the tumor periphery.

Figure 21:
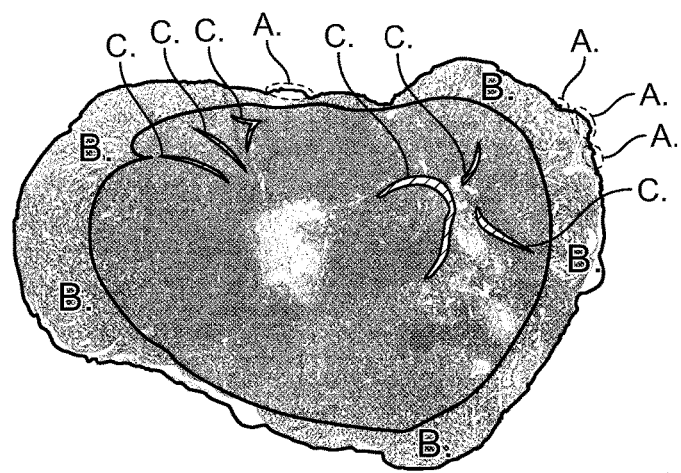
FIG. 21 depicts an H&E stain of a deuterium-enriched tumor with no normal appearing breast parenchyma, in which "A" (red) represents small peripheral areas of adherent skeletal muscle are noted, "B" (black) represents all of tissue has moderate frozen section artifact, more pronounced artifact peripherally, "C" (blue) represents all of the tissue has delicate intersecting fibrous tissue, and larger fibrous septa are as marked.
Figure 22:
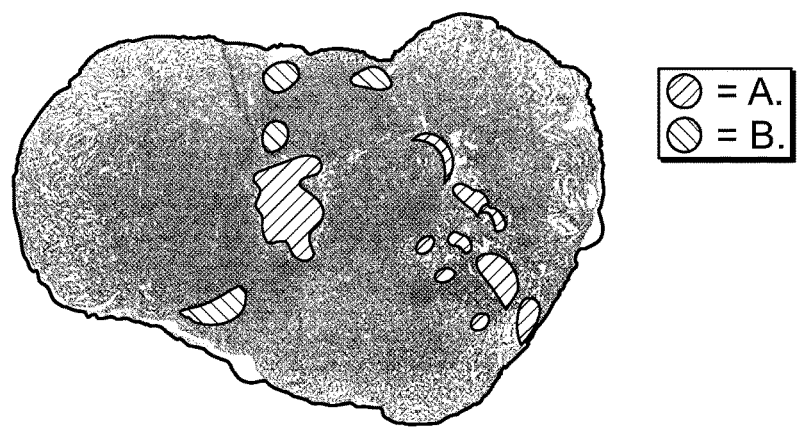
FIG. 22 depicts an H&E stain of a deuterium-enriched tumor with no normal appearing breast parenchyma, in which "A" (red) represents variable sized zones of tumor necrosis (with apoptotic bodies and cell ghosts), "B" (black) represents regions where architecture is variable with most areas showing very poorly-formed glandular structures along the delicate intersecting fibrous tissue, and areas with slightly better formed glandular structures are as marked.
Figure 23:
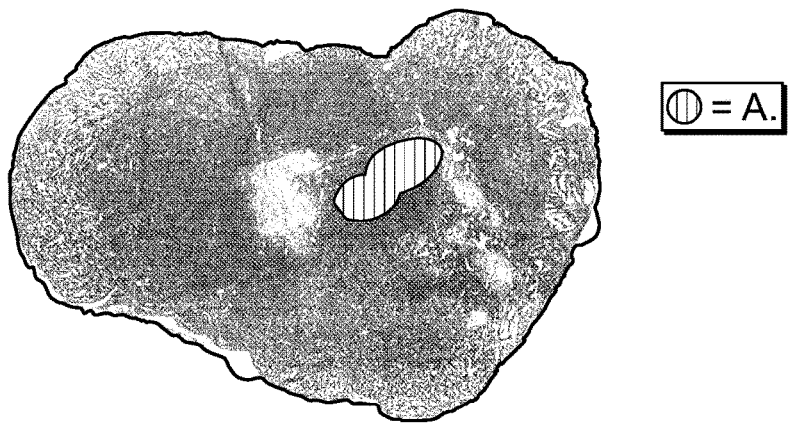
FIG. 23 depicts an H&E stain of a deuterium-enriched tumor with no normal appearing breast parenchyma, in which "A" (red) represents a region where most of the tumor is composed of intermediate to large sized cells with moderate pleomorphism. One area shows marked pleomorphism with "bizarre" nuclei and cells with multiple nuclei.

Correlation of Lipid Flux in Tumor Sub-Regions with Histopathology Stains:

To determine whether the K-means regions corresponded to physiological differences, a blinded histopathology examination was performed on an H&E serial section (FIGS. 21-23). In the H&E stain, two of the tumor lobules were distinctly characterized by abnormal tissue architecture and nuclear pleomorphism associated with malignancy (FIG. 11B, H&E I and II)—spatially, these corresponded to K-means regions I and II. Further, these two regions could be morphologically distinguished from one another based upon observed degree of cell differentiation into glands, pleomorphic versus monomorphic character and range of cell size, with Region II showing more high-grade histologic features as compared to Region I.

Figure 18A:
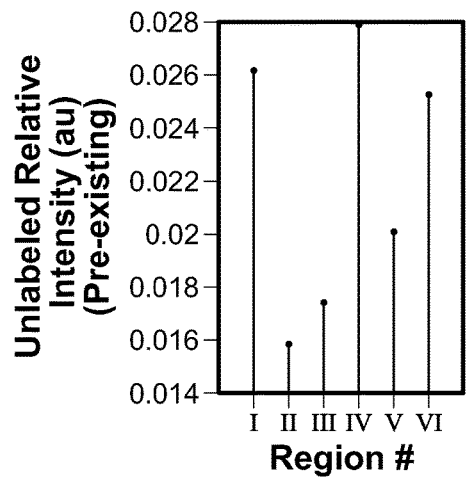
FIGS. 18A and 18B depict graphs to compare relative levels of new synthesis and turnover between K-means regions, the normalized, average intensity originating from unlabeled and $^2$H-labeled lipids is shown for Regions I-VI, respectively.
Figure 18B:
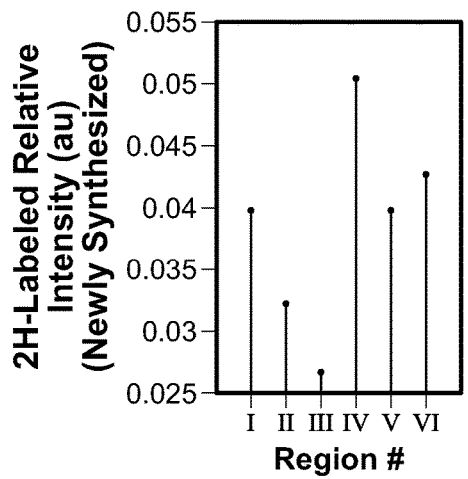
Figure 18C:
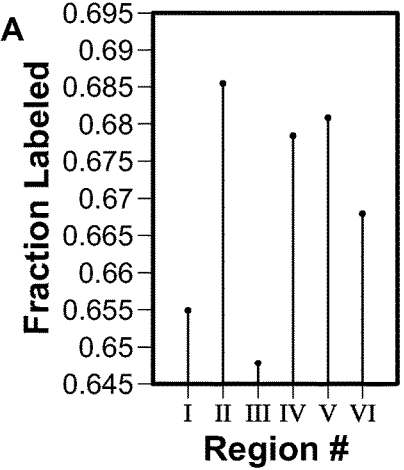
FIG. 18C depicts a graph that plots the fraction of total signal originating from newly synthesized (labeled) lipids for each region. Region II, characterized as having high grade features of malignancy according to H&E, has the lowest levels of pre-existing lipids (Panel A) and the highest fraction of newly synthesized lipids (Panel C). Region III, characterized as necrotic according to H&E, has the lowest levels of newly synthesized lipids overall (Panel B).

Another corresponding stain for Ki-67, a nuclear marker present in all stages of the cell cycle except G0, provided a measure of cell proliferation in these regions [68]. Analysis indicated high rates of cell proliferation in both these regions, with region II higher than that of I (FIG. 11B, Ki-67 I and II), and region II also having the highest fractional amount of newly synthesized lipids (FIG. 18c). Necrotic areas of the tumor were also identified in the H&E stain, which corresponded with region III, the region with lowest levels of new synthesis (FIG. 11B; FIGS. 18B and C). Although regions IV-VI were difficult to characterize in terms of tumorigenic properties in relation to the H&E stain, alterations in lipid composition were clearly reflected by the mass spectrometry imaging analysis. This suggests that Regions IV-VI may be composed of multiple cell subpopulations interspersed with each other, and this kinetic histology approach could provide a mechanism for distinguishing each one.

Discussion

Further insight was gained by examining synthesis of individual lipids (FIG. 10) with respect to each K-means region (FIG. 11A). Some of the most abundant phospholipids identified were those containing saturated and monounsaturated fatty acids (SFAs and MUFAs), including PC (34:0), PC (34:1) and PC (36:1). Synthesis of these fatty acids is typically upregulated in aggressive tumors, with SFAs being the initial product of de novo lipogenesis and conversion to MUFAs occurring by only a single desaturation reaction[69]. The balance of SFAs to MUFAs has been implicated as critical for tumor cell survival, such that when this balance is shifted the cancer cell cannot survive [70]. Synthesis of phospholipids containing SFAs and MUFAs occurred heterogeneously within the tumor. While highest levels of PC (34:0) were associated with K-means Region I, PC (34:1) and PC (36:1) were distributed more throughout the tumor periphery in Regions IV-VI. Further, K-means Region II, the most high grade area identified within the tumor, had only minimal amounts of many of these lipids, but was highly abundant in PC (36:3), with two lipid species PC (38:3) and PC (38:4) newly synthesized primarily in this region. These results suggest that region I and II, both high grade regions, may be composed of discrete cell subpopulations relying on alternate metabolic pathways for survival. Additionally, synthesis of phospholipids containing highly polyunsaturated fatty acids (PUFAs) were not generally localized in regions I and II, where the SFAs and MUFAs were found, implying that lipid desaturation was region specific. This may be due to differential expression of fatty acid synthase (FAS) and desaturase enzymes between cell populations or levels of incorporation of dietary fatty acids. Specifically, new synthesis of PC (38:6) and PC (38:7), containing 6 and 7 unsaturated bonds, respectively, were found throughout the tumor periphery in Regions IV-VI (FIG. 10). PUFAs change membrane fluidity and structure, a compositional change that modifies overall cell function and response [53]. Further, PUFAs have been shown to be particularly toxic to certain cancer cell lines given their susceptibility to lipid peroxidation and increasing cytotoxic oxidative stress within the tumor cell [71, 72], suggesting that the spatial distribution of PUFAs within the tumor may correspond to additional cell subpopulations with diverse metabolic characteristics and level of aggressiveness.

These results show that kMSI is capable of generating kinetic images that distinguish metabolically distinct tissue regions. In this case, differences in de novo lipogenesis and phospholipid composition were found to correspond to histopathologically-distinct regions in the tumor. These observations are consistent with recent studies showing intratumor heterogeneity between cell subpopulations in terms of genetics and metabolism, with different therapeutic approaches necessary owing to these differences [37, 73-77]. Since deuterium administration in the form of $^2H_2O$ is already commonly applied in the clinical setting [62], kMSI images of the dynamic metabolic processes within tissues can complement existing histopathology techniques and may find broad utility in understanding physiology, disease and development.

Figure 26A:
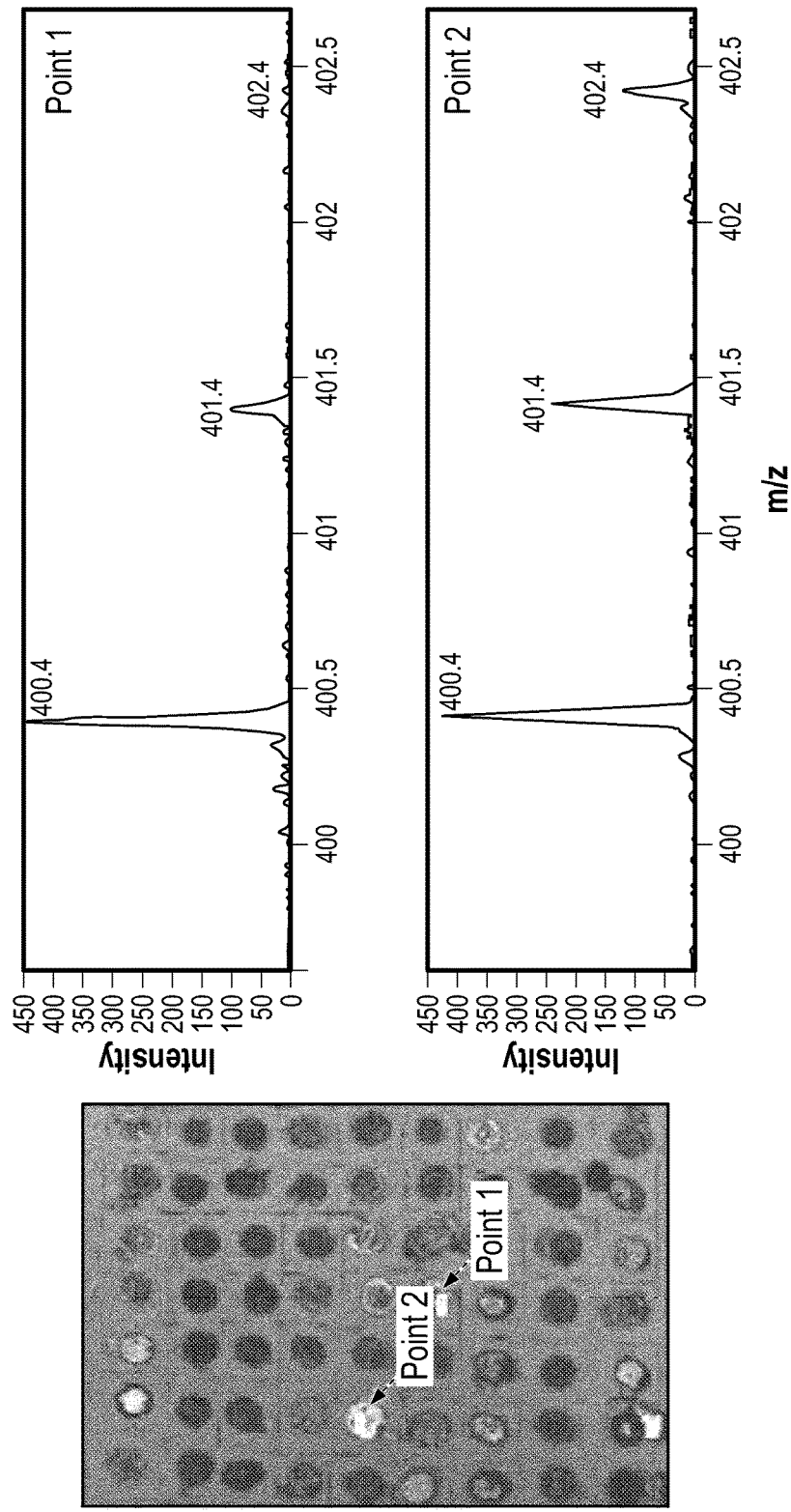
FIGS. 26A and 26B are two exemplary kinetic images of the enrichment of palmitoyl carnitine and phosphocholine lipids, respectively, obtained in accordance with the protocol described in Example 6. The images depict metabolites that were extracted using a solvent, which was then arrayed on a surface suitable for mass spectrometry imaging. The different spots in the image were from different tissues and different subjects. The red color in the image was proportional to the amount of the isotopologue at 400.4 Da. The green color was proportional to the isotopologue at 401.4. The relative color in each pixel represents one type of flux image and is based on the relative intensities of the two ions.
Figure 26B:
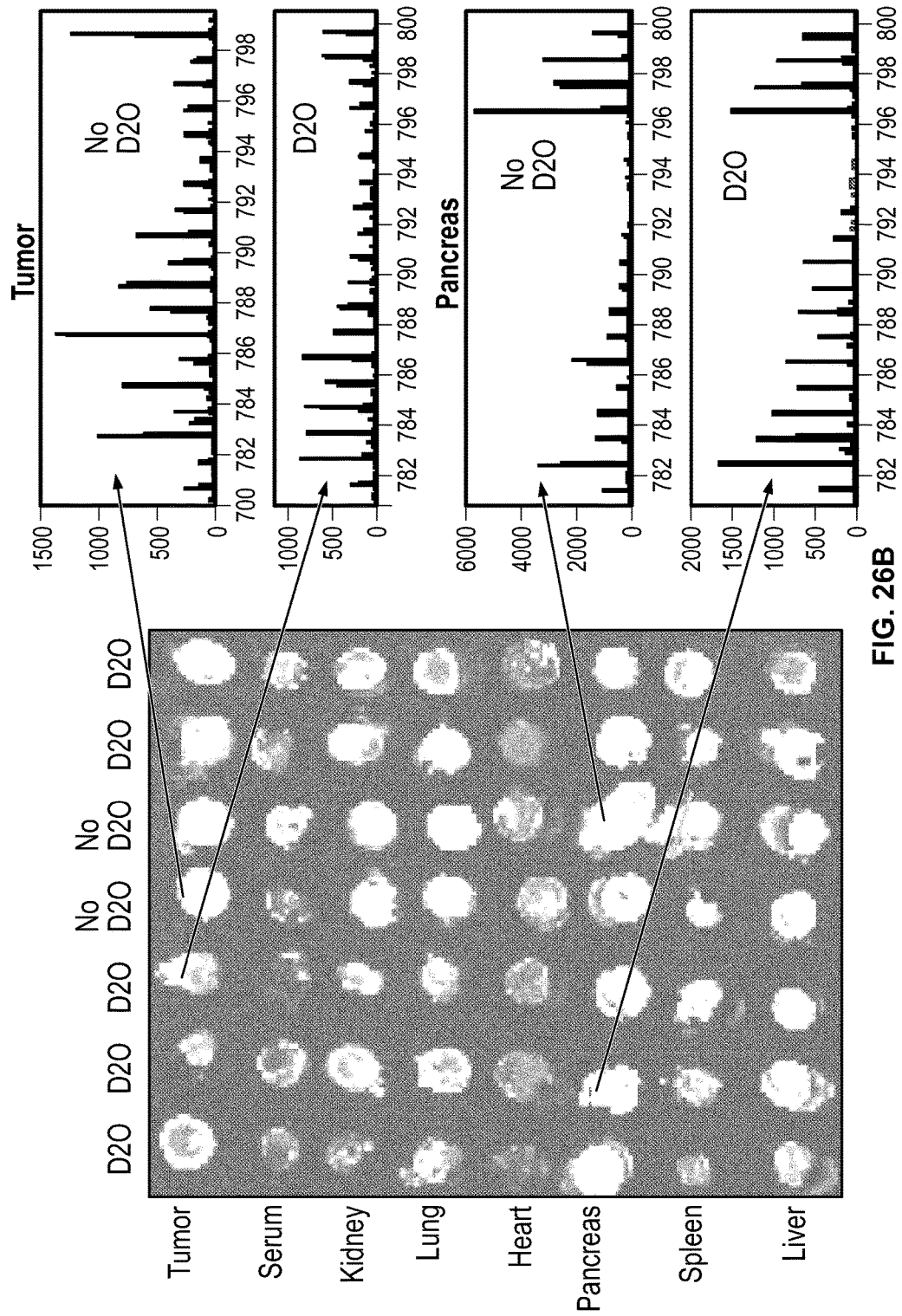

Example 6: Kinetic Images of Solvent-Extracted Tissues with NIMS or Other Mass Spectrometry Imaging Imaging of different tissue types, and from different mice, has shown that metabolic flux patterns differ between different tissues and health status of the individual. To determine the ability to image isotopomer abundance patterns and determine flux from multiple tissues from the same mouse, and compare these with the same tissues from different mice, dissected tissues from tumor-baring adult mice given 5% 2H2O for 5 days were extracted in 3:3:2 (MeOH:IPA:H2O) solvent, then spotted on a silicon NIMS chip and imaged with NIMS (FIG. 5). For each pixel, numerous metabolites could be observed (FIGS. 26A and 26B). With reference to FIG. 5, as can be seen in panels 5A-5D, the relative flux observed after 5 days of administration of $^2H_2O$ varies for each tissue type at each m/z value corresponding to a metabolite (this is visually obvious when looking at the M0 to M1 ratios between the different tissue). In the case that it is necessary to resolve sub-micron lipid flux, TOF-SIMS can be used to detect deuterium incorporation into hydrocarbon fragments.

OTHER REFERENCES

Bibliography and References Cited

1. Hsu, P. P. and D. M. Sabatini, *Cancer cell metabolism: Warburg and beyond*. Cell, 2008. 134(5): p. 703-707.
2. McCubrey, J. A., L. S. Steelman, W. H. Chappell, S. L. Abrams, E. W. Wong, F. Chang, B. Lehmann, D. M. Terrian, M. Milella, A. Tafuri, F. Stivala, M. Libra, J. Basecke, C. Evangelisti, A. M. Martelli, and R. A. Franklin, *Roles of the Raf/MEK/ERK pathway in cell growth, malignant transformation and drug resistance*. Biochim Biophys Acta, 2007. 1773(8): p. 1263-84.
3. Liu, H., D. C. Radisky, F. Wang, and M. J. Bissell, *Polarity and proliferation are controlled by distinct signaling pathways downstream of PI3-kinase in breast epithelial tumor cells*. J Cell Biol, 2004. 164(4): p. 603-12.
4. DeBerardinis, R. J., J. J. Lum, G. Hatzivassiliou, and C. B. Thompson, *The biology of cancer: metabolic reprogramming fuels cell growth and proliferation*. Cell Metab, 2008. 7(1): p. 11-20.
5. Cichon, M. A., A. C. Degnim, D. W. Visscher, and D. C. Radisky, *Microenvironmental Influences that Drive Progression from Benign Breast Disease to Invasive Breast Cancer*. J Mammary Gland Biol Neoplasia, 2010. 15(4): p. 389-397.
6. Deeb, K. K., A. M. Michalowska, C. Y. Yoon, S. M. Krummey, M. J. Hoenerhoff, C. Kavanaugh, M. C. Li, F. J. Demayo, I. Linnoila, C. X. Deng, E. Y. Lee, D. Medina, J. H. Shih, and J. E. Green, *Identification of an integrated SV40 T/t-antigen cancer signature in aggressive human breast, prostate, and lung carcinomas with poor prognosis*. Cancer Res, 2007. 67(17): p. 8065-80.
7. Yecies, J. L. and B. D. Manning, *Transcriptional Control of Cellular Metabolism by mTOR Signaling*. Cancer Research, 2011. 71(8): p. 2815-2820.
8. Guillermet-Guibert, J., L. Davenne, D. Pchejetski, N. Saint-Laurent, L. Brizuela, C. Guilbeau-Frugier, M.-B. Delisle, O. Cuvillier, C. Susini, and C. Bousquet, *Targeting the sphingolipid metabolism to defeat pancreatic cancer cell resistance to the chemotherapeutic gemcitabine drug*. Molecular Cancer Therapeutics, 2009. 8(4): p. 809-820.
9. Northen, T. R., O. Yanes, M. T. Northen, D. Marrinucci, W. Uritboonthai, J. Apon, S. L. Golledge, A. Nordström, and G. Siuzdak, *Clathrate nanostructures for mass spectrometry*. Nature, 2007. 449(7165): p. 1033-1036.
10. Hellerstein, M., *New stable isotope-mass spectrometric techniques for measuring fluxes through intact metabolic pathways in mammalian systems: introduction of moving pictures into functional genomics and biochemical phenotyping*. Metabolic Engineering, 2004.
11. Price, J. C., S. Guan, A. Burlingame, S. B. Prusiner, and S. Ghaemmaghami, *Analysis of proteome dynamics in the mouse brain*. Proceedings of the National Academy of Sciences, 2010. 107(32): p. 14508.
12. Weigelt, B., J. L. Peterse, and L. J. Van't Veer, *Breast cancer metastasis: markers and models*. Nat Rev Cancer, 2005. 5(8): p. 591-602.
13. Baran, R., W. Reindl, and T. R. Northen, *Mass spectrometry based metabolomics and enzymatic assays for functional genomics*. Curr Opin Microbiol, 2009. 12(5): p. 547-52.
14. Viale, A. and S. Aime, *Current concepts on hyperpolarized molecules in MRI*. Current Opinion in Chemical Biology, 2010. 14(1): p. 90-96.
15. Nordstrom, A. and R. Lewensohn, *Metabolomics: moving to the clinic*. J Neuroimmune Pharmacol, 2009. 5(1): p. 4-17.
16. Lee do, Y., B. P. Bowen, and T. R. Northen, *Mass spectrometry-based metabolomics, analysis of metabolite-protein interactions, and imaging*. Biotechniques, 2010. 49(2): p. 557-65.
17. Roddy, T. P., D. M. Cannon, C. A. Meserole, N. Winograd, and A. G. Ewing, *Imaging of freeze-fractured cells with in situ fluorescence and time-of-flight secondary ion mass spectrometry*. Analytical Chemistry, 2002. 74(16): p. 4011-4019.
18. Winograd, N., Z. Postawa, J. Cheng, C. Szakal, J. Kozole, and B. Garrison, *Improvements in SIMS continuels the end in sight?* Applied Surface Science, 2006. 252(19): p. 6836-6843.

19. Cornett, D. S., M. L. Reyzer, P. Chaurand, and R. M. Caprioli, *MALDI imaging mass spectrometry: molecular snapshots of biochemical systems*. Nature Methods, 2007. 4(10): p. 828-833.
20. Jurchen, J. C., S. S. Rubakhin, and J. V. Sweedler, *MALDI-MS imaging of features smaller than the size of the laser beam*. J Am Soc Mass Spectrom, 2005. 16(10): p. 1654-9.
21. Takats, Z., J. M. Wiseman, B. Gologan, and R. G. Cooks, *Mass spectrometry sampling under ambient conditions with desorption electrospray ionization*. Science, 2004. 306(5695): p. 471-473.
22. Wiseman, J. M., D. R. Ifa, Y. Zhu, C. B. Kissinger, N. E. Manicke, P. T. Kissinger, and R. G. Cooks, *Desorption electrospray ionization mass spectrometry: Imaging drugs and metabolites in tissues*. Proceedings of the National Academy of Sciences of the United States of America, 2008. 105(47): p. 18120-5.
23. Yanes, O., H. Woo, and T. Northen, and G. Siuzdak, *Nanostructure initiator mass spectrometry: tissue imaging and direct biofluid analysis*. Analytical Chemistry, 2009.
24. Lechene, C., F. Hillion, G. McMahon, D. Benson, A. M. Kleinfeld, J. P. Kampf, D. Distel, Y. Luyten, J. Bonventre, and D. Hentschel, *High-resolution quantitative imaging of mammalian and bacterial cells using stable isotope mass spectrometry*. Journal of biology, 2006. 5(6): p. 20.
25. Koeniger, S. L., N. Talaty, Y. Luo, D. Ready, M. Voorbach, T. Seifert, S. Cepa, J. A. Fagerland, J. Bouska, W. Buck, R. W. Johnson, and S. Spanton, *A quantitation method for mass spectrometry imaging*. Rapid Commun. Mass Spectrom., 2011. 25(4): p. 503-510.
26. Hellerstein, M. K. and R. A. Neese, *Mass isotopomer distribution analysis at eight years: theoretical, analytic, and experimental considerations*. American Journal of Physiology—Endocrinology And Metabolism, 1999. 276 (6): p. E1146.
27. Green, J., M. Shibata, K. Yoshidome, and M. Liu M. L., Jorcyk, C., Anver, M. R., Wigginton, J., Wiltrout, R., Shibata, E., Kaczmarczyk, S., Wang, W., Liu, Z. Y., Calvo, A., and Couldrey, C. *The C3 (1)/SV40 T-antigen transgenic mouse model of mammary cancer: ductal epithelial cell targeting with multistage progression to carcinoma*. Oncogene, 2000.
28. Bowen, B. P. and T. R. Northen, *Dealing with the unknown: metabolomics and metabolite atlases*. J Am Soc Mass Spectrom, 2010. 21(9): p. 1471-6.
29. Reis-Filho, J. S. and A. N. Tutt, *Triple negative tumours: a critical review*. Histopathology, 2008. 52(1): p. 108-18.
30. Liedtke, C., C. Mazouni, K. R. Hess, F. Andre, A. Tordai, J. A. Mejia, W. F. Symmans, A. M. Gonzalez-Angulo, B. Hennessy, M. Green, M. Cristofanilli, G. N. Hortobagyi, and L. Pusztai, *Response to neoadjuvant therapy and long-term survival in patients with triple-negative breast cancer*. J Clin Oncol, 2008. 26(8): p. 1275-81.
31. Kennecke, H., R. Yerushalmi, R. Woods, M. C. Cheang, D. Voduc, C. H. Speers, T. O. Nielsen, and K. Gelmon, *Metastatic behavior of breast cancer subtypes*. J Clin Oncol, 2010. 28(20): p. 3271-7.
32. Neve, R. M., K. Chin, J. Fridlyand, J. Yeh, F. L. Baehner, T. Fevr, L. Clark, N. Bayani, J. P. Coppe, F. Tong, T. Speed, P. T. Spellman, S. DeVries, A. Lapuk, N.J. Wang, W. L. Kuo, J. L. Stilwell, D. Pinkel, D. G. Albertson, F. M. Waldman, F. McCormick, R. B. Dickson, M. D. Johnson, M. Lippman, S. Ethier, A. Gazdar, and J. W. Gray, *A collection of breast cancer cell lines for the study of functionally distinct cancer subtypes*. Cancer Cell, 2006. 10(6): p. 515-27.
33. Reindl, W. and T. R. Northen, *Rapid Screening of Fatty Acids Using Nanostructure-Initiator Mass Spectrometry*. Analytical chemistry, 2010. 82(9): p. 3751-3755.
34. Lee, W., S. Bassilian, H. Ajie, D. Schoeller, J. Edmond, E. Bergner, and L. Byerley, *In vivo measurement of fatty acids and cholesterol synthesis using D2O and mass isotopomer analysis*. American Journal of Physiology-Endocrinology And Metabolism, 1994. 266(5): p. E699.
35. Woo, H., T. Northen, O. Yanes, and G. Siuzdak, *Nanostructure-initiator mass spectrometry: a protocol for preparing and applying NIMS surfaces for high-sensitivity mass analysis*. Nature Protocols, 2008. 3(8): p. 1341-1349.
36. Lis, G., L. Wassenaar, and M. Hendry, *High-precision laser spectroscopy D/H and 18O/16O measurements of microliter natural water samples*. Analytical chemistry, 2008. 80(1): p. 287-293.
37. Reindl, W., B. P. Bowen, M. A. Balamotis, J. E. Green, and T. R. Northen, *Multivariate analysis of a 3D mass spectral image for examining tissue heterogeneity*. Integr. Biol., 2011. 3(4): p. 460.
38. Kasumov, T., S. Ilchenko, L. Li, N. Rachdaoui, R. Sadigov, B. Willard, A. J. Mccullough, and S. Previs, *Measuring protein synthesis using metabolic 2H labeling, high-resolution mass spectrometry, and an algorithm*. Anal Biochem, 2011: p. 1-9.
39. Commerford, S. L., A. L. Carsten, and E. P. Cronkite, *The distribution of tritium among the amino acids of proteins obtained from mice exposed to tritiated water*. Radiat Res, 1983. 94(1): p. 151-5.
40. Busch, R., Y. K. Kim, R. A. Neese, V. Schade-Serin, M. Collins, M. Awada, J. L. Gardner, C. Beysen, M. E. Marino, and L. M. Misell, *Measurement of protein turnover rates by heavy water labeling of nonessential amino acids*. Biochimica et Biophysica Acta (BBA)—General Subjects, 2006. 1760(5): p. 730-744.
41. Herschkowitz, J. I., X. He, C. Fan, and C. M. Perou, *The functional loss of the retinoblastoma tumour suppressor is a common event in basal-like and luminal B breast carcinomas*. Breast Cancer Res, 2008. 10(5): p. R75.
42. Jiang, Z., T. Deng, R. Jones, H. Li, J. I. Herschkowitz, J. C. Liu, V. J. Weigman, M. S. Tsao, T. F. Lane, C. M. Perou, and E. Zacksenhaus, *Rb deletion in mouse mammary progenitors induces luminal-B or basal-like/EMT tumor subtypes depending on p53 status*. J Clin Invest, 2010.
43. Trere, D., E. Brighenti, G. Donati, C. Ceccarelli, D. Santini, M. Taffurelli, L. Montanaro, and M. Derenzini, *High prevalence of retinoblastoma protein loss in triple-negative breast cancers and its association with a good prognosis in patients treated with adjuvant chemotherapy*. Ann Oncol, 2009. 20(11): p. 1818-23.
44. Borowsky A D, Namba R, Young L J, Hunter K W, Hodgson J G, Tepper C G, McGoldrick E T, Muller W J, Cardiff R D, Gregg J P, *Syngeneic mouse mammary carcinoma cell lines: two closely related cell lines with divergent metastatic behavior*. Clin Exp Metastasis. 2005; 22(1):47-59.
45. Messmer, B. T., *In vivo measurements document the dynamic cellular kinetics of chronic lymphocytic leukemia B cells*. Journal of Clinical Investigation, 2005. 115(3): p. 755-764.
46. Lindwall, G., E. A. Hsieh, L. M. Misell, C. M. Chai, S. M. Turner, and M. K. Hellerstein, *Heavy Water Labeling* of Keratin as a Non-Invasive Biomarker of Skin Turnover In Vivo in Rodents and Humans*. J Investig Dermatol, 2006. 126(4): p. 841-848.
47. McCune, J. M., M. B. Hanley, D. Cesar, R. Halvorsen, R. Hoh, D. Schmidt, E. Wieder, S. Deeks, S. Siler, and R. Neese, *Factors influencing T-cell turnover in HIV-1-seropositive patients*. Journal of Clinical Investigation, 2000. 105(5): p. R1.
48. Misell, L. M., E. S. Hwang, A. Au, L. Esserman, and M. K. Hellerstein, *Development of a novel method for measuring in vivo breast epithelial cell proliferation in humans*. Breast Cancer Res Treat, 2005. 89(3): p. 257-264.
49. Bartella, L., E. A. Morris, D. D. Dershaw, L. Liberman, S. B. Thakur, C. Moskowitz, J. Guido, and W. Huang, *Proton MR spectroscopy with choline peak as malignancy marker improves positive predictive value for breast cancer diagnosis: Preliminary study*. Radiology, 2006. 239 (3): p. 686-692.
50. Ogretmen, B. and Y. A. Hannun, *Biologically active sphingolipids in cancer pathogenesis and treatment*. Nat Rev Cancer, 2004. 4(8): p. 604-16.
51. Swinnen, J. V., Brusselmans, K. & Verhoeven, G. Increased lipogenesis in cancer cells: new players, novel targets. *Current opinion in clinical nutrition and metabolic care* 9, 358-365 (2006).
52. Abramson, H. N. The lipogenesis pathway as a cancer target. *Journal of medicinal chemistry* 54, 5615-5638 (2011).
53. Spector, A. A. & Yorek, M. A. Membrane lipid composition and cellular function. *Journal of lipid research* 26, 1015-1035 (1985).
54. Deberardinis, R. J., Sayed, N., Ditsworth, D. & Thompson, C. B. Brick by brick: metabolism and tumor cell growth. *Current opinion in genetics & development* 18, 54-61 (2008).
55. Schwamborn, K. & Caprioli, R. M. Molecular imaging by mass spectrometry—looking beyond classical histology. *Nat Rev Cancer* 10, 639-646 (2010).
56. McMahon, G., Glassner, B. J. & Lechene, C. P. Quantitative imaging of cells with multi-isotope imaging mass spectrometry (MIMS)-Nanoautography with stable isotope tracers. *Appl Surf Sci* 252, 6895-6906 (2006).
57. Diraison, F., Pachiaudi, C. & Beylot, M. In vivo measurement of plasma cholesterol and fatty acid synthesis with deuterated water: determination of the average number of deuterium atoms incorporated. *Metabolism: clinical and experimental* 45, 817-821 (1996).
58. Turner, S. M. et al. Measurement of TG synthesis and turnover in vivo by 2H2O incorporation into the glycerol moiety and application of MIDA. *American journal of physiology. Endocrinology and metabolism* 285, E790-803 (2003).
59. Schiller, J. et al. Matrix-assisted laser desorption and ionization time-of-flight (MALDI-TOF) mass spectrometry in lipid and phospholipid research. *Progress in Lipid Research* 43, 449-488 (2004).
60. Murphy, R. C., Hankin, J. A. & Barkley, R. M. Imaging of lipid species by MALDI mass spectrometry. *Journal of lipid research* 50 Suppl, S317-322 (2009).
61. Lee do, Y. et al. Resolving brain regions using nanostructure initiator mass spectrometry imaging of phospholipids. *Integrative biology: quantitative biosciences from nano to macro* 4, 693-699 (2012).
62. Quehenberger, O. & Dennis, E. A. The human plasma lipidome. *The New England journal of medicine* 365, 1812-1823 (2011).
63. Ackerstaff, E., Glunde, K. & Bhujwalla, Z. M. Choline phospholipid metabolism: a target in cancer cells? *Journal of cellular biochemistry* 90, 525-533 (2003).
64. Wadke, M., Brunengraber, H., Lowenstein, J. M., Dolhun, J. J. & Arsenault, G. P. Fatty acid synthesis by liver perfused with deuterated and tritiated water. *Biochemistry* 12, 2619-2624 (1973).
65. Ajie, H. O. et al. In-Vivo Study of the Biosynthesis of Long-Chain Fatty-Acids Using Deuterated Water. *Am J Physiol-Endoc M* 269, E247-E252 (1995).
66. Hankin, J. A. & Murphy, R. C. Relationship between MALDI IMS Intensity and Measured Quantity of Selected Phospholipids in Rat Brain Sections. *Anal Chem* 82, 8476-8484 (2010).
67. Jones, E. A. et al. Multiple statistical analysis techniques corroborate intratumor heterogeneity in imaging mass spectrometry datasets of myxofibrosarcoma. *Plos One* 6, e24913 (2011).
68. Dowsett, M. et al. Assessment of Ki67 in breast cancer: recommendations from the International Ki67 in Breast Cancer working group. *Journal of the National Cancer Institute* 103, 1656-1664 (2011).
69. Hilvo, M. et al. Novel theranostic opportunities offered by characterization of altered membrane lipid metabolism in breast cancer progression. *Cancer research* 71, 3236-3245 (2011).
70. Igal, R. A. Stearoyl-CoA desaturase-1: a novel key player in the mechanisms of cell proliferation, programmed cell death and transformation to cancer. *Carcinogenesis* 31, 1509-1515 (2010).
71. Maheo, K. et al. Differential sensitization of cancer cells to doxorubicin by DHA: a role for lipoperoxidation. *Free radical biology & medicine* 39, 742-751 (2005).
72. Bougnoux, P., Hajjaji, N., Maheo, K., Couet, C. & Chevalier, S. Fatty acids and breast cancer: sensitization to treatments and prevention of metastatic re-growth. *Prog Lipid Res* 49, 76-86 (2010).
73. Bertos, N. R. & Park, M. Breast cancer—one term, many entities? *The Journal of clinical investigation* 121, 3789-3796 (2011).
74. Marusyk, A. & Polyak, K. Tumor heterogeneity: Causes and consequences. *Bba-Rev Cancer* 1805, 105-117 (2010).
75. Tennant, D. A., Duran, R. V., Boulahbel, H. & Gottlieb, E. Metabolic transformation in cancer. *Carcinogenesis* 30, 1269-1280 (2009).
76. Hanahan, D. & Weinberg, R. A. Hallmarks of cancer: the next generation. *Cell* 144, 646-674 (2011).
77. Gerlinger, M. et al. Intratumor heterogeneity and branched evolution revealed by multiregion sequencing. *The New England journal of medicine* 366, 883-892 (2012).
78. Rockwood, A. L. & VanOrden, S. L. Ultrahigh-speed calculation of isotope distributions. *Anal Chem* 68, 2027-2030 (1996).
79. Rockwood, A. L., Vanorden, S. L. & Smith, R. D. Rapid Calculation of Isotope Distributions. *Anal Chem* 67, 2699-2704 (1995).
80. Lawson, C. L. & Hanson, R. J. Solving least squares problems. (Prentice-Hall, Englewood Cliffs, N.J.; 1974).
81. Price, J. C. et al. Measurement of human plasma proteome dynamics with (2)H(2)O and liquid chromatography tandem mass spectrometry. *Analytical biochemistry* 420, 73-83 (2012).
82. Zeisel, S. H. Choline: an essential nutrient for humans. *Nutrition* 16, 669-671 (2000).

What is claimed is:

1. A method for measuring molecular flux rates of a target molecule of interest at a plurality of locations of a histopathology specimen from a sample, the method comprising:
    (a) obtaining the histopathology specimen from the sample, wherein the sample is from a tissue of an individual, and
        wherein the individual was administered an isotope-labeled precursor comprising an isotope label for a period of time sufficient for one or more of the isotope labels to become incorporated into the target molecule of interest prior to collection of the sample;
    (b) subjecting the histopathology specimen to a mass spectrometry method, the mass spectrometry method comprising:
        (i) subjecting the histopathology specimen to processing via an energy-induced volatilization system at each of the plurality of locations,
            wherein each of the plurality of locations of the histopathology specimen have a known spatial relationship,
            wherein the energy-induced volatilization system emits a focused beam of energy to generate a series of discrete packets or a continuous flow of ions via soft desorption at each of the plurality of locations, and
            wherein ions of the target molecule of interest, if present, are subjected to volatilization into non-fragmented, gas-phase ions; and
        (ii) directing the ions generated at each of the plurality of locations to a mass analyzer of a mass spectrometer,
    thereby obtaining mass spectrometry data of the histopathology specimen specific to each of the plurality of locations; and
    (c) determining molecular flux rates of the target molecule of interest at each of the plurality of locations of the histopathology specimen, the determining comprising:
        (i) measuring relative or absolute abundances of mass isotopomers within isotopomeric envelopes of ions of the target molecule of interest at each of the plurality of locations using the obtained mass spectrometry data specific to the respective location; and
        (ii) calculating the molecular flux rates of the target molecule of interest at each of the plurality of locations,
            wherein for each of the plurality of locations the calculation is based on a change in pattern or relative abundances of mass isotopomers for each isotopomeric envelope of the target molecule of interest at the respective location compared to the natural abundances of the mass isotopomers of the target molecule of interest,
    thereby measuring molecular flux rates of the target molecule of interest at the plurality of locations of the histopathology specimen from the sample.

2. The method of claim 1, further comprising mapping the molecular flux rates of the target molecule of interest at the plurality of locations after measuring molecular flux rates at the plurality of locations.

3. The method of claim 1, wherein the isotope label is selected from the group consisting of $^{2}H$, $^{13}O$, $^{15}N$, $^{18}O$, $^{33}S$ and $^{34}S$.

4. The method of claim 3, wherein the isotope label is $^{2}H$.

5. The method of claim 1, wherein the isotope-labeled precursor is selected from the group consisting of isotope-labeled $H_2O$, isotope-labeled $CO_2$, isotope-labeled $NH_3$, isotope-labeled glucose, isotope-labeled lactate, and isotope-labeled $HCO_3$.

6. The method of claim 1, wherein the isotope-labeled precursor is selected from the group consisting of $^{2}H_2O$, $H_2^{18}O$, $^{13}CO_2$, $C^{18}O^{17}O$, $H^{16}CO_3$, $^{15}NH_3$, $^{2}H$-labeled amino acids, $^{13}C$-labeled amino acids, $^{15}N$-labeled amino acids, $^{18}O$-labeled amino acids, $^{34}S$-labeled amino acids, and $^{33}S$-labeled amino acids.

7. The method of claim 6, wherein the isotope-labeled precursor is $^{2}H_2O$.

8. The method of claim 1, wherein administration of the isotope-labeled precursor is by oral administration.

9. The method of claim 1, wherein the individual is a human.

10. The method of claim 1, wherein the determining molecular flux rates of the target molecule of interest at the plurality of locations employs mass isotopomer distribution analysis (MIDA) or spectral pattern isotope fitter (SPIF) analysis.

11. The method of claim 1, further comprising outputting molecular flux rates of the target molecule of interest at the plurality of locations in an output form of an image, a heat map, a contour map, a table or a database.

12. The method of claim 1, wherein the output form is two-dimensional or three-dimensional.

13. The method of claim 1, wherein the known spatial relationship of each of the plurality of locations is based on distance, cells, or cellular compartments.

14. The method of claim 11, wherein the outputting molecular flux rates comprises displaying each molecular flux rate of the plurality of locations as an image, wherein the image has a first location and a second location,
    wherein the first location of the image has a pattern, a color, a number, or a combination thereof, representing the one or more molecular flux rates for the one or more molecules of interest in the first location of the sample; and
    wherein the second location of the image has a pattern, a color, a number representing the one or more molecular flux rates for the one or more molecules of interest in the second location of the sample.

15. The method of claim 1, wherein the focused beam of energy is a laser beam.

16. The method of claim 1, wherein the energy-induced volatilization system is selected from the group consisting of matrix-assisted laser desorption ionization (MALDI), nanoparticle initiator mass spectrometry (NIMS), secondary ion mass spectrometry (SIMS), laser desorption, desorption electrospray ionization (DESI), probe electrospray ionization (PESI), laser spray, and laser ablation electrospray ionization (LAESI).

17. The method of claim 1, wherein the ions originating from each of the plurality of locations is independently directed into a mass analyzer for mass spectrometry by an instrument modality, wherein the instrument modality is selected from the group consisting of time-of-flight (TOF), Orbitrap, Fourier-transform ion cyclotron (FTIR), magnetic sector, quadrupole, tandem mass spectrometers (MS/MS).

18. The method of claim 1, further comprising the step of subjecting the sample to liquid chromatography electrospray ionization mass-spectrometry (LC ESI-MS) or tandem mass spectrometry (MS-MS).

* * * * *

UNITED STATES PATENT AND TRADEMARK OFFICE
CERTIFICATE OF CORRECTION

PATENT NO. : 10,386,371 B2
APPLICATION NO. : 14/343334
DATED : August 20, 2019
INVENTOR(S) : Benjamin P. Bowen et al.

It is certified that error appears in the above-identified patent and that said Letters Patent is hereby corrected as shown below:

In the Claims

Column 57, Claim 3, Line 62: replace "$^{13}O$" with --$^{13}C$--;

Column 58, Claim 17, Line 61: replace "quadrupole, tandem" with --quadrupole, and tandem--.

Signed and Sealed this
Thirty-first Day of December, 2019

Andrei Iancu
*Director of the United States Patent and Trademark Office*